United States Patent
Poulsen (12)

(10) Patent No.: US 6,483,009 B1
(45) Date of Patent: Nov. 19, 2002

(54) ANTISENSE INTRON INHIBITION OF STARCH BRANCHING ENZYME EXPRESSION

(75) Inventor: Peter Poulsen, Copenhagen K (DK)

(73) Assignee: Danisco a/s, Copenhagen K (DK)

( * ) Notice: Subject to any disclaimer, the term of this patent is extended or adjusted under 35 U.S.C. 154(b) by 0 days.

(21) Appl. No.: 09/367,895

(22) PCT Filed: Feb. 23, 1998

(86) PCT No.: PCT/IB98/00270

§ 371 (c)(1),
(2), (4) Date: Dec. 8, 1999

(87) PCT Pub. No.: WO98/37213

PCT Pub. Date: Aug. 27, 1998

(30) Foreign Application Priority Data

Feb. 21, 1997 (GB) ............................................. 9703663
Mar. 24, 1997 (GB) ............................................. 9706060

(51) Int. Cl.[7] .......................... C12N 15/29; C12N 5/04; C12N 15/82; A01H 5/00; C12P 19/04

(52) U.S. Cl. ....................... 800/284; 800/278; 800/286; 800/317.2; 435/320.1; 435/419; 536/23.6; 536/24.5

(58) Field of Search ................................ 800/278, 284, 800/286, 317.2; 435/320.1, 419; 536/23.6, 24.5

(56) References Cited

U.S. PATENT DOCUMENTS

| 5,107,065 A | 4/1992 | Shewmaker et al. ........ 800/205 |
| 5,721,352 A | * 2/1998 | Moyer et al. ............... 536/23.2 |

FOREIGN PATENT DOCUMENTS

| CA | A-2006454 | 6/1990 |
| EP | A-0120516 | 10/1984 |
| EP | A-0449375 | 10/1991 |
| EP | A-0458367 | 11/1991 |
| EP | A-0467349 | 1/1992 |
| EP | A-0470145 | 2/1992 |
| EP | A-0647715 | 4/1995 |
| WO | 0 240 208 | 10/1987 |
| WO | 92/11375 | 7/1992 |
| WO | 92/14827 | 9/1992 |
| WO | WO 92/15680 | 9/1992 |
| WO | WO 94/09114 | 4/1994 |
| WO | 94/24292 | 10/1994 |
| WO | 96/34968 | 11/1996 |
| WO | 97/04112 | 2/1997 |
| WO | 97/04113 | 2/1997 |

OTHER PUBLICATIONS

Merkelbach, S. et al., "Cloning, sequence analysis and expression of a cDNA encoding active phosphoenolpyruvate carboxylase of the C3 plant *Solanum tuberosum*." 1993, Plant Molecular Biology, vol. 23, pp. 881–888.*

Willmitzer et al. Plant Polymeric Carbohydrates, pp. 33–39, Jan. 1993.*
Bourque, "Antisense strategies for genetic manipulations in plants", Plant Science 105, pp. 125–149 1995.
Kuipers et al., "Factors affecting the inhibition by antisense RNA of granule–bound starch synthase gene expression in potato", Mol. Gen. Genet. 246, pp. 745–755, 1995.
Kull et al., "Genetic engineering of potato starch composition: inhibition of amylose biosynthesis in tubers from transgenic potato lines by the expressif antisense sequences of the gene for granule–bound starch synthase", J. Genet & Breed 49, pp. 69–76, 1995.
Shimada et al., "Antisense regulation of the rice waxy gene expression using a PCR–amplified fragment of the rice genome reduces the amylose content in grain starch", Theor. Appl. Genet. pp. 665–672, 1993.
Finnegan & McElroy, "Transgene Inactivation: Plants fight Back!", Biotechnology 12, pp. 883–888, 1994.
Matzke and Matzke, "Homology–dependent gene silencing in transgenic plants: what does it really tell us?", TIG 11, pp. 1–3, 1995.
Dowson Day et al., "Plant viral leaders influence expression of a reporter gene in tobacco" Dowson Plant Mol. Biol. 23, pp. 97–109, 1993.
Potrykus, "Gene Transfer to Plants: Assessment of Published Approaches and Results", Annu. Rev. Plant Physiol. Plant Mol. Biol., 42:205–225, 1991.
Christou, "Genetic engineering of crop legumes and cereals: current status and recent advances", Agro–Food Industry Hi–Tech, pp. 17–27, Mar./Apr. 1994.
Gynheung An, et al., "Transformation of tobacco, Tomato, Potato, and Arabidopsis thaliana Using a Binary Ti Vector System[1]", Plant Physiol. 81, pp. 301–305 1980.
Butcher D.N. et al., "The role of tissue culture in the study of crown–gall tumorigenesis", Tissue Culture Methods for Plant Pathologists, eds. D.S. Ingrams and J.P. Helgeson, pp. 203–208.
An et al., "New cloning vehicles for transformation of higher plants", EMBO J. 4:277–284 1985.
Poulsen & Kreiberg, "Starch Branching Enzyme cDNA from Solanum Tuberosum", Plant Physiol. 102 pp. 1053–1054.

(List continued on next page.)

Primary Examiner—David T. Fox
(74) Attorney, Agent, or Firm—Foley & Lardner

(57) ABSTRACT

A method for affecting enzymatic activity in a starch producing organism is described. The method comprises expressing in the organism: (a) a first nucleotide which comprises, partially or completely, a first intron of a gene encoding a class A starch branching enzyme in an antisense orientation, wherein the first nucleotide sequence does not contain a sequence that is antisense to an exon sequence naturally associated with the first intron, (b) together with a second nucleotide sequence which comprises, partially or completely, a second intron of a class B starch branching enzyme in an antisense or sense orientation. Also described are antisense sequences, constructs, vectors, transformed cells, and transgenic organisms.

10 Claims, 27 Drawing Sheets

OTHER PUBLICATIONS

Linsmaier, E.U. and Skoog, F., "Organic Growth Factor Requirements of Tobacco Tissue Cultures", Physiol Plant 18, pp. 100–127 1965.

Redke, S.E. et al., Transformation of *Brassica napus* I. using *Agrobacterium tumefaciens*: developmentally regulated expression of a reintroduced napin gene, Theor. Appl. Genet. 75, pp. 685–694 1988.

Hodal, L. et al., "Detection, expression and specific elimination of endogenous B–glucuronidase activity in transgenic and non–transgenic plants", P1 Sci. 87, pp. 115–122 1992.

Blennow and Johansson, "Isolation of a Q–Enzyme with $M_r$ 103 000 from Potato Tubers", Phytochemistry 30, pp. 437–444 1991.

Hovenhamp–Hermelink et al., "Rapid estimation of the amylose/amylopectin ratio in small amounts of tuber and leaf tissue of the potato", Potato Research 31, pp. 241–246, 1988.

N. Nelson, "A Photometric Adaption of the Somogyi Method for the Determination of Glucose", J. Biol. Chem. 153:375–380, 1944.

* cited by examiner

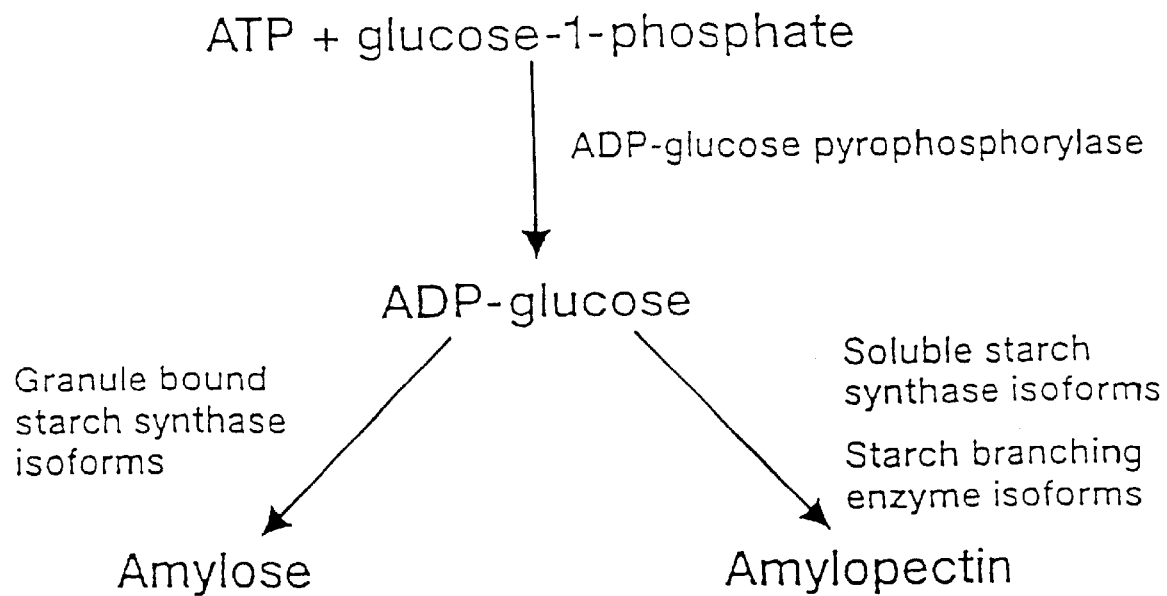
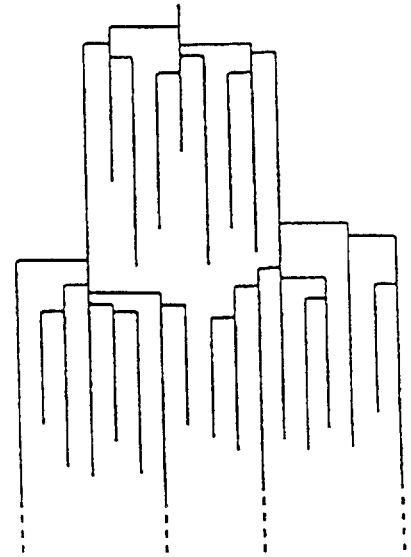
FIG. 1

```
          10        20        30        40        50        60
1234567890123456789012345678901234567890123456789012345678901234567890
ATCATGGCCAATTACTGGTTCAAATGCATTACTTCCTTTCAGATTCTTTCGAGTTCTCAT    60
GACCGGTCCTACTACAGACGATACTAACCCGTGGAACTGTTGCATCTGCTTCTTAGAACT   120
CTATGGCTATTTTCGTTAGCTTGGCGTCGGTTTGAACATAGTTTTTGTTTTCAAACTCTT   180
CATTTACAGTCAAAATGTTGTATGGTTTTTGTTTTCCTCAATGATGTTTACAGTGTTGTG   240
TTGTCATCTGTACTTTTGCCTATTACTTGTTTTGAGTTACATGTTAAAAAAGTGTTTATT   300
TTGCCATATTTTGTTCTCTTATTATTATTATCATACATACATTATTACAAGGAAAAGACA   360
AGTACACAGATCTTAACGTTTATGTTCAATCAACTTTTGGAGGCATTGACAGGTACCACA   420
AATTTTGAGTTTATGATTAAGTTCAATCTTAGAATATGAATTTAACATCTATTATAGATG   480
CATAAAAATAGCTAATGATAGAACATTGACATTTGGCAGAGCTTAGGGTATGGTATATCC   540
AACGTTAATTTAGTAATTTTTGTTACGTACGTATATGAAATATTGAATTAATCACATGAA   600
CGGTGGATATTATATTATGAGTTGGCATCAGCAAAATCATTGGTGTAGTTGACTGTAGTT   660
GCAGATTTAATAATAAAATGGTAATTAACGGTCGATATTAAAATAACTCTCATTTCAAGT   720
GGGATTAGAACTAGTTATTAAAAAAATGTATACTTTAAGTGATTTGATGGCATATAATTT   780
AAAGTTTTTCATTTCATGCTAAAATTGTTAATTATTGTAATGTAGACTGCGACTGGAATT   840
ATTATAGTGTAAATTTATGCATTCAGTGTAAAATTAAAGTATTGAACTTGTCTGTTTTAG   900
AAAATACTTTATACTTTAATATAGGATTTTGTCATGCGAATTTAAATTAATCGATATTGA   960
ACACGGAATACCAAAATTAAAAAGGATACACATGGCCTTCATATGAACCGTGAACCTTTG  1020
ATAACGTGGAAGTTCAAAGAAGGTAAAGTTTAAGAATAAACTGACAAATTAATTTCTTTT  1080
ATTTGGCCCACTACTAAATTTGCTTTACTTTCTAACATGTCAAGTTGTGCCCTCTTAGTT  1140
GAATGATATTCATTTTTCATCCCATAAGTTCAATTTGATTGTCATACCACCCATGATGTT  1200
CTGAAAAATGCTTGGCCATTCACAAAGTTTATCTTAGTTCCTATGAACTTTATAAGAAGC  1260
TTTAATTTGACATGTTATTTATATTAGATGATATAATCCATGACCCAATAGACAAGTGTA  1320
TTAATATTGTAACTTTGTAATTGAGTGTGTCTACATCTTATTCAATCATTTAAGGTCATT  1380
AAAATAAATTATTTTTTGACATTCTAAAACTTTAAGCAGAATAAATAGTTTATCAATTAT  1440
TAAAAACAAAAAACGACTTATTTATAAATCAACAAACAATTTTAGATTGCTCCAACATAT  1500
```

FIG. 12A

```
          10        20        30        40        50        60
 123456789012345678901234567890123456789012345678901234567890
TTTTCCAAATTAAATGCAGAAAATGCATAATTTTATACTTGATCTTTATAGCTTATTTTT    1560
TTTAGCCTAACCAACGAATATTTGTAAACTCACAACTTGATTAAAAGGGATTTACAACAA    1620
GATATATATAAGTAGTGACAAATCTTGATTTTAAATATTTTAATTTGGAGGTCAAAATTT    1680
TACCATAATCATTTGTATTTATAATTAAATTTTAAATATCTTATTTATACATATCTAGTA    1740
AACTTTTAAATATACGTATATACAAAATATAAAATTATTGGCGTTCATATTAGGTCAATA    1800
AATCCTTAACTATATCTGCCTTACCACTAGGAGAAAGTAAAAAACTCTTTACCAAAAATA    1860
CATGTATTATGTATACAAAAAGTCGATTAGATTACCTAAATAGAAATTGTATAACGAGTA    1920
AGTAAGTAGAAATATAAAAAAACTACAATACTAAAAAAAATATGTTTTACTTCAATTTCG    1980
AAACTAATGGGGTCTGAGTGAAATATTCAGAAAGGGGAGGACTAACAAAAGGGTCATAAT    2040
GTTTTTTTATAAAAAGCCACTAAAATGAGGAAATCAAGAATCAGAACATACAAGAAGGCA    2100
GCAGCTGAAGCAAAGTACCATAATTTAATCAATGGAAATTAATTTCAAAGTTTTATCAAA    2160
                             M  E  I  N  F  K  V  L  S  K
ACCCATTCGAGGATCTTTTCCATCTTTCTCACCTAAAGTTTCTTCAGGGtaatttttac    2220
 P  I  R  G  S  F  P  S  F  S  P  K  V  S  S  G
taatttcatgttaatttcaattattttagcctttgcatttcattttccaatatatctgg    2280
atcatctccttagttttttatttattttttataatatcaaatatggaagaaaaatgaca    2340
cttgtagagccatatgtaagtatcatgtgacaaatttgcaaggtggttgagtgtataaaa    2400
ttcaaaaattgagagatggagggggggtgggggbaragacaatatttagaaagagtgttc    2460
taggaggttatggaggacacggatgagggtagaaggttagttaggtatttgagtgttgt    2520
ctggcttatccttcatactagtagtcgtggaattatttgggtagttcttgttttgtta    2580
tttgatctttgttattctatttctgtttcttgtacttcgattattgtattatatatctt    2640
gtcgtagttattgttcctcggtaagaatgctctagcatgcttcctttagtgttttatcat    2700
gccttctttatattcgcgttgctttgaaatgcttttactttagccgagggtctattagaa    2760
acaatctctctatctcgtaaggtaggggtaaagtcctcaccacactccacttgtgggatt    2820
acattgtgttgttgttgtaaatcaattatgtatacataataagtggatttttacaaca    2880
caaatacatggtcaagggcaaagttctgaacacataaagggttcattatatgtccaggga    2940
tatgataaaaattgtttctttgtgaaagttatataagatttgttatggcttttgctggaa    3000
```

FIG. 12B

```
          10        20        30        40        50        60
1234567890123456789012345678901234567890123456789012345678901234567890
acataataagttataatgctgagatagctactgaagtttgttttttctagccttttaaat       3060 gtaccaataatagattccgtatcgaacgagtatgttttgattacctggtcatgatgtttc       3120 tattttttacatttttttggtgttgaactgcaattgaaaatgctgtatcctatgagacgg       3180 atagttgagaatgtgttctttgtatggaccttgagaagctcaaacgctactccaataatt       3240 tctatgaattcaaattcagtttatggctaccagtcagtccagaaattaggatatgctgca       3300 tatacttgttcaattatactgtaaaatttcttaagttctcaagatatccatgtaacctcg       3360 agaatttctttgacagGCTTCTAGAAATAAGATATGTTTTCCTTCTCAACATAGTACTGG       3420
                 A  S  R  N  K  I  C  F  P  S  Q  H  S  T  G
ACTGAAGTTTGGATCTCAGGAACGGTCTTGGATATTTCTTCCACCCCAAAATCAAGAGT        3480
 L  K  F  G  S  Q  E  R  S  W  D  I  S  S  T  P  K  S  R  V
TAGAAAAGATGAAAGGgtatgtttgataatttatatggttgcatggatagtatataaata       3540
 R  K  D  E  R
gttggaaaacttctggactggtgctcatggcatatttgatctgtgcaccgtgtggagatg       3600 tcaaacatgtgttacttcgttccgccaatttataataccttaacttgggaagacagctc       3660 tttactcctgtgggcatttgttatttgaattacaatctttatgagcatggtgttttcaca       3720 ttatcaacttctttcatgtggtatataacagttttagctccgttaataccttcttctt       3780 tttgatataaactaactgtggtgcattgcttgcbkkkATGAAGCACAGTTCAGCTATTTC       3840
                                     M  K  H  S  S  A  I  S
CGCTGTTTTGACCGATGACGACAATTCGACAATGGCACCCCTAGAGGAAGATGTCAAGAC       3900
 A  V  L  T  D  D  D  N  S  T  M  A  P  L  E  E  D  V  K  T
TGAAAATATTGGCCTCCTAAATTTGGATCCAACTTTGGAACCTTATCTAGATCACTTCAG       3960
 E  N  I  G  L  L  N  L  D  P  T  L  E  P  Y  L  D  H  F  R
ACACAGAATGAAGAGATATGTGGATCAGAAAATGCTCATTGAAAAATATGAGGGACCCCT       4020
 H  R  M  K  R  Y  V  D  Q  K  M  L  I  E  K  Y  E  G  P  L
TGAGGAATTTGCTCAAGgtaacagccaaaagttgtgctttaggcagtttgaccttatttt       4080
 E  E  F  A  Q  G
ggaagatgaattgtttatacctactttgactttgctagagaattttgcataccggggagt       4140 aagtagtggctccatttaggtggcacctggccattttttttgatcttttaaaaagctgttt      4200 gattgggtcttcaaaaaagtagacaaggttttttggagaagtgacacaccccggagtgtc       4260 agtggcaaagcaaagattttcactaaggagattcaaaatataaaaaaagtatagacataa       4320 agaagctgaggggattcaacatgtactatacaagcatcaaatatagtcttaaagcaattt       4380 tgtagaaataaagaaagtcttccttctgttgcttcacaatttccttctattatcatgagt       4440 tactctttctgttcgaaatagcttccttaatattaaattcatgatacttttgttgagatt       4500
```

FIG. 12C

```
          10        20        30        40        50        60
1234567890123456789012345678901234567890123456789012345678901234567890
tagcagtttttcttgtgtaaactgctctcttttttgcagGTTATTTAAAATTTGGATT            4560
                                        Y  L  K  F  G  F
CAACAGGGAAGATGGTTGCATAGTCTATCGTGAATGGGCTCCTGCTGCTCAgtaggtcct          4620
 N  R  E  D  G  C  I  V  Y  R  E  W  A  P  A  A  Q
cgtctactacaaaatagtagtttccatcatcataacagatttcctattaaagcatgacg           4680 ttgcagcatcattggctttcttacatgttctaattgctattaaggttatgcttctaatta         4740 actcatccacaatgcagGGAAGCAGAAGTTATTGGCGATTTCAATGGATGGAACGGTTCT          4800
                  E  A  E  V  I  G  D  F  N  G  W  N  G  S
AACCACATGATGGAGAAGGACCAGTTTGGTGTTTGGAGTATTAGAATTCCTGATGTTGAC          4860
 N  H  M  M  E  K  D  Q  F  G  V  W  S  I  R  I  P  D  V  D
AGTAAGCCAGTCATTCCACACAACTCCAGAGTTAAGTTTCGTTTCAAACATGGTAATGGA          4920
 S  K  P  V  I  P  H  N  S  R  V  K  F  R  F  K  H  G  N  G
GTGTGGGTAGATCGTATCCCTGCTTGGATAAAGTATGCCACTGCAGACGCCACAAAGTTT         4980
 V  W  V  D  R  I  P  A  W  I  K  Y  A  T  A  D  A  T  K  F
GCAGCACCATATGATGGTGTCTACTGGGACCCACCACCTTCAGAAAGgttttgttattca         5040
 A  A  P  Y  D  G  V  Y  W  D  P  P  P  S  E  R
taccttgaagctgaattttgaacaccatcatcacaggcatttcgattcatgttcttacta         5100 gtcttgttatgtaagacattttgaaatgcaaaagttaaaataattgtgtctttactaatt         5160 tggacttgatcccatactctttcccttaacaaaatgagtcaattctataagtgcttgaga         5220 acttactactcagcaattaaacagGTACCACTTCAAATACCCTCGCCCTCCCAAACCCC          5280
                        Y  H  F  K  Y  P  R  P  P  K  P  R
GAGCCCCACGAATCTATGAAGCACATGTCGGCATGAGCAGCTCTGAGCCACGTGTAAATT         5340
 A  P  R  I  Y  E  A  H  V  G  M  S  S  E  P  R  V  N  S
CGTATCGTGAGTTTGCAGATGATGTTTTACCTCGGATTAAGGCAAATAACTATAATACTG        5400
 Y  R  E  F  A  D  D  V  L  P  R  I  K  A  N  N  Y  N  T  V
TCCAGTTGATGGCCATAATGGAACATTCTTACTATGGATCATTTGGATATCATGTTACAA        5460
 Q  L  M  A  I  M  E  H  S  Y  Y  G  S  F  G  Y  H  V  T  N
ACTTTTTTGCTGTGAGCAGTAGATATGGAAACCCGGAGGACCTAAAGTATCTGATAGATA        5520
 F  F  A  V  S  S  R  Y  G  N  P  E  D  L  K  Y  L  I  D  K
AAGCACATAGCTTGGGTTTACAGGTTCTGGTGGATGTAGTTCACAGTCATGCAAGCAATA         5580
 A  H  S  L  G  L  Q  V  L  V  D  V  V  H  S  H  A  S  N  N
ATGTCACTGATGGCCTCAATGGCTTTGATATTGGCCAAGGTTCTCAAGAATCCTACTTTC        5640
 V  T  D  G  L  N  G  F  D  I  G  Q  G  S  Q  E  S  Y  F  H
ATGCTGGAGAGCGAGGGTACCATAAGTTGTGGGATAGCAGGCTGTTCAACTATGCCAATT        5700
 A  G  E  R  G  Y  H  K  L  W  D  S  R  L  F  N  Y  A  N  W
GGGAGGTTCTTCGTTTCCTTCTTTCCAACTTGAGGTGGTGGCTAGAAGAGTATAACTTTG        5760
 E  V  L  R  F  L  L  S  N  L  R  W  W  L  E  E  Y  N  F  D
ACGGATTTCGATTTGATGGAATAACTTCTATGCTGTATGTTCATCATGGAATCAATATGG        5820
 G  F  R  F  D  G  I  T  S  M  L  Y  V  H  H  G  I  N  M  G
GATTTACAGGAAACTATAATGAGTATTTCAGCGAGGCTACAGATGTTGATGCTGTGGTCT        5880
 F  T  G  N  Y  N  E  Y  F  S  E  A  T  D  V  D  A  V  V  Y
ATTTAATGTTGGCCAATAATCTGATTCACAAGATTTTCCCAGATGCAACTGTTATTGCCG         5940
 L  M  L  A  N  N  L  I  H  K  I  F  P  D  A  T  V  I  A  E
AAGATGTTTCTGGTATGCCGGGCCTTGGCCGGCCTGTTTCTGAGGGAGGAATTGGTTTTG         6000
 D  V  S  G  M  P  G  L  G  R  P  V  S  E  G  G  I  G  F  V
```

FIG. 12D

```
          10        20        30        40        50        60
 123456789012345678901234567890123456789012345678901234567890
 TTTACCGCCTGGCAATGGCAATCCCAGATAAGTGGATAGATTATTTAAAGAATAAGAATG    6060
  Y R L A M A I P D K W I D Y L K N K N D
 ATGAAGATTGGTCCATGAAGGAAGTAACATCGAGTTTGACAAATAGGAGATATACAGAGA    6120
  E D W S M K E V T S S L T N R R Y T E K
 AGTGTATAGCATATGCGGAGACCCATGATCAGgtatttaaatttatttctacaactaaa     6180
  C I A Y A E T H D Q
 taattctcagaacaattgttagatagaatccaaatatatacgtcctgaaagtataaaagt    6240 acttattttcgccatgggccttcagaatattggtagccgctgaatatcatgataagttat    6300 ttatccagtgacatttttatgttcactcctattatgtctgctggatacagTCTATTGTTG    6360
                                                    S I V G
 GTGACAAGACCATTGCATTTCTCCTAATGGACAAAGAGATGTATTCTGGCATGTCTTGCT    6420
  D K T I A F L L M D K E M Y S G M S C L
 TGACAGATGCTTCTCCTGTTGTTGATCGAGGAATTGCGCTTCACAAGgttgtctgtttc     6480
  T D A S P V V D R G I A L H K
 tattgcatttTaaggttcatataggttagccacggaaaatctcactctttgtgaggtaac    6540 cagggttctgatggattattcaatttctcgtttatcatttgtttattcttttcatgcat    6600 tgtgtttcttttcaatatccctcttatttggaggtaattttctcatctattcactttt     6660 agcttctaaccacagATGATCCATTTTTTCACAATGGCCTTGGGAGGAGAGGGGTACCTC    6720
                 M I H F F T M A L G G E G Y L
 AATTTCATGGGTAACGAGgtatgtcttacatctttagatatttgtgataattacaatta    6780
  N F M G N E
 gtttggcttacttgaacaagattcattcctcaaaatgacctgaactgttgaacatcaaag    6840 gggttgaaacatagaggaaaacaacatgatgaatgtttccattgtctagggatttctatt    6900 atgttgctgagaacaaatgtcatcttaaaaaaaacattgtttactttttgtagtataga    6960 agattactgtatagagtttgcaagtgtgtctgttttggagtaattgtgaaatgtttgatg    7020 aacttgtacagTTTGGCCATCCTGAGTGGATTGACTTCCCTAGAGAGGGCAATAATTGGA    7080
             F G H P E W I D F P R E G N N W S
 GTTATGACAAATGTAGACGCCAGTGGAACCTCGCGGATAGCGAACACTTGAGATACAAAg    7140
  Y D K C R R Q W N L A D S E H L R Y K
 ttcaagtattttgaatcgcagcttgttaaataatctagtaattttagattgcttacttg     7200 gaagtctacttggttctggggatgatagctcatttcatcttgttctacttattttccaac    7260 cgaatttctgatttttgtttcgagatccaagtattagattcattacacttattaccgcc    7320 tcatttctaccactaaggccttgatgagcagcttaagttgattctttgaagctatagttt    7380 caggctaccaatccacagcctgctatatttgttggatacttacctttttctttacaatgaa   7440 gtgatactaattgaaatggtctaaatctgatatctatatttctccgtcttttcctccccct   7500
```

FIG. 12E

```
          10        20        30        40        50        60
 1234567890123456789012345678901234567890123456789012345678901234567890
catgatgaaatgcagTTTATGAATGCATTTGATAGAGCTATGAATTCGCTCGATGAAAAG      7560
               F  M  N  A  F  D  R  A  M  N  S  L  D  E  K
TTCTCATTCCTCGCATCAGGAAAACAGATAGTAAGCAGCATGGATGATGATAATAAGgta      7620
 F  S  F  L  A  S  G  K  Q  I  V  S  S  M  D  D  D  N  K
aaatcatctaaagttgaaagtgttgggtttatgaagtgctttaattctatccaaggacaa      7680 gtagaaaccttttttaccttccatttcttgatgatggatttcatattatttaatccaatag    7740 ctggtcaaattcggtaatagctgtactgattagttacttcactttgcagGTTGTTGTGTT     7800
                                                 V  V  V  F
TGAACGTGGTGACCTGGTATTTGTATTCAACTTCCACCCAAAGAACACATACGAAGGgta     7860
 E  R  G  D  L  V  F  V  F  N  F  H  P  K  N  T  Y  E  G
tatatgttttacttatccatgaaattattgctctgcttgttttaatgtactgaacaagt      7920 tttatggagaagtaactgaaacaaatcattttcacattgtctaatttaactcttttttct    7980 gatcctcgcatgacgaaaacagGTATAAAGTTGGATGTGACTTGCCAGGGAAGTACAGAG     8040
                       Y  K  V  G  C  D  L  P  G  K  Y  R  V
TTGCACTGGACAGTGATGCTTGGGAATTTGGTGGCCATGGAAGAgtaaggatttgcttga     8100
 A  L  D  S  D  A  W  E  F  G  G  H  G  R
ataactttgataataagataacagatgtagggtacagttctctcaccaaaaagaactgt      8160 aattgtctcatccatctttagttgtataagatatccgactgtctgagttcggaagtgttt    8220 gagcctcctgccctcccctgcgttgtttagctaattcaaaaaggagaaaactgtttatt     8280 gatgatctttgtcttcatgctgacatacaatctgttctcatgacagACTGGTCATGATGT    8340
                                                T  G  H  D  V
TGACCATTTCACATCACCAGAAGGAATACCTGGAGTTCCAGAAACAAATTTCAATGGTCG    8400
 D  H  F  T  S  P  E  G  I  P  G  V  P  E  T  N  F  N  G  R
TCCAAATTCCTTCAAAGTGCTGTCTCCTGCGCGAACATGTGTGgtacagttcttgccgtg    8460
 P  N  S  F  K  V  L  S  P  A  R  T  C  V
tgacctcccttttttattgtggttttgttcatagttatttgaatgcgatagaagttaacta   8520 ttgattaccgccacaatcgccagttaagtcctctgaactactaatttgaaaggtaggaat    8580 agccgtaataaggtctacttttggcatcttactgttacaaaacaaaaggatgccaaaaaa    8640 attcttctctatcctcttttttccctaaaccagtgcatgtagcttgcacctgcataaactt   8700 aggtaaatgatcaaaaatgaagttgatgggaacttaaaaccgccctgaagtaaagctagg    8760 aatagtcatataatgtccacctttggtgtctgcgctaacatcaacaacaacatacctcgt    8820 gtagtcccacaaagtggtttcaggggagggtagagtgtatgcaaaacttactcctatct     8880 cagaggtagagaggattttttcaatagacccttggctcaagaaaaaaagtccaaaagaa     8940 gtaacagaagtgaaagcaacatgtgtagctaaagcgacccaacttgtttgggactgaagt    9000
```

FIG. 12F

```
              10        20        30        40        50        60
     1234567890123456789012345678901234567890123456789012345678901234567890
    agttgttgttgttgaaacagtgcatgtagatgaacacatgtcagaaatggacaacacag           9060 ttatttgtgcaagtcaaaaaaatgtactactatttcttgtgcagctttatgtatagaa            9120 aagttaaataactaatgaattttgctagcagaaaaatagcttggagagaaatttttata           9180 ttgaactaagctaactatattcatctttctttttgcttcttcttctccttgtttgtgaag          9240

GCTTATTACAGAGTTGATGAACGCATGTCAGAAACTGAAGATTACCAGACAGACATTTGT          9300
     A  Y  Y  R  V  D  E  R  M  S  E  T  E  D  Y  Q  T  D  I  C
    AGTGAGCTACTACCAACAGCCAATATCGAGGAGAGTGACGAGAAACTTAAAGATTCGTTA          9360
     S  E  L  L  P  T  A  N  I  E  E  S  D  E  K  L  K  D  S  L
    TCTACAAATATCAGTAACATTGACGAACGCATGTCAGAAACTGAAGTTTACCAGACAGAC         9420
     S  T  N  I  S  N  I  D  E  R  M  S  E  T  E  V  Y  Q  T  D
    ATTTCTAGTGAGCTACTACCAACAGCCAATATTGAGGAGAGTGACGAGAAACTTAAAGAT         9480
     I  S  S  E  L  L  P  T  A  N  I  E  E  S  D  E  K  L  K  D
    TCGTTATCTACAAATATCAGTAACATTGATCAGACTGTTGTAGTTTCTGTTGAGGAGAGA         9540
     S  L  S  T  N  I  S  N  I  D  Q  T  V  V  V  S  V  E  E  R
    GACAAGGAACTTAAAGATTCACCGTCTGTAAGCATCATTAGTGATGTTGTTCCAGCTGAA         9600
     D  K  E  L  K  D  S  P  S  V  S  I  I  S  D  V  V  P  A  E
    TGGGATGATTCAGATGCAAACGTCTGGGGTGAGGACTAGTCAGATGATTGATCGACCCTT        9660
     W  D  D  S  D  A  N  V  W  G  E  D
    CTACCGATTGGTGATCGCTATCCTTGCTCTCTGAGAAATAGGTGAGGCGAAACAAAAAAT        9720

AATTTGCATGATAAAAAGTCTGATTTTATGATCGCTATCCTCGCTCTCTGAGAAAGAAGC        9780

GAAACAAAGGCGACTCCTGGACTCGAATCTATAAGATAACAAAGGCGACTCCTGGGACTC       9840

GAATCTATAAGATAACAAAGGCAATTCCAAGACTTGAATCTATAAAAAATTTAGTTAAGA       9900

ATGATTAACGTCCGATCCTAATTCGAATCGAGGCATCTTACCACTCCATTGATAATTATA       9960

TAAGTCAATAAGTCATATAAWAGTATTAAAAACTAAATTGACTTGATCGGTCTATCAAAA       10020

ATMAGATMAAATTGTGTTCATATGTAACATTTTTGTTGTCACAATTAGCTTAATTACATC       10080

TTTCATGTGCAATAACAAAGAAATGATAGGAATTTAGAGATTCCAATTTTTTTGTTGCCA      10140

CAATTAACTTAATTACATCTTTCATTTGCAATAACAAAGAAATGATAGGAATTTAGAGAT      10200

CCAGTGTCAATACACAACCTAGGCCAACATCGAAAGCATAACTGTAAACTCATGCATGAA      10260

GAAATCAGTCGTAAAAATGAATAAATGCGACATAAAAACAAATTGCATGTATCATTAATG      10320

TGACTTAACTACAAGTAAAAATAAATTTAACAAATGTAACTTAACTACAAGTAAAAATAA     10380

ATTGCTTCTATCATTAACAAACAAACAGAATTAAAAAGAAAAAAACATACTAAATCTTAC     10440

CGTCATTCGATAAAAAAAAATACCAAATTCATAATGCAAGGAAAACGAAACGCGTCCTGA    10500
```

FIG. 12G

```
           10        20        30        40        50        60
  1234567890123456789012345678901234567890123456789012345678901234567890
  TCGGGTATCAACGATGAAATGGACCAGTTGGATCGACTGCCTGCACAACGTTAGGTATGC    10560
  CAAAAAAAGAACACGATCCTTTGCACCCGTTCGATGATTATCAGTATGTTCACAAAAAA     10620
  AACTTAAGTTCATCCCAGTGTACAACAGCCCCAACATCTGCCCCAAGTAACAAAAAACAA    10680
  CCAATTTATCTTATTCTTATCTGCCACAAAATAATCGGTTTCACACTATTCTCTTGTTAT    10740
  ACAAAATTGACAAGTAGGAAGGAGAGGAGTCATCCAAATAAACGGTGCACGTTCTTTGAG    10800
  AAAAGTCTTATTTTTCGTAAGATCCAATTTCAACAAACTTTTCTTCAAGTCAAAATTCCT    10860
  GATAGTGTATCTCCTCTCGACGACCTCTTGCATTGAACGATCTCCGCTTATCATGAAAAG    10920
  TTGCTTGGATAACAAGTATTGCAAGGGGGGACAGTAGCTATTAAGTTAGTCGGCCCAAG     10980
  GAAATGGAGGAGTGATAGTCTCGAATATTATTCACCTCTTTAGCATTACCCGGTCTGGCT    11040
  TTAAGGAGTTACGTCTTTTACGCTCGCCAATTTCTTTTTTTAGAATGGTTGGTGTCAAAA    11100
  TCGCGAGTTGTGGAAGGTTCAAGTTACTCGATTCGTGATTTTCAAGTATGAGTGGTGAGA    11160
  GAGATTCGATATTTTCACGAGGTGTATTCGAGGTCTAGTAGAACGAAGGGTGTCACTAAT    11220
  GAAAGTTTCAAGAGTTCATCATCATCTTCTTCTAGTAGATTTTCGCTTTCAAATGAGTAT    11280
  GAAAATTCTTCCTCTTTTCTATTGATTTTCTTCATTGTTTTCTTCATTGTTGTGGTTGTT    11340
  ATTGAAAAGAAAGAAAATTTATAACAGAAAAGATGTCAAAAAAAGGTAAAATGAAAGA     11400
  GTATCATATACTTAAAGAGTTGCGTAGAGATAAGTCAAAAGAAACAGAATTATAGTAATT   11460
  TCAGCTAAGTTAGAATTC
                                                                  11478
```

GTATACACTCTCTGGAGTTCGTTTTCCTACTGTTCCATCAGTGTACAAATCTAATGGATT              60
      Y  T  L  S  G  V  R  F  P  T  V  P  S  V  Y  K  S  N  G  F

SspI
                                    BsmI
     CAGCAGTAATGGTGATCGGAGGAATGCTAATATTTCTGTATTCTTGAAAAAACACTCTCT             120
      S  S  N  G  D  R  R  N  A  N  I  S  V  F  L  K  K  H  S  L

BsaAI
     TTCACgtatgtctcactgtgtttgtggctgtgtgtgtttttttctctgtcttttttgtgtt            180
      S  R Bsp1286I
                          BanII
     ttgtgtaattggggctctttaaagttggtattgtgtataccttttgagtatagtctttg              240 aggaagcaaaatgatgaatcttgattgacattagtaaggggttgtaacttttttgaagtttg           300 gttaggtgtaattgagtttggcttgtgtgtctgtgtgtcgaggttattttttttggtttgt            360 gttattggggatcttaaaagttggtattgtgtataccttttgagtatagtctttgagga             420 agcaaaaatgatgaatcttgattggcattagtaaaggttgtagcttttttgaagtgtggtt           480 aggtgtaattgagtttggcttgtgtgtctgtgtgtgttttggaatcctgatgtgtgtcaagt           540
```

FIG. 14A

```
          10        20        30        40        50        60
 1234567890123456789012345678901234567890123456789012345678901234567890
``` cctgatatgggtcgaggttctttctttggtttgtgtaattgggggttcttaaaagttggt    600

ClaI
                                       BspDI
attatgtaccttttaagaatagtgtctgagaaagcaaaatcgatgaattttgattgaca    660 gcatattctttgagaaagcaaaaaatggtgagttttcatggagaaacttgattgacatta    720 ctaaaggtagcaacttttttcaactcctgatatgggtcaaggttctttgtttggtttgtgt    780 aatttggggttctttgaagttttgagaaagaaaaattatgattttcatggagaaatttg    840

PvuII
           AseI                           NspBII
atttacattaataaaggtagtagctttttaaagtgtggtcagctgtaatgagttcagctt    900

Bsp1286I
         BanII
         ApaI   NdeI
ggtttaaaggggcccctacatatggtgctttctggtgagatatttgttgctccaccatac    960 gagttataagaatcatagtgttaggatcttttttctttttttttcattttcacttgac   1020 tagctactagaggagtgatcttgacggcggaaaatcttagaaaggggaaggttgtttgca   1080

```
                    Esp3I              BsaBI
                      ▼                  ▼
         tcaactggtgttatatgtgcaaggagacgggagatgatgtagatcatcttcttcttcatt    1140 gtggtctttccatgaggttatgatgtgatatgtttgaatggtttggtacttcttggctat    1200

EarI
                                               ▼
         gccaagaactgtgaaagaattgatattcagttggaagtgtggagttggaagagtggaaga    1260 attgacacttggttccattagctttaatgtgggtggtgtggagagagagagaaataggag    1320

EcoRV
                                                          ▼
         agcttttgagggggtagagttgagctttcctcagttgagaagtagcctttgatatctttt    1380

EcoRI   MunI
                            ▼      ▼
         ttttttttttttgtacacccatagaattcccaattgtatagaagattgggtggagtttgt    1440 agagaatcatcttttgtagtagattctttaccttttggtatatccattgtatacagccag    1500

StuI
           ▼
         gcctttgactatgtttatgaatgaatatacattacttgaaaaaaaaagaagtgaagccag    1560 tctgttgtacctttgtagacaatgttgttgcagcatcttgataattccctgaaaattgtc    1620
```

FIG. 14C

```
          10        20        30        40        50        60
 1234567890123456789012345678901234567890123456789012345678901234567890 tccctgaaggaatagtttggttgatattgattatttcttggtttgtttaattcggtgttc      1680 ttgaaggccatttttaaatcctttgacattgttaaaggtgtttacaagtgttggtctgggt     1740 ttaaaagcacctcttgtatggtgctttctggagtgatctttcttcctccaaaagagaagt     1800

BclI BglII
tgcaagaatcagtgtgtgtactttttttctcttgtatgatcagatcttttttcaatttttc    1860 cgttttagttgatttatccatatagtgaaagttggtgtcatagttgctgtttgtggactt     1920 cctgtaaaagttttttgatatacttaaaaaattgtcacacagaagaaagagttttttacc    1980

AflII
attacttaagctagatgggactgtttgattcttagaccaaataatgaacctttttgttct     2040

AflIII
cttaacgtgtacttgaaatagtttggtaaaattgtgataggaaaaaagataattcttgat    2100

EarI
tgcttttggagcatcacttctaatcataaaagtctttgctctcttcaaccatgaatgata     2160
```

FIG. 14D

```
          10        20        30        40        50        60
 1234567890123456789012345678901234567890123456789012345678901234567890
``` aattggacacttatgtggccctaagttgctctcagtagtggtcttttaattgtggagatat    2220

```
                           BglII     BbsI
aactaatctgatatatgtatgtagGGAAGATCTTGGCTGAAAAGTCTTCTTACAATTCCG      2280
                         K  I  L  A  E  K  S  S  Y  N  S  E
```

```
         SfcI
AATCCCGACCTTCTACAGTTGCAGCATCG                                     2309
 S  R  P  S  T  V  A  A  S
```

ANTISENSE INTRON INHIBITION OF STARCH BRANCHING ENZYME EXPRESSION

CROSS-REFERENCE TO RELATED APPLICATIONS

This application is a national stage filing of PCT/IB98/00270, filed on Feb. 23, 1998, under 35 U.S.C. §371.

FIELD OF THE INVENTION

The present invention relates to a method of inhibiting gene expression, particularly inhibiting gene expression in a plant. The present invention also relates to a nucleotide sequence useful in the method. In addition, the present invention relates to a promoter that is useful for expressing the nucleotide sequence.

Starch is one of the main storage carbohydrates in plants, especially higher plants. The structure of starch consists of amylose and amylopectin. Amylose consists essentially of straight chains of α-1-4-linked glycosyl residues. Amylopectin comprises chains of α-1-4-linked glycosyl residues with some α-1-6 branches. The branched nature of amylopectin is accomplished by the action of inter alia an enzyme commonly known as the starch branching enzyme ("SBE"). SBE catalyses the formation of branch points in the amylopectin molecule by adding α-1,4 glucans through α-1,6-glucosidic branching linkages. The biosynthesis of amylose and amylopectin is schematically shown in FIG. 1, whereas the α-1-4-links and the α-1-6 links are shown in FIG. 2.

In Potato, it is known that two classes of SBE exist. In our copending international patent applications PCT/EP96/03052 and PCT/EP96/03053, class B potato SBE and a gene encoding it are discussed. In international patent application WO96/34968, class A potato SBE and a cDNA encoding it are disclosed.

It is known that starch is an important raw material. Starch is widely used in the food, paper. and chemical industries. However, a large fraction of the starches used in these industrial applications are post-harvest modified by chemical, physical or enzymatic methods in order to obtain starches with certain required functional properties.

Within the past few years it has become desirable to make genetically modified plants which could be capable of producing modified starches which could be the same as the post-harvest modified starches. It is also known that it may be possible to prepare such genetically modified plants by expression of antisense nucleotide coding sequences. In this regard, June Bourque provides a detailed sunmmary of antisense strategies for the genetic nanipulations in plants (Bourque 1995 Plant Science 105 pp 125–149). At this stage, reference could be made to FIG. 3 which is a schematic diagram of one of the proposed mechanisms of antisense-RNA inhibition.

In particular, WO 92/11375 reports on a method of genetically modifying potato so as to form amylose-type starch. The method involves the use of an anti-sense construct that can apparently inhibit, to a varying extent, the expression of the gene coding for formation of the branching enzyme in potato. The antisense construct of WO 92/11375 consists of a tuber specific promoter, a transcription start sequence and the first exon of the branching. enzyme in antisense direction. However, WO 92/11375 does not provide any antisense sequence data. In addition, WO 92/11375 only discloses the use of the potato GBSS promoter.

WO 92/14827 reports on a plasmid that, after insertion into the genome of a plant, can apparently cause changes in the carbohydrate concentration and carbohydrate composition. such as the concentration and composition of amylose and amylopectin, in the regenerated plant. The plasmid contains part of the coding sequence of a branching enzyme in an antisense orientation.

EP-A-0647715 reports on the use of antisense endogenous mRNA coding DNA to alter the characteristics and the metabolic pathways of ornamental plants.

EP-A-0467349 reports on the expression of sequences that are antisense to sequences upstream of a promoter to control gene expression.

EP-A-0458367 and U.S. Pat. No. 5,107,065 report on the expression of a nucleotide sequence to regulate gene expression in a plant. The nucleotide sequence is complementary to a mRNA sequence of a gene and may cover all or a portion of the noncoding region of the gene. In other words, the nucleotide sequences of EP-A-0458367 and U.S. Pat. No. 5,107,065 must at least comprise a sequence that is complementary to a coding region. EP-A-0458367 and U.S. Pat. No. 5,107,065 contain minimal sequence information.

WO96/34968 discusses the use of antisense sequences complementary to sequences which encode class A and class B potato SBE to downregulate SBE expression in potato plants. The sequences used are complementary to SBE coding sequences.

Kuipers et al in Mol. Gen. Genet. [1995]246 745–755 report on the expression of a series of nucleotides that are antisense to part of the genomic intron sequences of potato granule bound starch synthetase. Here the antisense intron sequences are attached to a part of the antisense exon sequences—wherein the intron sequences and the exon sequences are naturally associated with each other. In addition, the expressed antisense intron sequences are at most 231 bp in length.

Likewise, Kull et al in J. Genet & Breed. [1995] 49 69–76 report on the expression of a series of nucleotides that are antisense to part of the genomic intron sequences of potato granule bound starch synthetase. Likewise, here the antisense intron sequences are attached to a part of the antisense exon sequences—wherein the intron sequences and the exon sequences are naturally associated with each other. In addition, likewise, the expressed antisense intron sequences are at most 231 bp in length.

Shimada et al in Theor. Appl. Genet. [1993]86 665–672 report on the expression of a series of nucleotides that are antisense to part of the genomic intron sequences of rice granule bound starch synthetase. Here the antisense intron sequences are attached to a part of the antisense exon sequences—wherein the intron sequences and the exon sequences are naturally associated with each other. In addition, the expressed antisense intron sequences are less than 350 bp in length.

Reviews on how enzymatic activity can be affected by expression of particular nucleotide sequences may be found in the teachings of Finnegan and McElroy [1994] Biotechnology 12 883–888; and Matzke and Matzke [1995] TIG 11 1–3.

Whilst it is known that enzymatic activity can be affected by expression of particular nucleotide sequences there is still a need for a method that can more reliably and/or more efficiently and/or more specifically affect enzymatic activity.

SUMMARY OF THE INVENTION

According to a first aspect of the present invention there is provided a method of affecting enzymatic activity in a plant (or a cell, a tissue or an organ thereof) comprising expressing in the plant (or a cell, a tissue or an organ thereof) a nucleotide sequence wherein the nucleotide sequence partially or completely codes for (is) an intron of the potato class A SBE gene in an antisense orientation optionally together with a nucleotide sequence which codes, partially or completely, for an intron of a class B starch branching enzyme in an antisense or sense orientation; and wherein the nucleotide sequence does not contain a sequence that is antisense to an exon sequence normally associated with the intron.

According to a second aspect of the present invention there is provided a method of affecting enzymatic activity in a starch producing organism (or a cell, a tissue or an organ thereof) comprising expressing in the starch producing organism (or a cell, a tissue or an organ thereof) a nucleotide sequence wherein the nucleotide sequence codes, partially or completely, for an intron of the potato class A SBE gene, in an antisense orientation optionally together with a nucleotide sequence which codes, partially or completely, for an intron of a class B starch branching enzyme in an antisense or sense orientation; and wherein starch branching enzyme activity is affected and/or the levels of amylopectin are affected and/or the composition of starch is changed.

Preferably, the class A SBE gene antisense intron construct is used in combination with a potato class B SBE gene antisense intron construct as defined in PCT/EP96/03052. However, it may also be used independently thereof, to target class A SBE alone, or in combination with other transgenes, to further manipulate starch quality in potato plants.

According to a third aspect of the present invention, therefore. there is provided an antisense sequence comprising the nucleotide sequence shown as any one of SEQ.I.D. No. 15 to SEQ.I.D. No. 27 and the complement of SEQ. ID. No.38, or a variant, derivative or homologue thereof.

According to a fourth aspect of the present invention there is provided a promoter comprising the sequence shown as SEQ.I.D. No. 14 or a variant, derivative or homologue thereof.

According to a fifth aspect of the present invention there is provided a construct capable of comprising or expressing the present invention.

According to a sixth aspect of the present invention there is provided a vector comprising or expressing the present invention.

According to a seventh aspect of the present invention there is provided a cell, tissue or organ comprising or expressing the present invention.

According to an eighth aspect of the present invention there is provided a transgenic starch producing organism comprising or expressing the present invention.

According to a ninth aspect of the present invention there is provided a starch obtained from the present invention.

According to a tenth aspect of the present invention there is provided pSS17 and pSS18.

According to an eleventh aspect of the present invention there is provided a nucleotide sequence that is antisense to any one or more of the intron sequences obtainable from class A SBE, and especially those obtainable from intron of class A SBE as set forth in SEQ. ID. No. 38.

A key advantage of the present invention is that it provides a method for preparing modified starches that is not dependent on the need for post-harvest modification of starches. Thus the method of the present invention obviates the need for the use of hazardous chemicals that are normally used in the post-harvest modification of starches.

In addition, the present invention provides inter alia genetically modified plants which are capable of producing modified and/or novel and/or improved starches whose properties would satisfy various industrial requirements.

Thus, the present invention provides a method of preparing tailor-made starches in plants which could replace the post-harvest modified starches.

Also, the present invention provides a method that enables modified starches to be prepared by a method that can have a more beneficial effect on the environment than the known post-harvest modification methods which are dependent on the use of hazardous chemicals and large quantities of energy.

An other key advantage of the present invention is that it provides a method that may more reliably and/or more efficiently and/or more specifically affect enzymatic activity when compared to the known methods of affecting enzymatic activity. With regard to this advantage of the present invention it is to be noted that there is some degree of homology between coding regions of SBEs. However, there is little or no homology with the intron sequences of SBEs.

Thus, antisense intron expression provides a mechanism to affect selectively the expression of a particular class A SBE. This advantageous aspect could be used, for example, to reduce or eliminate a particular SBE enzyme, especially a class A SBE enzyme, and replace that enzyme with another enzyme which can be another branching enzyme or even a recombinant version of the affected enzyme or even a hybrid enzyme which could for example comprise part of a SBE enzyme from one source and at least a part of another SBE enzyme from another source. This particular feature of the present invention is covered by the combination aspect of the present invention which is discussed in more detail later.

Thus the present invention provides a mechanism for selectively affecting class A SBE activity. This is in contrast to the prior art methods which are dependent on the use of for example antisense exon expression whereby it would not be possible to introduce new SBE activity without affecting that activity as well.

In the context of the present invention, class B SBE is synonymous with SBE I: class A SBE is synonymous with SBE II. Class A SBE is as defined in WO96/34968, incorporated herein by reference. Preferably, the antisense intron construct used comprises intron 1 of class A SBE, which is 2.0 kb in length and is located starting at residue 45 of the coding sequence of class A SEE. The boundaries of the intron may be calculated by searching for consensus intron boundary sequences. and are shown in attached FIG. 13. Class B SBE is substantially as defined in the sequences given herein and in PCT/EP96/03052.

Preferably with the first aspect of the present invention starch branching enzyme activity is affected and/or the levels of amylopectin are affected and/or the composition of starch is changed.

Preferably with the second aspect of the present invention the nucleotide sequence does not contain a sequence that is antisense to an exon sequence normally associated with the intron.

Preferably with the fourth aspect of the present invention the promoter is in combination with a gene of interest ("GOI").

Preferably the enzymatic activity is reduced or eliminated.

Preferably the nucleotide sequence codes for at least substantially all of at least one intron in an antisense orientation.

Preferably the nucleotide sequence codes, partially or completely, for two or more introns and wherein each intron is in an anti-sense orientation.

Preferably the nucleotide sequence comprises at least 350 nucleotides (e.g. at least 350 bp), more preferably at least 500 nucleotides (e.g. at least 500 bp).

Preferably the nucleotide sequence comprises the complement of the sequence shown in SEQ. ID. No. 38, or a fragment thereof.

Preferably the nucleotide sequence is expressed by a promoter having a sequence shown as SEQ. I.D. No 14 or a variant, derivative or homologue thereof.

Preferably the transgenic starch producing organism is a plant.

A preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; and wherein starch branching enzyme activity is affected and/or the levels of amylopectin are affected and/or the composition of starch is changed.

A more preferred aspect of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; wherein starch branching enzyme activity is affected and/or the levels of amylopectin are affected and/or the composition of starch is changed; and wherein the nucleotide sequence comprises the sequence shown as any one of SEQ.I.D. No. 15 to SEQ.I.D. No. 27 or a variant, derivative or homologue thereof, including combinations thereof.

The term "nucleotide" in relation to the present invention includes DNA and RNA. Preferably it means DNA, more preferably DNA prepared by use of recombinant DNA techniques.

The term "intron" is used in its normal sense as meaning a segment of nucleotides, usually DNA, that is transcribed but does not encode part or all of an expressed protein or enzyme.

The term "exon" is used in its normal sense as meaning a segment of nucleotides, usually DNA, encoding part or all of an expressed protein or enzyme.

Thus, the term "intron" refers to gene regions that are transcribed into RNA molecules, but which are spliced out of the RNA before the RNA is translated into a protein. In contrast, the term "exon" refers to gene regions that are transcribed into RNA and subsequently translated into proteins.

The terms "variant" or "homologue" or "fragment" in relation to the nucleotide sequence of the present invention include any substitution of, variation of, modification of, replacement of, deletion of or addition of one (or more) nucleic acid from or to the respective nucleotide sequence providing the resultant nucleotide sequence can affect enzyme activity in a plant, or cell or tissue thereof, preferably wherein the resultant nucleotide sequence has at least the same effect as the complement of the sequence shown as SEQ.I.D. No. 38. In particular, the term "homologue" covers homology with respect to similarity of structure and/or similarity of function providing the resultant nucleotide sequence has the ability to affect enzymatic activity in accordance with the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

Likewise, the terms "variant" or "homologue" or "fragment" in relation to the promoter of the present invention include any substitution of, variation of, modification of, replacement of, deletion of or addition of one (or more) nucleic acid from or to the respective promoter sequence providing the resultant promoter sequence allows expression of a GOI, preferably wherein the resultant promoter sequence has at least the same effect as SEQ.I.D. No. 14. In particular, the term "homologue" covers homology with respect to similarity of structure and/or similarity of function providing the resultant promoter sequence has the ability to allow for expression of a GOI, such as a nucleotide sequence according to the present invention. With respect to sequence homology (i.e. similarity), preferably there is more than 80% homology, more preferably at least 85% homology, more preferably at least 90% homology, even more preferably at least 95% homology, more preferably at least 98% homology. The above terms are also synonymous with allelic variations of the sequences.

The term "antisense" means a nucleotide sequence that is complementary to, and can therefore hybridise with, any one or all of the intron sequences of the present invention, including partial sequences thereof.

With the present invention, the antisense intron can be complementary to an entire intron of the gene to be inhibited. However, in some circumstances, partial antisense sequences may be used (i.e. sequences that are not or do not comprise the full complementary sequence) providing the partial sequences affect enzymatic activity. Suitable examples of partial sequences include sequences that are shorter than the full complement of SEQ. ID. No. 38 but which comprise nucleotides that are at least antisense to the sense intron sequences adjacent the respective exon or exons.

With regard to the second aspect of the present invention (i.e. specifically affecting SBE activity), the nucleotide sequences of the present invention may comprise one or more sense or antisense exon sequences of the SBE gene, including complete or partial sequences thereof, providing the nucleotide sequences can affect SBE activity, preferably wherein the nucleotide sequences reduce or eliminate SBE activity. Preferably, the nucleotide sequence of the second aspect of the present invention does not comprise an antisense exon sequence.

The term "vector" includes an expression vector and a transformation vector. The term "expression vector" means a construct capable of in vivo or in vitro expression. The term "transformation vector" means a construct capable of being transferred from one species to another—such as from an E. Coli plasmid to a fungus or a plant cell, or from an Agrobacterium to a plant cell.

The term "construct"—which is synonymous with terms such as "conjugate", "cassette" and "hybrid"—in relation to the antisense nucleotide sequence aspect of the present invention includes the nucleotide sequence according to the present invention directly or indirectly attached to a promoter. An example of an indirect attachment is the provision of a suitable spacer group such as an intron sequence, such as the Shl-intron or the ADH intron, intermediate the promoter and the nucleotide sequence of the present invention. The same is true for the term "fused" in relation to the present invention which includes direct or indirect attachment. The terms do not cover the natural combination of the wild type SBE gene when associated with the wild type SBE gene promoter in their natural environment.

The construct may even contain or express a marker which allows for the selection of the genetic construct in, for example, a plant cell into which it has been transferred. Various markers exist which may be used in, for example, plants—such as mannose. Other examples of markers include those that provide for antibiotic resistance—e.g. resistance to G418, hygromycin, bleomycin, kanamycin and gentamycin.

The construct of the present invention preferably comprises a promoter. The term "promoter" is used in the normal sense of the art, e.g. an RNA polymerase binding site in the Jacob-Monod theory of gene expression. Examples of suitable promoters are those that can direct efficient expression of the nucleotide sequence of the present invention and/or in a specific type of cell. Some examples of tissue specific promoters are disclosed in WO 92/11375.

The promoter could additionally include conserved regions such as a Pribnow Box or a TATA box. The promoters may even contain other sequences to affect (such as to maintain, enhance, decrease) the levels of expression of the nucleotide sequence of the present invention. Suitable examples of such sequences include the Shl-intron or an ADH intron. Other sequences include inducible elements—such as temperature, chemical, light or stress inducible elements. Also, suitable elements to enhance transcription or translation may be present. An example of the latter element is the TMV 5' leader sequence (see Sleat Gene 217 [1987] 217–225; and Dawson Plant Mol. Biol. 23 [1993] 97).

As mentioned, the construct and/or the vector of the present invention may include a transcriptional initiation region which may provide for regulated or constitutive expression. Any suitable promoter may be used for the transcriptional initiation region, such as a tissue specific promoter. In one aspect, preferably the promoter is the patatin promoter or the E35S promoter. In another aspect, preferably the promoter is the SBE promoter.

If, for example, the organism is a plant then the promoter can be one that affects expression of the nucleotide sequence in any one or more of seed, tuber, stem, sprout, root and leaf tissues, preferably tuber. By way of example, the promoter for the nucleotide sequence of the present invention can be the α-Amy 1 promoter (otherwise known as the Amy 1 promoter, the Amy 637 promoter or the α-Amy 637 promoter) as described in our co-pending UK patent application No. 9421292.5 filed Oct. 21, 1994. Alternatively, the promoter for the nucleotide sequence of the present invention can be the α-Amy 3 promoter (otherwise known as the Amy 3 promoter, the Amy 351 promoter or the α-Amy 351 promoter) as described in our co-pending UK patent application No. 9421286.7 filed Oct. 21, 1994.

The present invention also encompasses the use of a promoter to express a nucleotide sequence according to the present invention, wherein a part of the promoter is inactivated but wherein the promoter can still function as a promoter. Partial inactivation of a promoter in some instances is advantageous. In particular, with the Amy 351 promoter mentioned earlier it is possible to inactivate a part of it so that the partially inactivated promoter expresses the nucleotide sequence of the present invention in a more specific manner such as in just one specific tissue type or organ. The term "inactivated" means partial inactivation in the sense that the expression pattern of the promoter is modified but wherein the partially inactivated promoter still functions as a promoter. However, as mentioned above, the modified promoter is capable of expressing a gene coding for the enzyme of the present invention in at least one (but not all) specific tissue of the original promoter. Examples of partial inactivation include altering the folding pattern of the promoter sequence, or binding species to parts of the nucleotide sequence, so that a part of the nucleotide sequence is not recognised by, for example, RNA polymerase. Another, and preferable, way of partially inactivating the promoter is to truncate it to form fragments thereof. Another way would be to mutate at least a part of the sequence so that the RNA polymerase can not bind to that part or another part. Another modification is to mutate the binding sites for regulatory proteins for example the CreA protein known from filamentous fungi to exert carbon catabolite repression, and thus abolish the catabolite repression of the native promoter.

The construct and/or the vector of the present invention may include a transcriptional termination region.

The nucleotide according to the present invention can be expressed in combination (but not necessarily at the same time) with an additional construct. Thus the present invention also provides a combination of constructs comprising a first construct comprising the nucleotide sequence according to the present invention operatively linked to a first promoter; and a second construct comprising a GOI operatively linked to a second promoter (which need not be the same as the first promoter). With this aspect of the present invention the combination of constructs may be present in the same vector, plasmid, cells, tissue, organ or organism. This aspect of the present invention also covers methods of expressing the same, preferably in specific cells or tissues, such as expression in just a specific cell or tissue, of an organism, typically a plant. With this aspect of the present invention the second construct does not cover the natural combination of the gene coding for an enzyme ordinarily associated with the wild type gene promoter when they are both in their natural environment.

An example of a suitable combination would be a first construct comprising the nucleotide sequence of the present invention and a promoter, such as the promoter of the present invention, and a second construct comprising a promoter, such as the promoter of the present invention, and a GOI wherein the GOI codes for another starch branching enzyme either in sense or antisense orientation.

The above comments relating to the term "construct" for the antisense nucleotide aspect of the present invention are equally applicable to the term "construct" for the promoter aspect of the present invention. In this regard, the term includes the promoter according to the present invention directly or indirectly attached to a GOI.

The term "GOI" with reference to the promoter aspect of the present invention or the combination aspect of the present invention means any gene of interest, which need not necessarily code for a protein or an enzyme—as is explained later. A GOI can be any nucleotide sequence that is either foreign or natural to the organism in question, for example a plant.

Typical examples of a GOI include genes encoding for other proteins or enzymes that modify metabolic and catabolic processes. The GOI may code for an agent for introducing or increasing pathogen resistance.

The GOI may even be an antisense construct for modifying the expression of natural transcripts present in the relevant tissues. An example of such a GOI is the nucleotide sequence according to the present invention.

The GOI may even code for a protein that is non-natural to the host organism—e.g. a plant. The GOI may code for a compound that is of benefit to animals or humans. For example, the GOI could code for a pharmaceutically active protein or enzyme such as any one of the therapeutic compounds insulin, interferon, human serum albumin, human growth factor and blood clotting factors. The GOI may even code for a protein giving additional nutritional value to a food or feed or crop. Typical examples include plant proteins that can inhibit the formation of anti-nutritive factors and plant proteins that have a more desirable amino acid composition (e.g. a higher lysine content than a non-transgenic plant). The GOI may even code for an enzyme that can be used in food processing such as xylanases and α-galactosidase. The GOI can be a gene encoding for any one of a pest toxin, an antisense transcript such as that for α-amylase, a protease or a glucanase. Alternatively, the GOI can be a nucleotide sequence according to the present invention.

The GOI can be the nucleotide sequence coding for the arabinofuranosidase enzyme which is the subject of our co-pending UK patent application 9505479.7. The GOI can be the nucleotide sequence coding for the glucanase enzyme which is the subject of our co-pending UK patent application 9505475.5. The GOI can be the nucleotide sequence coding for the α-amylase enzyme which is the subject of our co-pending UK patent application 9413439.2. The GOI can be the nucleotide sequence coding for the α-amylase enzyme which is the subject of our co-pending UK patent application 9421290.9. The GOI can be any of the nucleotide sequences coding for the a-glucan lyase enzyme which are described in our co-pending PCT patent application PCT/EP94/03397.

In one aspect the GOI can even be a nucleotide sequence according to the present invention but when operatively linked to a different promoter.

The GOI could include a sequence that codes for one or more of a xylanase, an arabinase, an acetyl esterase, a rhamnogalacturonase, a glucanase, a pectinase, a branching enzyme or another carbohydrate modifying enzyme or proteinase. Alternatively, the GOI may be a sequence that is antisense to any of those sequences.

As mentioned above, the present invention provides a mechanism for selectively affecting a particular enzymatic activity. In an important application of the present invention it is now possible to reduce or eliminate expression of a genomic nucleotide sequence coding for a genomic protein or enzyme by expressing an antisense intron construct for that particular genomic protein or enzyme and (e.g. at the same time) expressing a recombinant version of that enzyme or protein—in other words the GOI is a recombinant nucleotide sequence coding for the genomic enzyme or protein. This application allows expression of desired recombinant enzymes and proteins in the absence of (or reduced levels of) respective genomic enzymes and proteins. Thus the desired recombinant enzymes and proteins can be easily separated and purified from the host organism. This particular aspect of the present invention is very advantageous over the prior art methods which, for example, rely on the use of anti-sense exon expression which methods also affect expression of the recombinant enzyme.

Thus, a further aspect of the present invention relates to a method of expressing a recombinant protein or enzyme in a host organism comprising expressing a nucleotide sequence coding for the recombinant protein or enzyme; and expressing a further nucleotide sequence wherein the further nucleotide sequence codes, partially or completely, for an intron in an antisense orientation; wherein the intron is an intron normally associated with the genomic gene encoding a protein or an enzyme corresponding to the recombinant protein or enzyme; and wherein the further nucleotide sequence does not contain a sequence that is antisense to an exon sequence normally associated with the intron. Additional aspects cover the combination of those nucleotide sequences including their incorporation in constructs, vectors, cells, tissues and transgenic organisms.

Therefore the present invention also relates to a combination of nucleotide sequences comprising a first nucleotide sequence coding for a recombinant enzyme; and a second nucleotide sequence which corresponds to an intron in antisense orientation. wherein the intron is an intron that is associated with a genomic gene encoding an enzyme corresponding to the recombinant enzyme; and wherein the second nucleotide sequence does not contain a sequence that is antisense to an exon sequence normally associated with the intron.

The GOI may even code for one or more introns, such as any one or more of the intron sequences presented in the attached sequence listings. For example, the present invention also covers the expression of for example an antisense intron (e.g. the complement of SEQ. ID. No. 38) in combination with for example a sense intron which preferably is not complementary to the antisense intron sequence (e.g. SEQ.I.D.No. 2 or another class A SBE intron).

The terms "cell", "tissue" and "organ" include cell, tissue and organ per se and when within an organism.

The term "organism" in relation to the present invention includes any organism that could comprise the nucleotide sequence according to the present invention and/or wherein the nucleotide sequence according to the present invention can be expressed when present in the organism. Preferably the organism is a starch producing organism such as any one of a plant, algae, fungi, yeast and bacteria, as well as cell lines thereof. Preferably the organism is a plant.

The term "starch producing organism" includes any organism that can biosynthesise starch. Preferably, the starch producing organism is a plant.

The term "plant" as used herein includes any suitable angiosperm, gymnosperm, monocotyledon and dicotyledon. Typical examples of suitable plants include vegetables such as potatoes; cereals such as wheat, maize, and barley; fruit; trees; flowers; and other plant crops. Preferably, the term means "potato".

The term "transgenic organism" in relation to the present invention includes any organism that comprises the nucleotide sequence according to the present invention and/or products obtained therefrom, and/or wherein the nucleotide sequence according to the present invention can be expressed within the organism. Preferably the nucleotide sequence of the present invention is incorporated in the genome of the organism. Preferably the transgenic organism is a plant, more preferably a potato.

To prepare the host organism one can use prokaryotic or eukaryotic organisms. Examples of suitable prokaryotic hosts include *E. coli* and *Bacillus subtilis*. Teachings on the transformation of prokaryotic hosts is well documented in the art, for example see Sambrook et al (Sambrook et al. in Molecular Cloning: A Laboratory Manual, 2nd edition, 1989, Cold Spring Harbor Laboratory Press).

Even though the enzyme according to the present invention and the nucleotide sequence coding for same are not disclosed in EP-B-0470145 and CA-A-2006454, those two documents do provide some useful background commentary on the types of techniques that may be employed to prepare transgenic plants according to the present invention. Some of these background teachings are now included in the following commentary.

The basic principle in the construction of genetically modified plants is to insert genetic information in the plant genome so as to obtain a stable maintenance of the inserted genetic material.

Several techniques exist for inserting the genetic information. the two main principles being direct introduction of the genetic information and introduction of the genetic information by use of a vector system. A review of the general techniques may be found in articles by Potrykus (Annu Rev Plant Physiol Plant Mol Biol [1991]42:205–225) and Christou (Agro-Food-Industry Hi-Tech March/April 1994 17–27).

Thus, in one aspect, the present invention relates to a vector system which carries a nucleotide sequence or construct according to the present invention and which is capable of introducing the nucleotide sequence or construct into the genome of an organism, such as a plant.

The vector system may comprise one vector, but it can comprise two vectors. In the case of two vectors, the vector system is normally referred to as a binary vector system. Binary vector systems are described in further detail in Gynheuna An et al. (1980), Binary Vectors, *Plant Molecular Biology Manual A*3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* An et al. (1986), *Plant Physiol*. 81, 301–305 and Butcher D. N. et al. (1980), *Tissue Culture Methods for Plant Pathologists*, eds.: D. S. Ingrams and J. P. Helgeson, 203–208. Several different Ti and Ri plasmids have been constructed which are suitable for the construction of the plant or plant cell constructs described above. A non-limiting example of such a Ti plasmid is pGV3850.

The nucleotide sequence or construct of the present invention should preferably be inserted into the Ti-plasmid between the terminal sequences of the T-DNA or adjacent a T-DNA sequence so as to avoid disruption of the sequences immediately surrounding the T-DNA borders, as at least one of these regions appears to be essential for insertion of modified T-DNA into the plant genome.

As will be understood from the above explanation, if the organism is a plant the vector system of the present invention is preferably one which contains the sequences necessary to infect the plant (e.g. the vir region) and at least one border part of a T-DNA sequence, the border part being located on the same vector as the genetic construct.

Furthermore, the vector system is preferably an *Agrobacterium tumefaciens* Ti-plasmid or an *Agrobacterium rhizogenes* Ri-plasmid or a derivative thereof. As these plasmids are well-known and widely employed in the construction of transgenic plants, many vector systems exist which are based on these plasmids or derivatives thereof.

In the construction of a transgenic plant the nucleotide sequence or construct of the present invention may be first constructed in a microorganism in which the vector can replicate and which is easy to manipulate before insertion into the plant. An example of a useful microorganism is *E. coli*, but other microorganisms having the above properties may be used. When a vector of a vector system as defined above has been constructed in *E. coli*, it is transferred, if necessary, into a suitable Agrobacterium strain, e.g. *Agrobacteriun tumefaciens*. The Ti-plasmid harboring the nucleotide sequence or construct of the present invention is thus preferably transferred into a suitable Agrobacterium strain, e.g. *A. tumefaciens*, so as to obtain an Agrobacterium cell harbouring the promoter or nucleotide sequence or construct of the present invention, which DNA is subsequently transferred into the plant cell to be modified.

If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et at., Crit. Rev. Plant Sci., 4:1–46: and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be performed in or on a certain part or tissue of the plant, i.e. on a part of a leaf, a root, a stem or another part of the plant.

Typically, with direct infection of plant tissues by Agrobacterium carrying the GOI (such as the nucleotide sequence according to the present invention) and, optionally, a promoter, a plant to be infected is wounded, e.g. by cutting the plant with a razor blade or puncturing the plant with a needle or rubbing the plant with an abrasive. The wound is then inoculated with the Agrobacterium. The inoculated plant or plant part is then grown on a suitable culture medium and allowed to develop into mature plants.

When plant cells are constructed, these cells may be grown and maintained in accordance with well-known tissue culturing methods such as by culturing the cells in a suitable culture medium supplied with the necessary growth factors such as amino acids, plant hormones, vitamins, etc.

Regeneration of the transformed cells into genetically modified plants may be accomplished using known methods for the regeneration of plants from cell or tissue cultures, for example by selecting transformed shoots using an antibiotic and by subculturing the shoots on a medium containing the appropriate nutrients, plant hormones, etc.

Further teachings on plant transformation may be found in EP-A-0449375.

As reported in CA-A-2006454, a large amount of cloning vectors are available which contain a replication system in *E. coli* and a marker which allows a selection of the transformed cells. The vectors contain for example pBR 322, pUC series, M13 mp series, pACYC 184 etc. In this way, the nucleotide or construct of the present invention can be introduced into a suitable restriction position in the vector. The contained plasmid is then used for the transformation in *E. coli*. The *E. coli* cells are cultivated in a suitable nutrient medium and then harvested and lysed. The plasmid is then recovered. As a method of analysis there is generally used sequence analysis, restriction analysis, electrophoresis and further biochemical-molecular biological methods. After each manipulation, the used DNA sequence can be restricted and connected with the next DNA sequence. Each sequence can be cloned in the same or different plasmid.

After the introduction of the nucleotide sequence or construct according to the present invention in the plants the presence and/or insertion of further DNA sequences may be necessary—such as to create combination systems as outlined above (e.g. an organism comprising a combination of constructs).

The above commentary for the transformation of prokaryotic organisms and plants with the nucleotide sequence of the present invention is equally applicable for the transformation of those organisms with the promoter of the present invention.

In summation, the present invention relates to affecting enzyme activity by expressing antisense intron sequences.

Also, the present invention relates to a promoter useful for the expression of those antisense intron sequences.

The following samples have been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on Jul. 13, 1995:

NCIMB 40753 (which refers to pBEA 8 as described herein);

NCIMB 40751 (which refers to λ-SBE 3.2 as described herein), and

NCIMB 40752 (which refers to λ-SBE 3.4 as described herein).

The following sample has been deposited in accordance with the Budapest Treaty at the recognised depositary The National Collections of Industrial and Marine Bacteria Limited (NCIMB) at 23 St Machar Drive, Aberdeen, Scotland, AB2 1RY, United Kingdom, on Jul. 9, 1996:

NCIMB 40815 (which refers to pBEA 9 as described herein).

A highly preferred embodiment of the present invention therefore relates to a method of affecting enzymatic activity in a plant (or a cell, a tissue or an organ thereof) comprising expressing in the plant (or a cell, a tissue or an organ thereof) a nucleotide sequence wherein the nucleotide sequence codes, partially or completely, for an intron in an antisense orientation; wherein the nucleotide sequence does not contain a sequence that is antisense to an exon sequence normally associated with the intron; wherein starch branching enzyme activity is affected and/or the levels of amylopectin are affected and/or the composition of starch is changed; and wherein the nucleotide sequence is antisense to intron 1 of class A SBE as set forth in SEQ. ID. No. 38, or any other intron of class A SBE, including fragments thereof, and including combinations of class A antisense intron sequences and class B antisense intron sequences. The sequence of introns of class A SBE other than intron 1 may be obtained by sequencing of, for example, potato class A SBE genomic DNA, isolatable by hybridisation screening of a genomic DNA library with class A SBE cDNA obtainable according to WO96/34968 according to methods well known in the art and set forth, for example, in Sambrook et al., Molecular Cloning: A Laboratory Manual, Cold Spring Harbor, 1989.

BRIEF DESCRIPTION OF THE DRAWINGS

FIG. 1, which is a schematic representation of the biosynthesis of amylose and amylopectin;

FIG. 10, which is a plasmid map of pVictor5a, which is 9.12 kb in size;

FIGS. 12A–12H, which show the full genomic nucleotide sequence (SEQ ID NOS: 29 & 41) for SBE including the promoter, exons and introns;

FIGS. 14A–14E, which show the sequence (SEQ ID NOS: 39 & 40) of intron 1 of the potato class A SBE;

FIGS. 1 and 2 were referred to above in the introductory description concerning starch in general. FIG. 3 was referred to above in the introductory description concerning antisense expression.

As mentioned, FIG. 4 is a diagrammatic representation of the exon-intron structure of a genomic SBE clone, the sequence of which is shown in FIGS. 12A–12H. This clone, which has about 11.5 k base pairs, comprises 14 exons and 13 introns. The introns are numbered in increasing order from the 5' end to the 3' end and correspond to SEQ.I.D.No.s 1–13, respectively. Their respective antisense intron sequences are shown as SEQ.I.D.No.s 15–27.

In more detail, FIGS. 4 and 12A–12H present information on the 11478 base pairs of a potato SBE gene. The 5' region from nucleotides 1 to 2082 contain the promoter region of the SBE gene. A TATA box candidate at nucleotide 2048 to 2051 is boxed. The homology between a potato SBE cDNA clone (Poulsen & Kreiberg (1993) Plant Physiol 102: 1053–1054) and the exon DNAs begin at 2083 bp and end at 9666 bp.

The homology between the cDNA and the exon DNA is indicated by nucleotides in upper case letters, while the translated amino acid sequences are shown in the single letter code below the exon DNA. Intron sequences are indicated by lower case letters.

Figure 2:
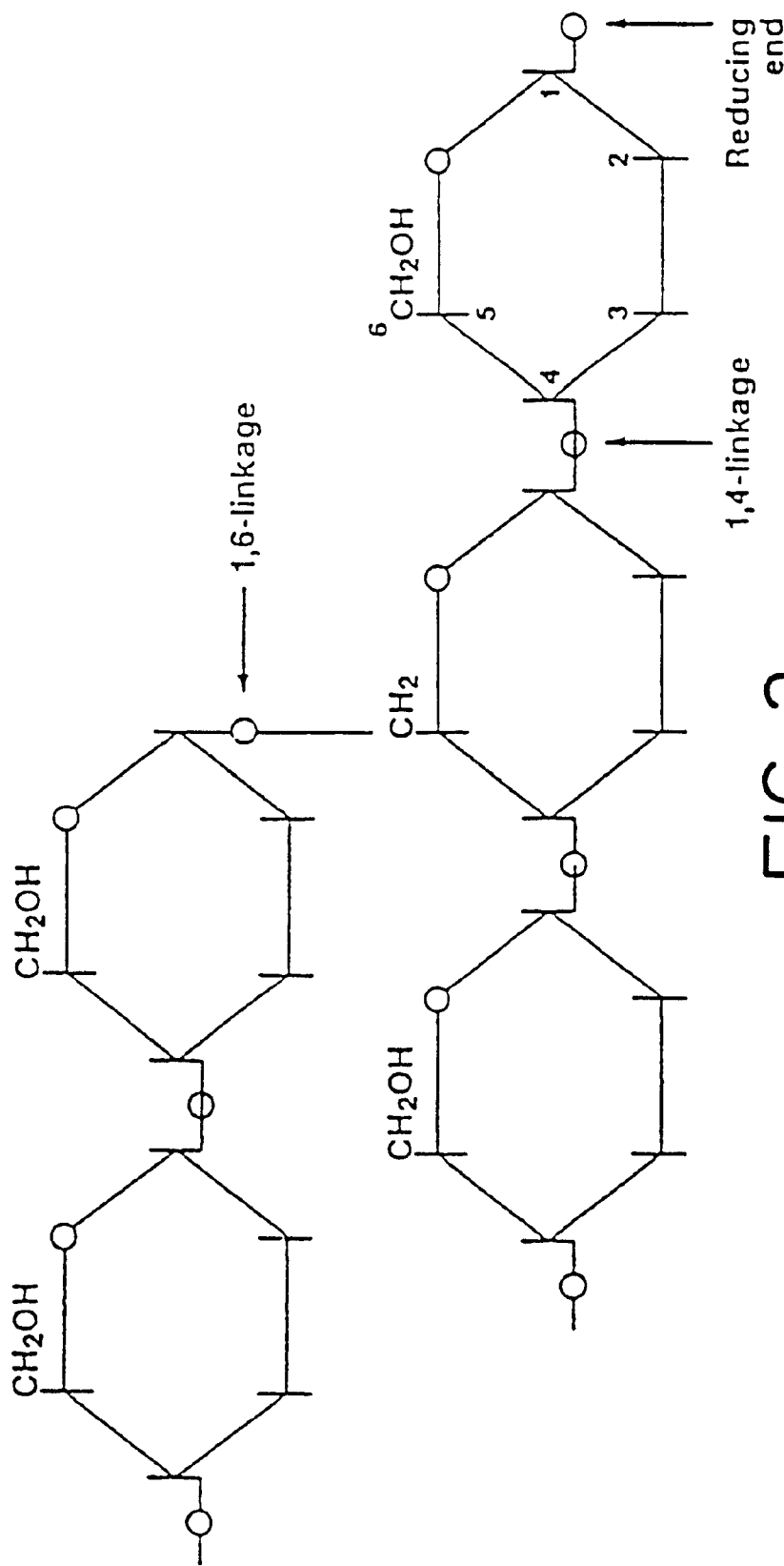
FIG. 2, which is a diagrammatic representation of the alpha-1–4 links and the alpha-1–6 links of amylopectin.
Figure 3:
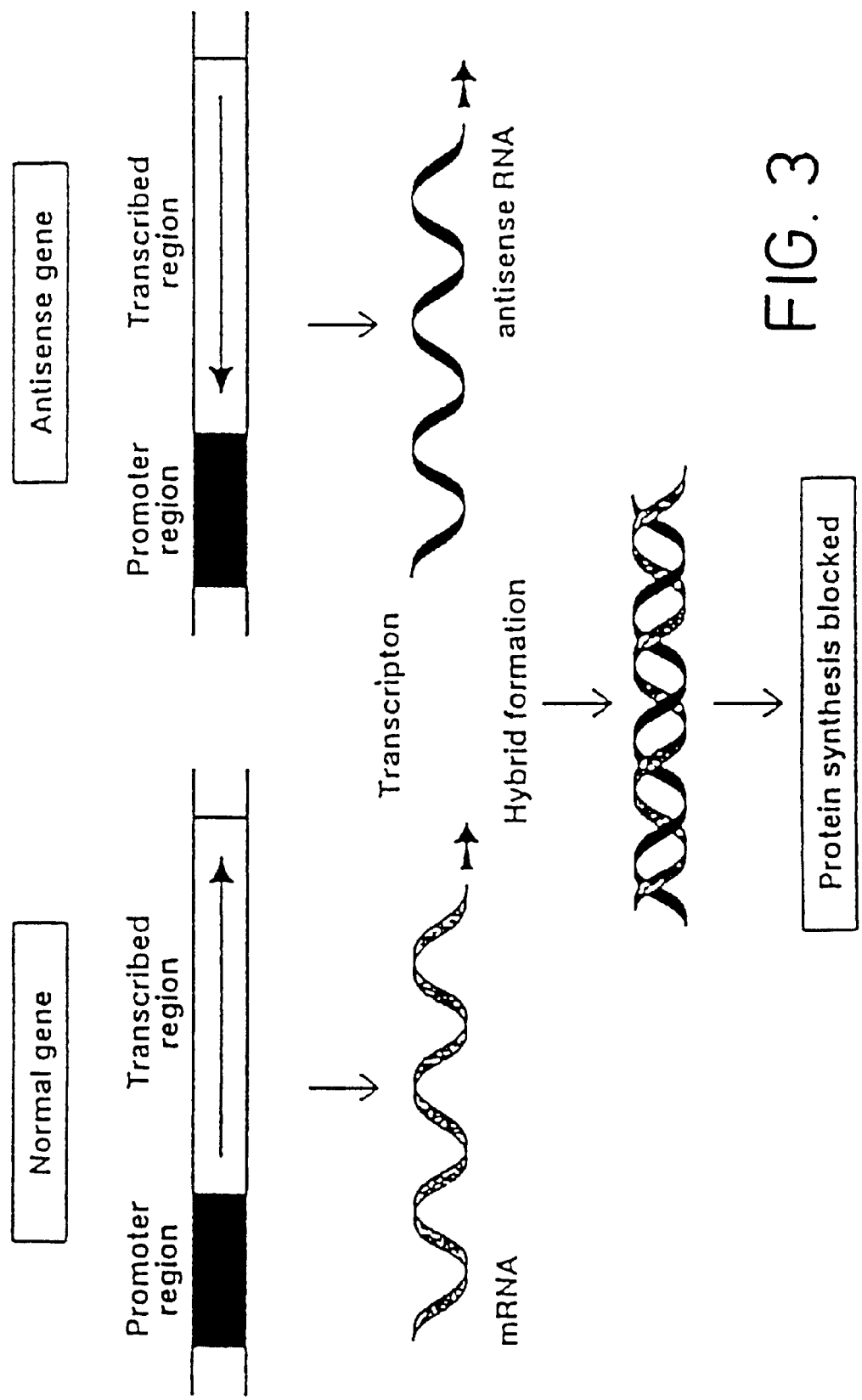
FIG. 3, which is a diagrammatic representation of a possible antisense-RNA inhibition mechanism.
Figure 4:
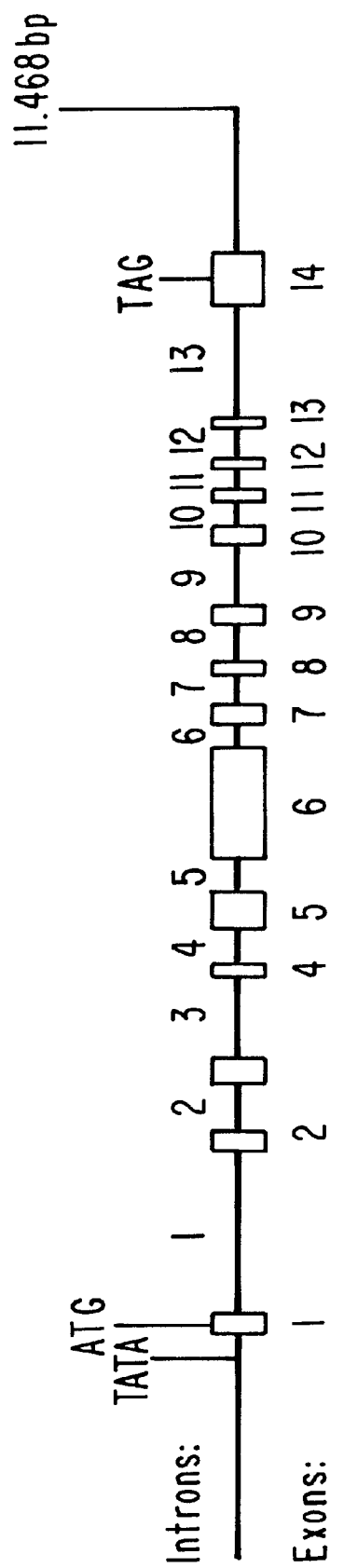
FIG. 4, which is a diagrammatic representation of the exon-intron structure of a genomic SBE clone.
Figure 5:
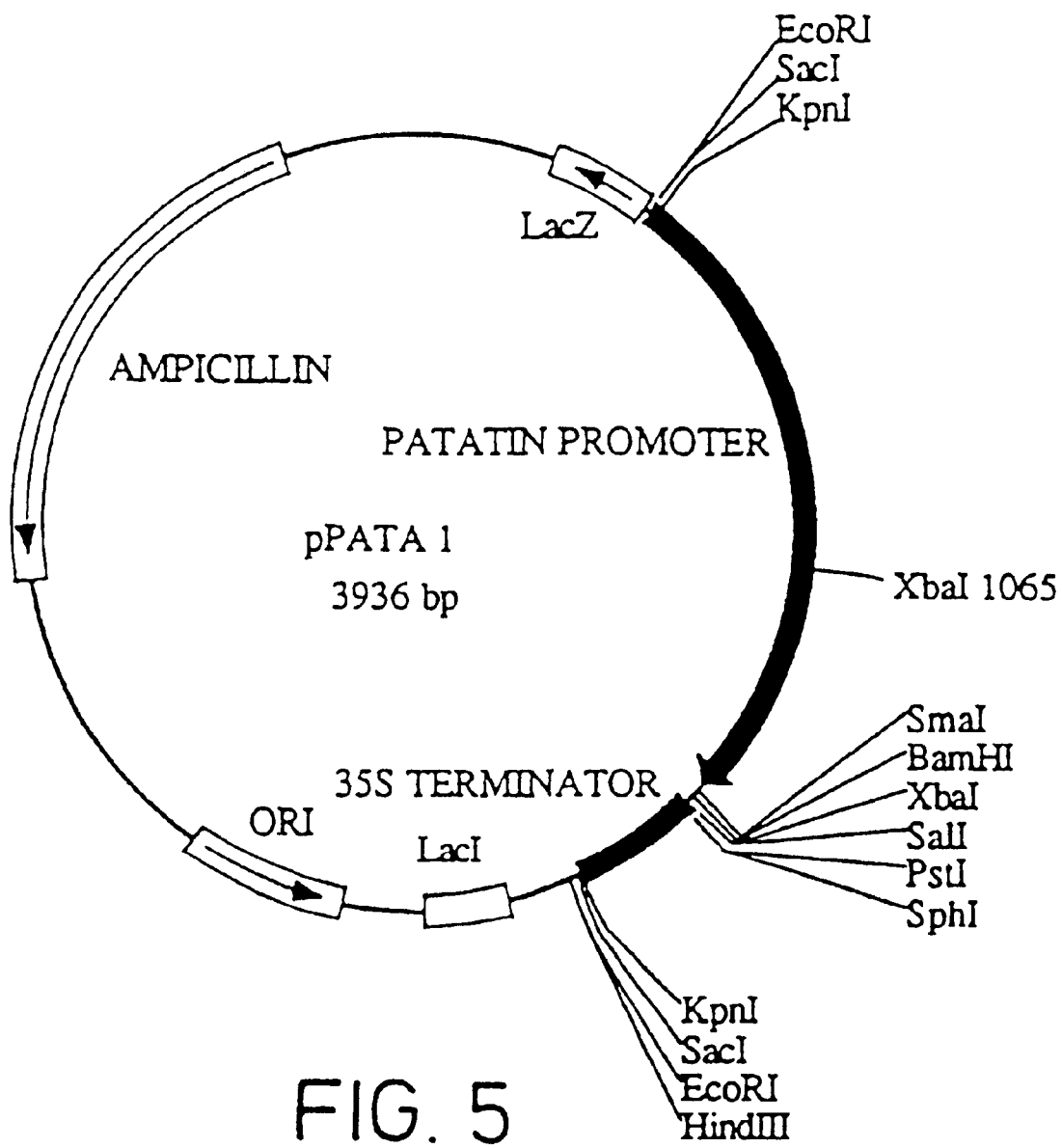
FIG. 5, which is a plasmid map of pPATA1, which is 3936 bp in size.
Figure 6:
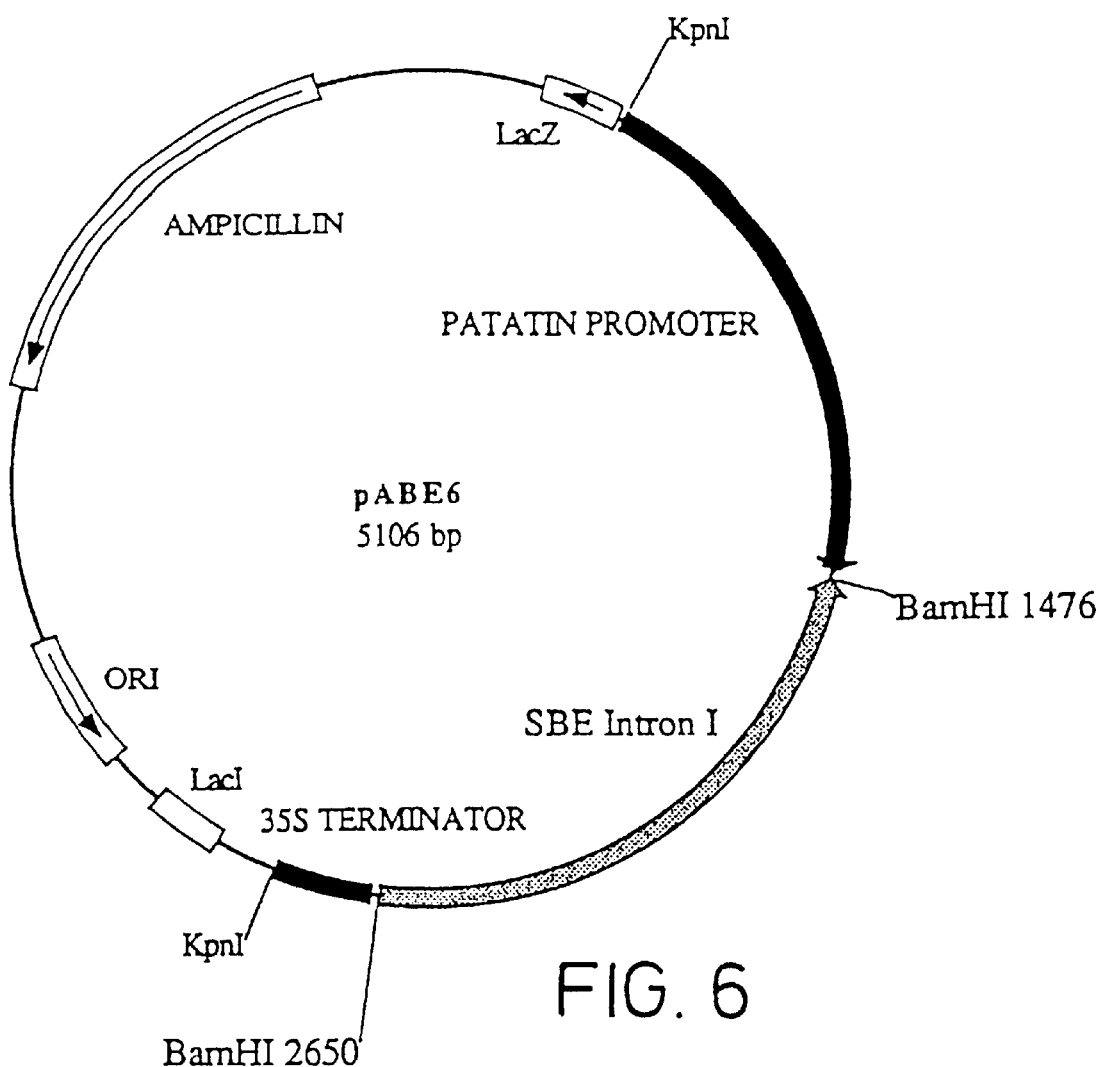
FIG. 6, which is a plasmid map of pABE6, which is 5106 bp in size.
Figure 7:
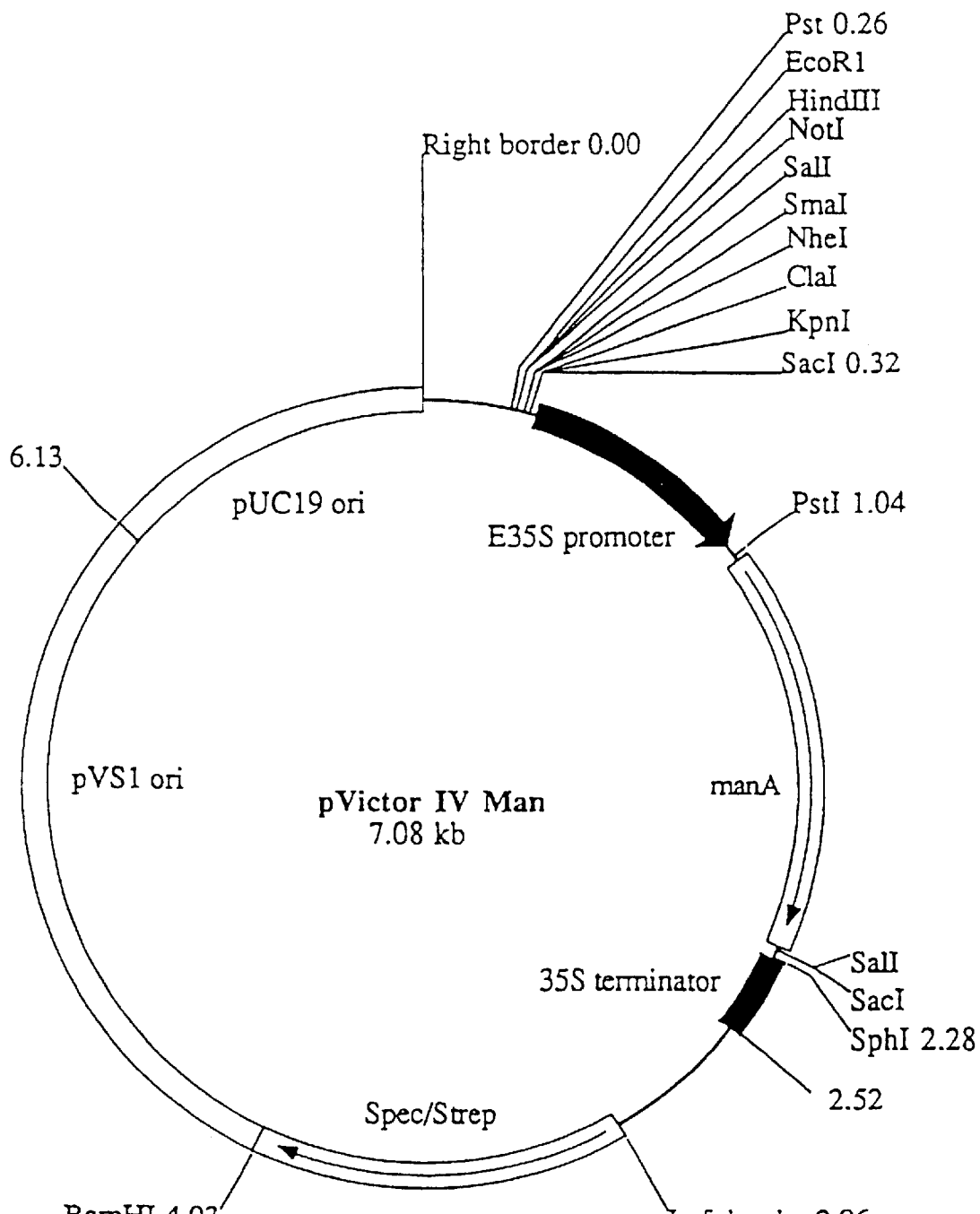
FIG. 7, which is a plasmid map of pVictorIV Man, which is 7080 bp in size.
Figure 8:
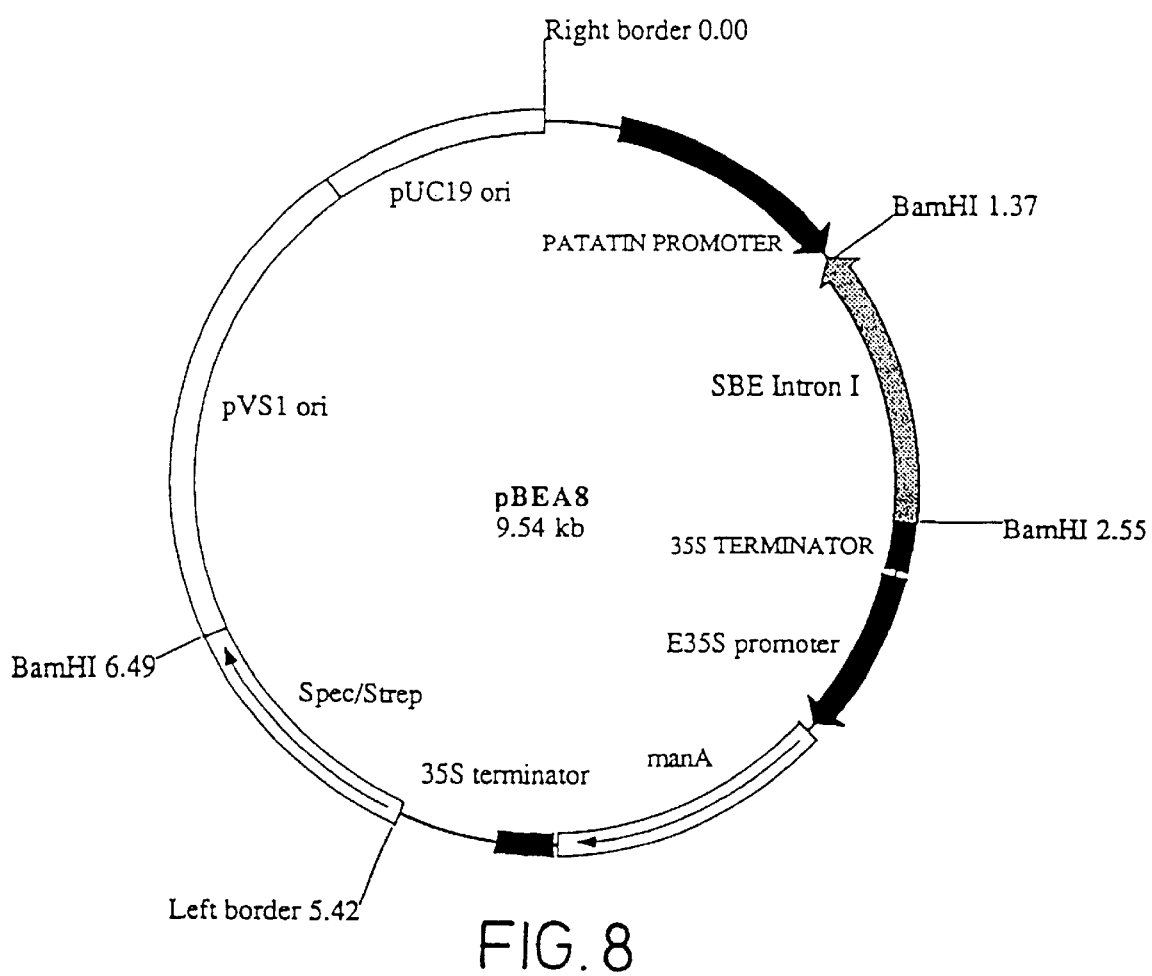
FIG. 8, which is a plasmid map of pBEA8, which is 9.54 kb in size.
Figure 9:
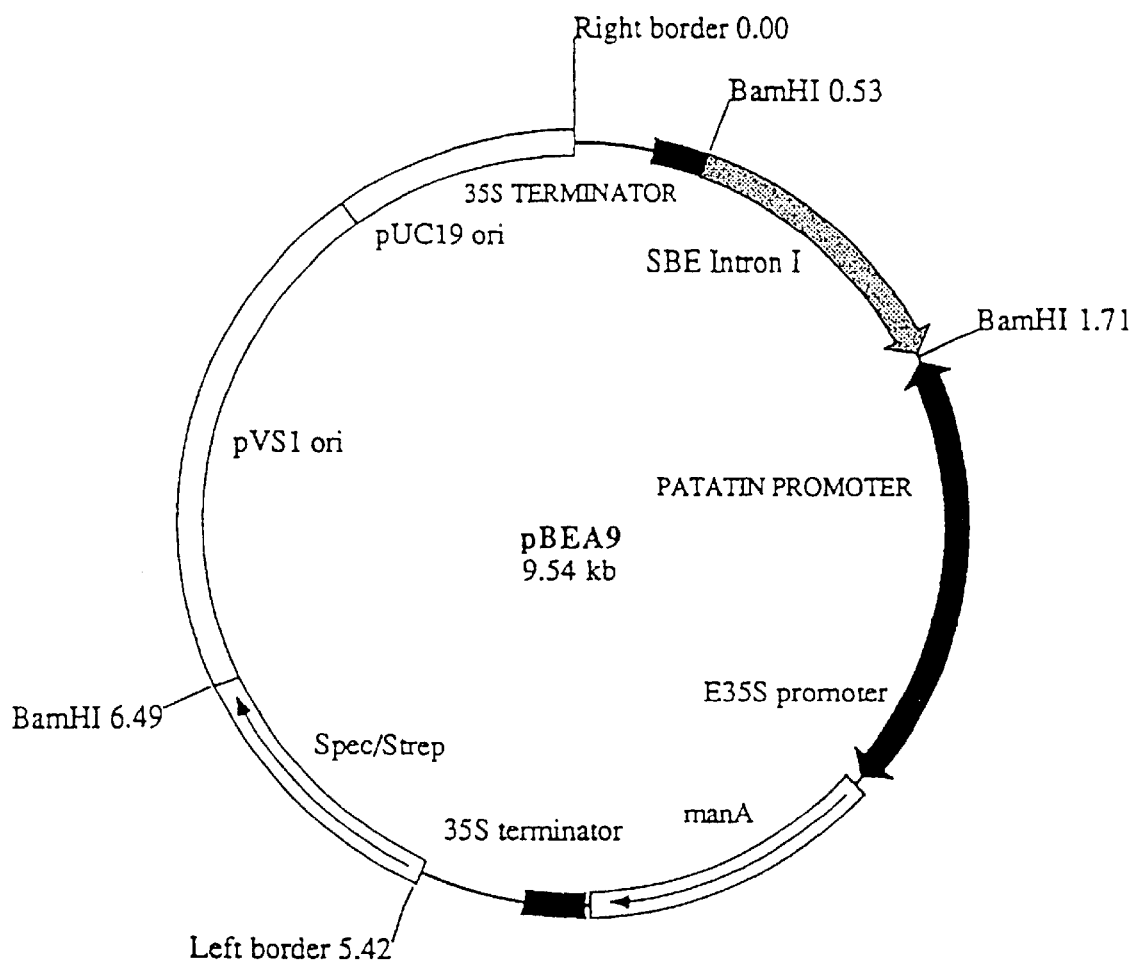
FIG. 9, which is a plasmid map of pBEA9, which is 9.54 kb in size.

FIGS. 5 to 7 are discussed below. As mentioned, FIG. 8 is a plasmid map of pBEA8, which is 9.54 k base pairs in size; and FIG. 9 is a plasmid map of pBEA9, which is 9.54 k base pairs in size. Each of pBEA 8 and pBEA 9 comprises an antisense sequence to the first intron sequence of the potato SBE gene. This first intron sequence, which has 1177 base pairs, is shown in FIG. 4 and lies between the first exon and the second exon.

These experiments and aspects of the present invention are now discussed in more detail.

DETAILED DESCRIPTION OF THE INVENTION

EXPERIMENTAL PROTOCOL

ISOLATION, SUBCLONING IN PLASMIDS, AND SEQUENCING OF GENOMIC CLASS B SBE CLONES

Various clones containing the potato class B SBE gene are isolated from a Desiree potato genomic library (Clontech Laboratories Inc., Palo Alto Calif., USA) using radioactively labelled potato SBE cDNA (Poulsen & Kreiberg (1993) Plant Physiol. 102:1053–1054) as probe. The fragments of the isolated λ-phages containing SBE DNA (λSBE 3.2— NCIMB 40751— and λSBE-3.4—NCIMB 40752) are identified by Southern analysis and then subcloned into pBluescript II vectors (Clontech Laboratories Inc., Palo Alto Calif., USA). λSBE 3.2 contains a 15 kb potato DNA insert and λSBE-3.4 contains a 13 kb potato DNA insert. The resultant plasmids are called pGB3, pGB11, pGB15, pGB16 and pGB25 (see discussion below). The respective inserts are then sequenced using the Pharmacia Autoread Sequencing Kit (Pharmacia. Uppsala) and a A.L.F. DNA sequencer (Pharmacia, Uppsala).

In total, a stretch of 11.5 kb of the class B SBE gene is sequenced. The sequence is deduced from the above-mentioned plasmids, wherein: pGB25 contains the sequences from 1 bp to 836 bp, pGBI5 contains the sequences from 735 bp to 2580 bp, pGB16 contains the sequences from 2580 bp to 5093 bp, pGB11 contains the sequences from 3348 bp to 7975 bp, and pGB3 contains the sequences from 7533 bp to 11468 bp.

In more detail, pGB3 is constructed by insertion of a 4 kb EcoRI fragment isolated from λSBE 3.2 into the EcoRI site of pBluescript II SK (+). pGB11 is constructed by insertion of a 4.7 kb XhoI fragment isolated from λSBE 3.4 into the XhoI site of pBluescript II SK (+). pGB15 is constructed by insertion of a 1.7 kb SpeI fragment isolated from λSBE 3.4 into the SpeI site of pBluescript II SK (+). pGB16 is constructed by insertion of a 2.5 kb SpeI fragment isolated from λSBE 3.4 into the SpeI site of pBluescript II SK (+). For the construction of pGB25 a PCR fragment is produced with the primers 5' GGA ATT CCA GTC GCA GTC TAC ATT AC 3' (SEQ. ID. No.30)

and

5' CGG GAT CCA GAG GCA TTA AGA TTT CTG G 3' (SEQ. ID. No. 31)

and λSBE 3.4 as a template.

The PCR fragment is digested with BamHI and EcoRI, and inserted in pBluescript II SK (+) digested with the same restriction enzymes.

A class A SBE clone is derived similarly.

CONSTRUCTION OF CLASS B SBE ANTISENSE INTRON PLASMIDS pBEA8 AND pBEA9

The SBE intron 1 is amplified by PCR using the oligonucleotides:

5' CGG GAT CCA AAG AAA TTC TCG AGG TTA CAT GG 3' (SEQ. ID. No. 32)

and

5' CGG GAT CCG GGG TAA TTT TTA CTA ATT TCA TG 3' (SEQ. ID. No. 33)

and the λSBE 3.4 phage containing the SBE gene as template.

The PCR product is digested with BamHI and inserted in an antisense orientation in the BamHI site of plasmid pPATA1 (described in WO 94/24292) between the patatin promoter and the 35S terminator. This construction, pABE6, is digested with KpnI, and the 2.4 kb "patatin promoter-SBE intron 1-35S terminator" KpnI fragment is isolated and inserted in the KpnI site of the plant transformation vector pVictorIV Man. The KpnI fragment is inserted in two orientations yielding plasmids pBEA8 and pBEA9. pVictorIV Man is shown in FIG. 7 and is formed by insertion of a filled in XbaI fragment containing a E35S promoter-manA-35S terminator cassette isolated from plasmid pVictorIV SGiN Man (WO 94/24292) into the filled in XhoI site of pVictor IV. The pVictor regions of pvictor IV Man contained between the co-ordinates 2.52 bp to 0.32 bp (see FIG. 7).

CONSTRUCTION OF CLASS A SBE ANTISENSE INTRON PLASMIDS pSS17 AND pSS18

Construction of Plasmid pSS17.

Figure 15:
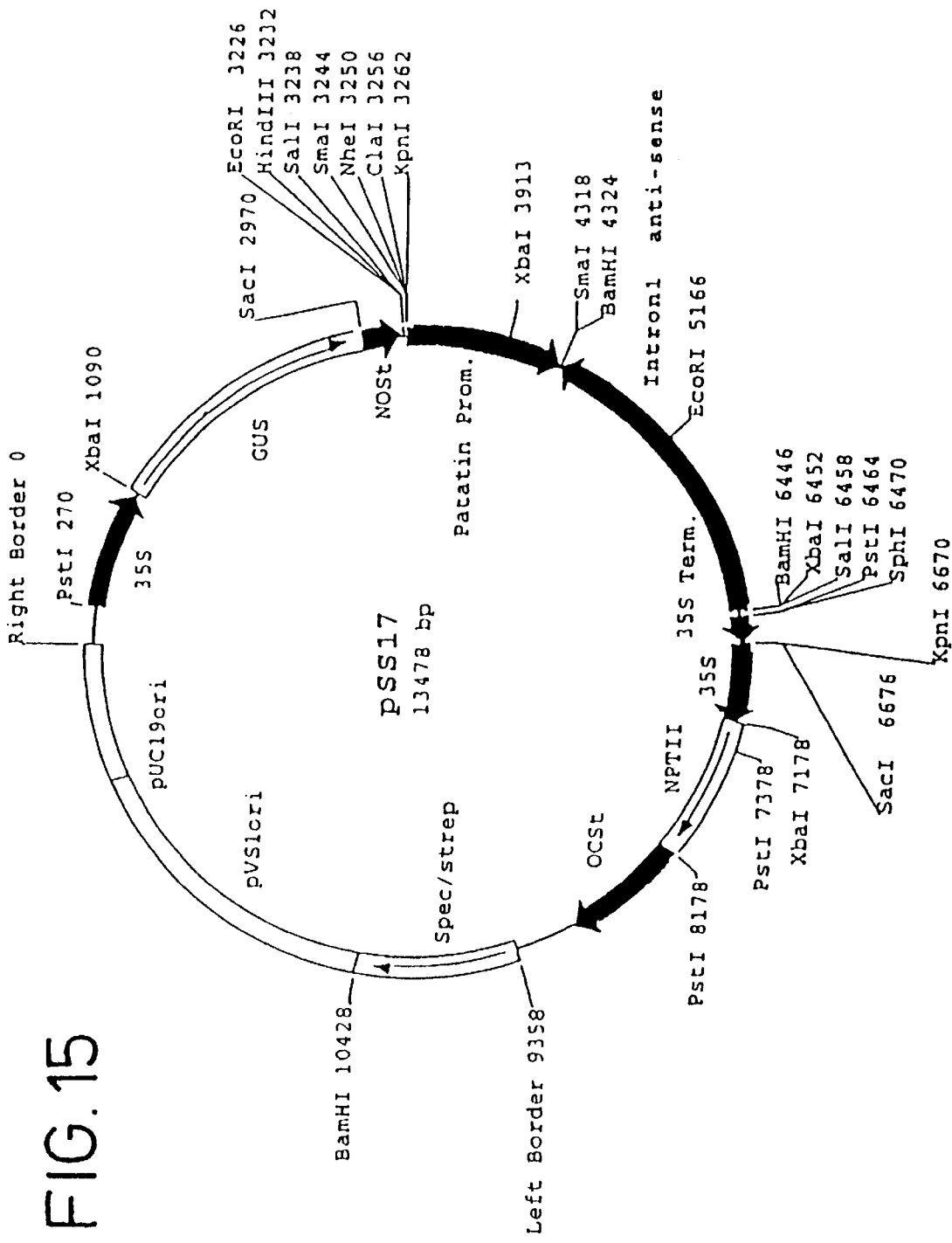
FIG. 15, which shows the structure of pSS17.

The 2122 bp intron 1 sequence of the potato SBEII gene is amplified by PCR from a genomic SBEII subclone using the primers 5'-CGG GAT CCC GTA TGT CTC ACT GTG TTT GTG GC-3' (SEQ. ID. No. 34) and 5'-CGG GAT CCC CCT ACA TAC ATA TAT CAG ATT AG-3' (SEQ. ID. No. 35). The PCR product is digested with BamHI and inserted in antisense orientation after a patatin promoter in the BamHI site of a plant transformation vector in which the NPTII gene is used as selectable marker (see FIG. 15).

Construction of Plasmid pSS18.

Figure 16:
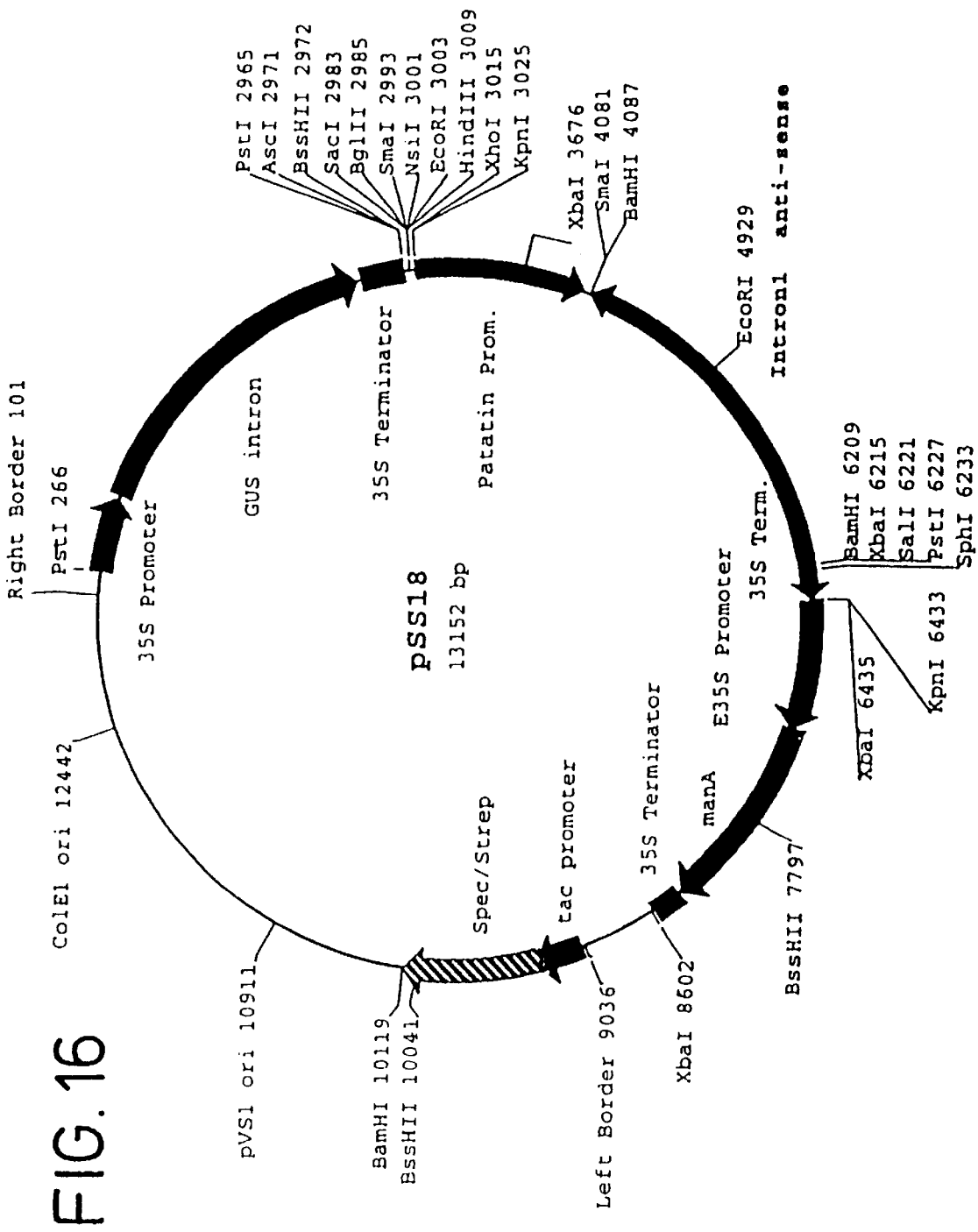
FIG. 16, which shows the structure of pSS18.

The 2122 bp intron 1 sequence of the potato SBEII gene is amplified by PCR from a genomic SBEII subclone using the primers 5'-CGG GAT CCC GTA TGT CTC ACT GTG TTT GTG GC-3' (SEQ. ID. No. 34) and 5'-CGG GAT CCC CCT ACA TAC ATA TAT CAG ATT AG-3' (SEQ. ID. No. 35). The PCR product is digested with BanmHI and inserted in antisense orientation after a patatin promoter in the BamnHI site of a plant transformation vector in which the manA gene is used as selectable marker (see FIG. 16).

PRODUCTION OF TRANSGENIC POTATO PLANTS

Axenic Stock Cultures

Shoot cultures of *Solanum tuberosum* 'Bintje' and 'Dianella' are maintained on a substrate (LS) of a formula according to Linsmaier, E. U. and Skoog, F. (1965), Physiol. Plant. 18: 100–127, in addition containing 2 µM silver thiosulphate at 25° C. and 16 h light/8 h dark.

The cultures are subcultured after approximately 40 days. Leaves are then cut off the shoots and cut into nodal segments (approximately 0.8 cm) each containing one node.

Inoculation of Potato Tissues

Shoots from approximately 40 days old shoot cultures (height approximately 5–6 cms) are cut into internodal segments (approximately 0.8 cm). The segments are placed into liquid LS-substrate containing the transformed *Agrobacterium tumefaciens* containing the binary vector of interest. The Agrobacterium are grown overnight in YMB-substrate (di-potassium hydrogen phosphate, trihydrate (0.66 g/l); magnesium sulphate, heptahydrate (0.20 g/l); sodium chloride (0.10 g/l); mannitol (10.0 g/l); and yeast extract (0.40 g/l)) containing appropriate antibiotics (corresponding to the resistance gene of the Agrobacterium strain) to an optical density at 660 nm (OD-660) of approximately 0.8, centrifuged and resuspended in the LS-substrate to an OD-660 of 0.5.

The segments are left in the suspension of Agrobacterinim for 30 minutes and then the excess of bacteria are removed by blotting the segments on sterile filter paper.

Co-cultivation

The shoot segments are co-cultured with bacteria for 48 hours directly on LS-substrate containing agar (8.0 g/l), 2,4-dichlorophenoxyacetic acid (2.0 mg/l) and transzeatin (0.5 mg/l). The substrate and also the explants are covered with sterile filter papers, and the petri dishes are placed at 25° C. and 16 h light/8 dark.

"Washing" Procedure

After the 48 h on the co-cultivation substrate the segments are transferred to containers containing liquid LS-substrate containing 800 mg/l carbenicillin. The containers are gently shaken and by this procedure the major part of the Agrobacterium is either washed off the segments and/or killed.

Selection

After the washing procedure the segments are transferred to plates containing the LS-substrate, agar (8 g/l), transzeatin (1–5 mg/l), gibberellic acid (0.1 mg/l), carbenicillin (800 mg/l), and kanamycin sulphate (50–100 mg/l) or phosphinotricin (1–5 mg/l) or mannose (5 g/l) depending on the vector construction used. The segments are sub-cultured to fresh substrate each 3–4 weeks.

In 3 to 4 weeks, shoots develop from the segments and the formation of new shoots continued for 3–4 months.

Rooting of Regenerated Shoots

The regenerated shoots are transferred to rooting substrate composed of LS-substrate, agar (8 g/l) and carbenicillin (800 mg/l).

The transgenic genotype of the regenerated shoot is verified by testing the rooting ability on the above mentioned substrates containing kanamycin sulphate (200 mg/l), by performing NPTII assays (Radke, S. E. et al, Theor. Appl. Genet. (1988), 75: 685–694) or by performing PCR analysis according to Wang et al (1993, NAR 21 pp 4153–4154). Plants which are not positive in any of these assays are discarded or used as controls. Alternatively, the transgenic plants could be verified by performing a GUS assay on the co-introduced β-glucuronidase gene according to Hodal, L. et al. (Pl. Sci. (1992), 87: 115–122).

Transfer to Soil

The newly rooted plants (height approx. 2–3 cms) are transplanted from rooting substrate to soil and placed in a growth chamber (21° C., 16 hour light 200–400 uE/m²/sec). When the plants are well established they are transferred to the greenhouse, where they are grown until tubers had developed and the upper part of the plants are senescing.

Harvesting

The potatoes are harvested after about 3 months and then analysed.

BRANCHING ENZYME ANALYSIS

The class A and class B SBE expression in the transgenic potato lines is measured using the SBE assays described by Blennow and Johansson (Phytochemistry (1991) 30:437–444) and by standard Western procedures using antibodies directed against potato SBE.

STARCH ANALYSIS

Starch is isolated from potato tubers and analysed for the amylose:amylopectin ratio (Hovenkamp-Hermelink et al. (1988) Potato Research 31:241–246). In addition, the chain length distribution of amylopectin is determined by analysis of isoamylase digested starch on a Dionex HPAEC.

The number of reducing ends in isoamylase digested starch is determined by the method described by N. Nelson (1944) J. Biol.Chem. 153:375–380.

The results reveal that there is a reduction in the level of synthesis of SBE and/or the level of activity of SBE and/or the composition of starch SBE in the transgenic plants.

CONSTRUCTION OF SBE PROMOTER CONSTRUCT

An SBE promoter fragment is amplified from λ-SBE 3.4 using primers:

5' CCA TCG ATA CTT TAA GTG ATT TGA TGG C 3' (SEQ. ID. No. 36)

and

5' CGG GAT CCT GTT CTG ATT CTT GAT TTC C 3' (SEQ. ID. No. 37)

Figure 10:
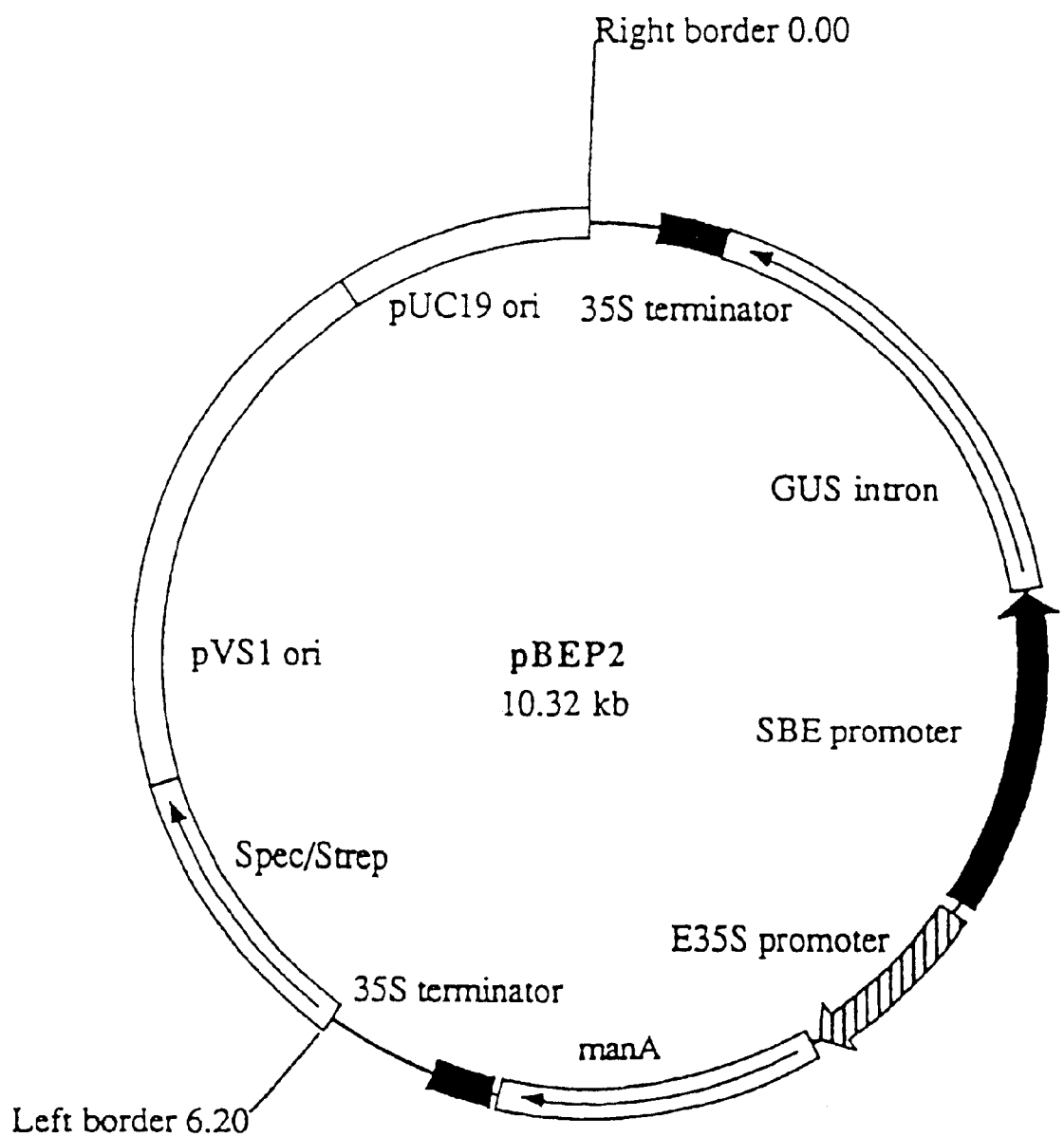
FIG. 10, which is a plasmid map of pBEP2, which is 10.32 kb in size.
Figure 11:
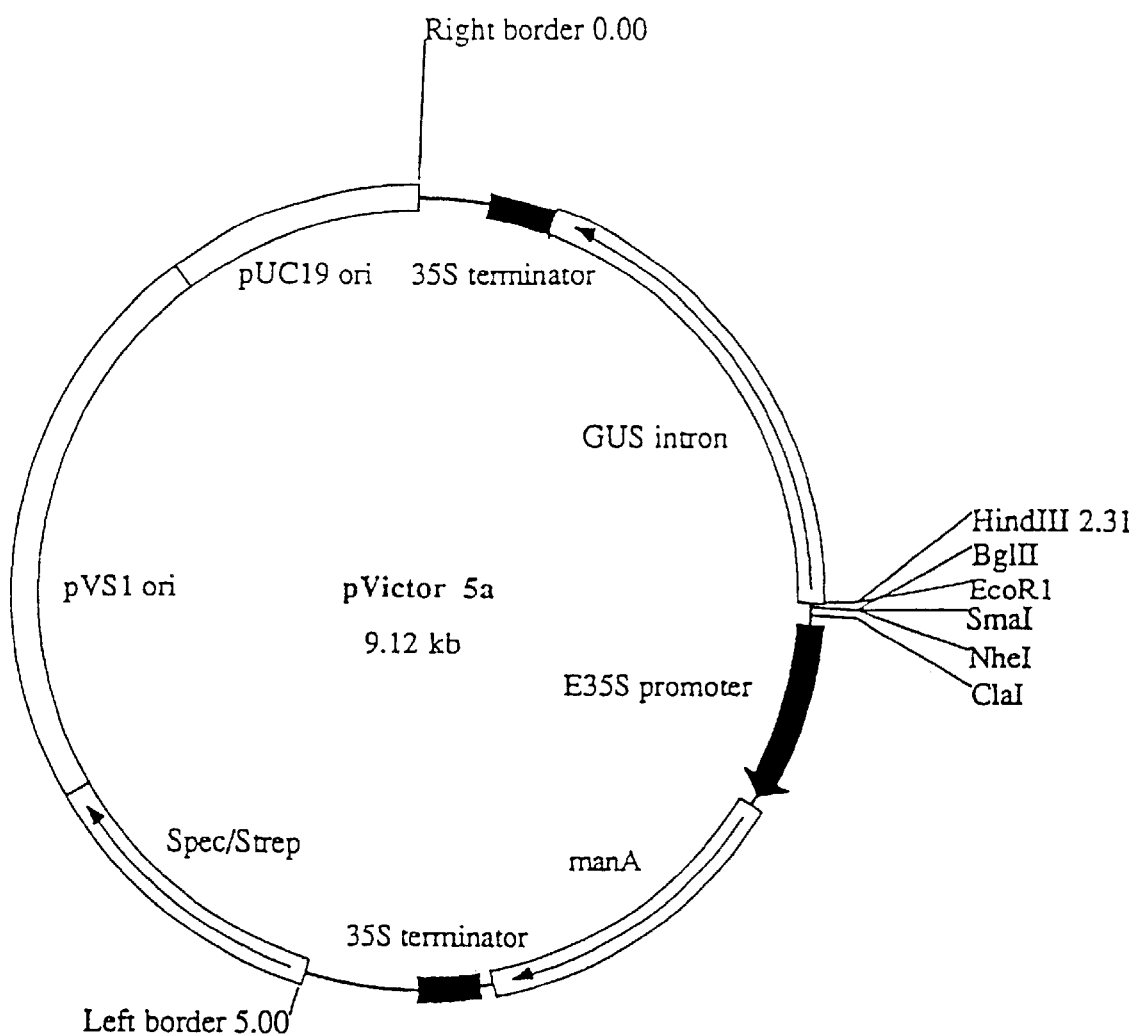
Figure 13:
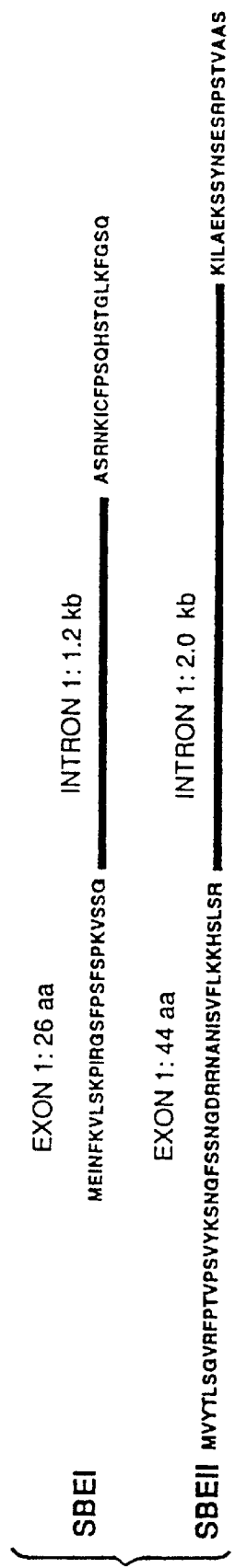
FIG. 13, which shows the positioning of intron 1 in the class A and class B SBE genes (a portion of SEQ ID NO: 41, as well as SEQ ID NOS: 42 & 43)

The PCR product is digested with Cla/I and BamHI. The resultant 1.2 kb fragment is then inserted in pVictor5a (see FIG. 11) linearised with ClaI and BglII yielding pBEP2 (see FIG. 10).

STARCH BRANCHING ENZYME MEASUREMENTS OF POTATO TUBERS

Potatoes from potato plants transformed with pBEA8, pBEA9, pSS17 or pSS18 are cut in small pieces and homogenised in extraction buffer (50 mM Tris-HCl pH 7.5, Sodium-dithionite (0.1 g/l), and 2 mM DTT) using a Ultra-Turax homogenizer; 1 g of Dowex xl. is added pr. 10 g of tuber. The crude homogenate is filtered through a miracloth filter and centrifuged at 4° C. for 10 minutes at 24.700 g. The supernatant is used for starch branching enzyme assays.

The starch branching enzyme assays are carried out at 25° C. in a volume of 400 μl composed of 0.1 M Na citrate buffer pH 7.0, 0.75 mg/ml amylose, 5 mg/ml bovine serum albumin and the potato extract. At 0, 15, 30 and 60 minutes aliqouts of 50 μl are removed from the reaction into 20 μl 3 N HCl. 1 ml of iodine solution is added and the decrease in absorbance at 620 nm is measured with an ELISA spectrophotometer.

The starch branching enzyme (SBE) levels are measured in tuber extracts from 34 transgenic Dianella potato plants transformed with plasmid pBEA8, pSS17 and pSS18.

The transformed transgenic lines produce tubers which have SBE levels that are 10% to 15% of the appropriate class A or class B SBE levels found in non transformed Dianella plants.

In a further experiment, plasmids pSS17 and pBEA8 are cotransfected into potato plants, as described above. In the cotransfectants, when analysed as set forth above, simultaneous reduction of class A and class B SBE levels are observed.

SUMMATION

The above-mentioned examples relate to the isolation, sequencing and utilisation of antisense intron constructs derived from a gene for potato class A and class B SBE. These SBE intron antisense constructs can be introduced into plants, such as potato plants. After introduction, a reduction in the level of synthesis of SBE and/or the level of activity of SBE and/or the composition of starch in plants can be achieved.

Without wishing to be bound by theory it is believed that the expressed anti-sense nucleotide sequence of the present invention binds to sense introns on pre-mRNA and thereby prevents pre-mRNA splicing and/or subsequent translation of mRNA. This binding therefore is believed to reduce the level of plant enzyme activity (in particular class A and class B SBE activity), which in turn for SBE activity is believed to influence the amylose:amylopectin ratio and thus the branching pattern of amylopectin.

Thus, the present invention provides a method wherein it is possible to manipulate the starch composition in plants, or tissues or cells thereof, such as potato tubers, by reducing the level of SBE activity by using an antisense-RNA technique using antisense intron sequences.

The simultaneous reduction or elimination of class A and class B SBE sequences from the doubly transformed potato plants, moreover, offers the possibility to transform such plants with different SBE genes at will, thus allowing the manipulation of branching in starch according to the desired result.

Other modifications of the present invention will be apparent to those skilled in the art without departing from the scope of the present invention.

The following pages present a number of sequence listings which have been consecutively numbered from SEQ.I.D. No. 1–SEQ.I.D. No. 38. In brief, SEQ.I.D. No. 1–SEQ.I.D. No. 13 represent sense intron sequences (genomic DNA); SEQ.I.D. No. 14 represents the SBE promoter sequence (genomic sequence); SEQ.I.D. No. 15–SEQ.I.D. No. 27 represent antisense intron sequences; and SEQ. I.D. No. 28 represents is the sequence complementary to the SBE promoter sequence—i.e. the SBE promoter sequence in antisense orientation. The full genomic nucleotide sequence for class B SBE including the promoter, exons and introns is shown as SEQ. I.D. No. 29 and is explained by way of FIGS. 4 and 12A–12H which highlight particular gene features. SEQ. ID. No. 30 to 37 show primers used in the methods set forth above. SEQ. ID. No. 38 shows the sequence of intron 1 of class A SBE.

SEQUENCE LISTING

```
<160> NUMBER OF SEQ ID NOS: 43

<210> SEQ ID NO 1
<211> LENGTH: 1165
<212> TYPE: DNA
<213> ORGANISM: Solanum tuberosum

<400> SEQUENCE: 1
gtaattttta ctaatttcat gttaatttca attatttta gcctttgcat ttcattttcc      60
aatatatctg gatcatctcc ttagtttttt attttatttt ttataatatc aaatatggaa    120
gaaaaatgac acttgtagag ccatatgtaa gtatcatgtg acaaatttgc aaggtggttg    180
agtgtataaa attcaaaaat tgagagatgg aggggggtg ggggaagaca atatttagaa    240
agagtgttct aggaggttat ggaggacacg gatgaggggt agaaggttag ttaggtattt    300
gagtgttgtc tggcttatcc tttcatacta gtagtcgtgg aattatttgg gtagtttctt    360
gttttgttat ttgatctttg ttattctatt ttctgtttct tgtacttcga ttattgtatt    420
atatatcttg tcgtagttat tgttcctcgg taagaatgct ctagcatgct tcctttagtg    480
ttttatcatg ccttctttat attcgcgttg ctttgaaatg cttttacttt agccgagggt    540
ctattagaaa caatctctct atctcgtaag gtagggtaa agtcctcacc acactccact    600
tgtgggatta cattgtgttt gttgttgtaa atcaattatg tatacataat aagtggattt    660
tttacaacac aaatacatgg tcaagggcaa agttctgaac acataaaggg ttcattatat    720
gtccagggat atgataaaaa ttgtttcttt gtgaaagtta tataagattt gttatggctt    780
ttgctggaaa cataataagt tataatgctg agatagctac tgaagtttgt tttttctagc    840 ctttaaatg taccaataat agattccgta tcgaacgagt atgtttgat tacctggtca     900 tgatgtttct attttttaca tttttttggt gttgaactgc aattgaaaat gttgtatcct    960
atgagacgga tagttgagaa tgtgttcttt gtatggacct tgagaagctc aaacgctact  1020
ccaataattt ctatgaattc aaattcagtt tatggctacc agtcagtcca gaaattagga  1080
tatgctgcat atacttgttc aattatactg taaaattct taagttctca agatatccat  1140
gtaacctcga gaatttcttt gacag                                        1165

<210> SEQ ID NO 2
<211> LENGTH: 317
<212> TYPE: DNA
```

<213> ORGANISM: Solanum tuberosum

<400> SEQUENCE: 2

```
gtatgtttga taatttatat ggttgcatgg atagtatata aatagttgga aaacttctgg      60
actggtgctc atggcatatt tgatctgtgc accgtgtgga gatgtcaaac atgtgttact     120
tcgttccgcc aatttataat accttaactt gggaaagaca gctctttact cctgtgggca     180
tttgttattt gaattacaat ctttatgagc atggtgtttt cacattatca acttctttca     240
tgtggtatat aacagttttt agctccgtta ataccttcct ctttttgat ataaactaac      300
tgtggtgcat tgcttgc                                                    317
```

<210> SEQ ID NO 3
<211> LENGTH: 504
<212> TYPE: DNA
<213> ORGANISM: Solanum tuberosum

<400> SEQUENCE: 3

```
gtaacagcca aaagttgtgc tttaggcagt ttgaccttat tttggaagat gaattgttta      60
tacctacttt gactttgcta gagaattttg cataccgggg agtaagtagt ggctccattt     120
aggtggcacc tggccatttt tttgatcttt taaaaagctg tttgattggg tcttcaaaaa     180
agtagacaag gttttggag aagtgacaca cccccggagt gtcagtggca aagcaaagat     240
tttcactaag gagattcaaa atataaaaaa agtatagaca taagaagct gagggattc      300
aacatgtact atacaagcat caaatatagt cttaaagcaa ttttgtagaa ataaagaaag     360
tcttccttct gttgcttcac aatttccttc tattatcatg agttactctt tctgttcgaa     420
atagcttcct taatattaaa ttcatgatac ttttgttgag atttagcagt ttttttcttgt    480
gtaaactgct ctctttttt gcag                                             504
```

<210> SEQ ID NO 4
<211> LENGTH: 146
<212> TYPE: DNA
<213> ORGANISM: Solanum tuberosum

<400> SEQUENCE: 4

```
gtaggtcctc gtctactaca aaatagtagt ttccatcatc ataacagatt ttcctattaa      60
agcatgatgt tgcagcatca ttggctttct tacatgttct aattgctatt aaggttatgc     120
ttctaattaa ctcatccaca atgcag                                          146
```

<210> SEQ ID NO 5
<211> LENGTH: 218
<212> TYPE: DNA
<213> ORGANISM: Solanum tuberosum

<400> SEQUENCE: 5

```
gttttgttat tcataccttg aagctgaatt ttgaacacca tcatcacagg catttcgatt      60
catgttctta ctagtcttgt tatgtaagac attttgaaat gcaaaagtta aaataattgt     120
gtctttacta atttggactt gatcccatac tctttccctt aacaaaatga gtcaattcta     180
taagtgcttg agaacttact acttcagcaa ttaaacag                             218
```

<210> SEQ ID NO 6
<211> LENGTH: 198
<212> TYPE: DNA
<213> ORGANISM: Solanum tuberosum

<400> SEQUENCE: 6

```
gtattttaaa tttatttcta caactaaata attctcagaa caattgttag atagaatcca      60
aatatatacg tcctgaaagt ataaaagtac ttattttcgc catgggcctt cagaatattg     120
gtagccgctg aatatcatga taagttattt atccagtgac attttttatgt tcactcctat   180 tatgtctgct ggatacag                                                  198
```

<210> SEQ ID NO 7
<211> LENGTH: 208
<212> TYPE: DNA
<213> ORGANISM: Solanum tuberosum

<400> SEQUENCE: 7

```
gtttgtctgt ttctattgca ttttaaggtt catataggtt agccacggaa aatctcactc     60
tttgtgaggt aaccagggtt ctgatggatt attcaatttt ctcgtttatc atttgtttat   120
tcttttcatg cattgtgttt cttttcaat atccctctta tttggaggta attttttctca   180 tctattcact tttagcttct aaccacag                                       208
```

<210> SEQ ID NO 8
<211> LENGTH: 293
<212> TYPE: DNA
<213> ORGANISM: Solanum tuberosum

<400> SEQUENCE: 8

```
gtatgtctta catctttaga tattttgtga taattacaat tagtttggct tacttgaaca     60
agattcattc ctcaaaatga cctgaactgt tgaacatcaa aggggttgaa acatagagga   120
aaacaacatg atgaatgttt ccattgtcta gggatttcta ttatgttgct gagaacaaat   180
gtcatcttaa aaaaaacatt gtttactttt ttgtagtata aagagattact gtatagagtt   240 tgcaagtgtg tctgttttgg agtaattgtg aaatgtttga tgaacttgta cag          293
```

<210> SEQ ID NO 9
<211> LENGTH: 376
<212> TYPE: DNA
<213> ORGANISM: Solanum tuberosum

<400> SEQUENCE: 9

```
gttcaagtat tttgaatcgc agcttgttaa ataatctagt aattttttaga ttgcttactt     60 ggaagtctac ttggttctgg ggatgatagc tcatttcatc ttgttctact tattttccaa   120
ccgaatttct gattttttgtt tcgagatcca agtattagat tcatttacac ttattaccgc   180
ctcatttcta ccactaaggc cttgatgagc agcttaagtt gattctttga agctatagtt   240
tcaggctacc aatccacagc ctgctatatt tgttggatac ttaccttttc tttacaatga   300
agtgatacta attgaaatgg tctaaatctg atatctatat ttctccgtct ttcctccccc   360
tcatgatgaa atgcag                                                    376
```

<210> SEQ ID NO 10
<211> LENGTH: 172
<212> TYPE: DNA
<213> ORGANISM: Solanum tuberosum

<400> SEQUENCE: 10

```
gtaaaatcat ctaaagttga aagtgttggg tttatgaagt gctttaattc tatccaagga     60
caagtagaaa cctttttacc ttccattct tgatgatgga tttcatatta tttaatccaa    120
tagctggtca aattcggtaa tagctgtact gattagttac ttcactttgc ag            172
```

<210> SEQ ID NO 11
<211> LENGTH: 145
<212> TYPE: DNA
<213> ORGANISM: Solanum tuberosum

<400> SEQUENCE: 11

```
gtatatatgt tttacttatc catgaaatta ttgctctgct tgttttaat gtactgaaca      60
agttttatgg agaagtaact gaaacaaatc attttcacat tgtctaattt aactcttttt    120
tctgatcctc gcatgacgaa aacag                                          145
```

<210> SEQ ID NO 12
<211> LENGTH: 242
<212> TYPE: DNA
<213> ORGANISM: Solanum tuberosum

<400> SEQUENCE: 12

```
gtaaggattt gcttgaataa cttttgataa taagataaca gatgtagggt acagttctct     60
caccaaaaag aactgtaatt gtctcatcca tctttagttg tataagatat ccgactgtct    120
gagttcggaa gtgtttgagc ctcctgccct ccccctgcgt tgtttagcta attcaaaaag    180
gagaaaactg tttattgatg atctttgtct tcatgctgac atacaatctg ttctcatgac    240
ag                                                                   242
```

<210> SEQ ID NO 13
<211> LENGTH: 797
<212> TYPE: DNA
<213> ORGANISM: Solanum tuberosum

<400> SEQUENCE: 13

```
gtacagttct tgccgtgtga cctccctttt tattgtggtt ttgttcatag ttatttgaat     60
gcgatagaag ttaactattg attaccgcca caatcgccag ttaagtcctc tgaactacta    120
atttgaaagg taggaatagc cgtaataagg tctacttttg gcatcttact gttacaaaac    180
aaaaggatgc caaaaaatt cttctctatc ctctttttcc ctaaaccagt gcatgtagct    240
tgcacctgca taaacttagg taaatgatca aaatgaagt tgatgggaac ttaaaaccgc    300
cctgaagtaa agctaggaat agtcatataa tgtccaccct tggtgtctgc gctaacatca    360
acaacaacat acctcgtgta gtcccacaaa gtggtttcag ggggagggta gagtgtatgc    420
aaaacttact cctatctcag aggtagagag gattttttca atagacccct ggctcaagaa    480
aaaaagtcca aaaagaagta acagaagtga aagcaacatg tgtagctaaa gcgacccaac    540
ttgtttggga ctgaagtagt tgttgttgtt gaaacagtgc atgtagatga acacatgtca    600
gaaaatggac aacacagtta ttttgtgcaa gtcaaaaaaa tgtactacta tttctttgtg    660
cagctttatg tatagaaaag ttaaataact aatgaatttt gctagcagaa aaatagcttg    720
gagagaaatt tttatattg aactaagcta actatattca tctttctttt tgcttcttct    780
tctccttgtt tgtgaag                                                  797
```

<210> SEQ ID NO 14
<211> LENGTH: 2169
<212> TYPE: DNA
<213> ORGANISM: Solanum tuberosum

<400> SEQUENCE: 14

```
atcatggcca attactggtt caaatgcatt acttcctttc agattctttc gagttctcat     60
gaccggtcct actacagacg atactaaccc gtggaactgt tgcatctgct tcttagaact    120
```

-continued

```
ctatggctat tttcgttagc ttggcgtcgg tttgaacata gttttgttt tcaaactctt      180
catttacagt caaaatgttg tatggttttt gttttcctca atgatgttta cagtgttgtg      240
ttgtcatctg tacttttgcc tattacttgt tttgagttac atgttaaaaa agtgtttatt      300
ttgccatatt ttgttctctt attattatta tcatacatac attattacaa ggaaaagaca      360
agtacacaga tcttaacgtt tatgttcaat caacttttgg aggcattgac aggtaccaca      420
aattttgagt ttatgattaa gttcaatctt agaatatgaa tttaacatct attatagatg      480
cataaaaata gctaatgata gaacattgac atttggcaga gcttagggta tggtatatcc      540
aacgttaatt tagtaatttt tgttacgtac gtatatgaaa tattgaatta atcacatgaa      600
cggtggatat tatattatga gttggcatca gcaaaatcat tggtgtagtt gactgtagtt      660
gcagatttaa taataaaatg gtaattaacg gtcgatatta aaataactct catttcaagt      720
gggattagaa ctagttatta aaaaaatgta tactttaagt gatttgatgg catataattt      780
aaagttttc atttcatgct aaaattgtta attattgtaa tgtagactgc gactggaatt      840
attatagtgt aaatttatgc attcagtgta aaattaaagt attgaacttg tctgttttag      900
aaaatacttt atactttaat ataggatttt gtcatgcgaa tttaaattaa tcgatattga      960
acacggaata ccaaaattaa aaaggataca catggccttc atatgaaccg tgaacctttg     1020
ataacgtgga agttcaaaga aggtaaagtt taagaataaa ctgacaaatt aatttctttt     1080
atttggccca ctactaaatt tgctttactt tctaacatgt caagttgtgc cctcttagtt     1140
gaatgatatt cattttcat cccataagtt caatttgatt gtcataccac ccatgatgtt     1200
ctgaaaaatg cttggccatt cacaaagttt atcttagttc ctatgaactt tataagaagc     1260
tttaatttga catgttattt atattagatg atataatcca tgacccaata gacaagtgta     1320
ttaatattgt aactttgtaa ttgagtgtgt ctacatctta ttcaatcatt taaggtcatt     1380
aaaataaatt attttttgac attctaaaac tttaagcaga ataaatagtt tatcaattat     1440
taaaaacaaa aaacgactta tttataaatc aacaaacaat tttagattgc tccaacatat     1500
ttttccaaat taaatgcaga aaatgcataa ttttatactt gatctttata gcttatttt      1560
tttagcctaa ccaacgaata tttgtaaact cacaacttga ttaaaaggga tttacaacaa     1620
gatatatata agtagtgaca aatcttgatt ttaaatattt taatttggag gtcaaaattt     1680
taccataatc atttgtattt ataattaaat tttaaatatc ttatttatac atatctagta     1740
aacttttaaa tatacgtata tacaaaatat aaaattattg gcgttcatat taggtcaata     1800
aatccttaac tatatctgcc ttaccactag gagaaagtaa aaaactcttt accaaaaata     1860
catgtattat gtatacaaaa agtcgattag attacctaaa tagaaattgt ataacgagta     1920
agtaagtaga aatataaaaa aactacaata ctaaaaaaaa tatgttttac ttcaatttcg     1980
aaactaatgg ggtctgagtg aaatattcag aaagggagg actaacaaaa gggtcataat      2040
gtttttttat aaaaagccac taaaatgagg aaatcaagaa tcagaacata caagaaggca     2100
gcagctgaag caaagtacca taatttaatc aatggaaatt aatttcaaag ttttatcaaa     2160
acccattcg                                                             2169
```

<210> SEQ ID NO 15
<211> LENGTH: 1165
<212> TYPE: DNA
<213> ORGANISM: Solanum tuberosum

<400> SEQUENCE: 15

-continued

```
ctgtcaaaga aattctcgag gttacatgga tatcttgaga acttaagaaa ttttacagta      60
taattgaaca agtatatgca gcatatccta atttctggac tgactggtag ccataaactg     120
aatttgaatt catagaaatt attggagtag cgtttgagct tctcaaggtc catacaaaga     180
acacattctc aactatccgt ctcataggat acaacatttt caattgcagt tcaacaccaa     240
aaaaatgtaa aaaatagaaa catcatgacc aggtaatcaa aacatactcg ttcgatacgg     300
aatctattat tggtacattt aaaaggctag aaaaaacaaa cttcagtagc tatctcagca     360
ttataactta ttatgtttcc agcaaaagcc ataacaaatc ttatataact ttcacaaaga     420
aacaattttt atcatatccc tggacatata atgaacccttt tatgtgttca gaactttgcc     480
cttgaccatg tatttgtgtt gtaaaaaatc cacttattat gtatacataa ttgatttaca     540
acaacaaaca caatgtaatc ccacaagtgg agtgtggtga ggactttacc cctaccttac     600
gagatagaga gattgtttct aatagaccct cggctaaagt aaaagcattt caaagcaacg     660
cgaatataaa gaaggcatga taaaacacta aggaagcat gctagagcat tcttaccgag      720
gaacaataac tacgacaaga tatataatac aataatcgaa gtacaagaaa cagaaaatag     780
aataacaaag atcaaataac aaaacaagaa actacccaaa taattccacg actactagta     840
tgaaaggata agccagacaa cactcaaata cctaactaac cttctacccc tcatccgtgt     900
cctccataac ctcctagaac actctttcta aatattgtct tcccccaccc ccctccatc     960 tctcaattt tgaatttat acactcaacc accttgcaaa tttgtcacat gatacttaca     1020
tatggctcta caagtgtcat ttttcttcca tatttgatat tataaaaat aaaataaaaa     1080 actaaggaga tgatccagat atattggaaa atgaaatgca aaggctaaaa ataattgaaa     1140
ttaacatgaa attagtaaaa attac                                          1165
```

<210> SEQ ID NO 16
<211> LENGTH: 317
<212> TYPE: DNA
<213> ORGANISM: Solanum tuberosum

<400> SEQUENCE: 16

```
gcaagcaatg caccacagtt agtttatatc aaaagaaga aggtattaa cggagctaaa      60 aactgttata taccacatga agaagttga taatgtgaaa acaccatgct cataaagatt     120
gtaattcaaa taacaaatgc ccacaggagt aaagagctgt ctttcccaag ttaaggtatt     180
ataaattggc ggaacgaagt aacacatgtt tgacatctcc acacggtgca cagatcaaat     240
atgccatgag caccagtcca gaagttttcc aactatttat atactatcca tgcaaccata     300
taaattatca aacatac                                                   317
```

<210> SEQ ID NO 17
<211> LENGTH: 504
<212> TYPE: DNA
<213> ORGANISM: Solanum tuberosum

<400> SEQUENCE: 17

```
ctgcaaaaaa agagagcagt ttacacaaga aaaaactgct aaatctcaac aaaagtatca      60
tgaatttaat attaaggaag ctatttcgaa cagaaagagt aactcatgat aatagaagga     120
aattgtgaag caacagaagg aagactttct ttatttctac aaaattgctt taagactata     180
tttgatgctt gtatagtaca tgttgaatcc cctcagcttc tttatgtcta actttttttt     240
atattttgaa tctccttagt gaaaatcttt gctttgccac tgacactccg ggggtgtgtc     300
acttctccaa aaaccttgtc tactttttg aagacccaat caaacagctt tttaaaagat     360
```

```
caaaaaaatg gccaggtgcc acctaaatgg agccactact tactccccgg tatgcaaaat      420
tctctagcaa agtcaaagta ggtataaaca attcatcttc caaataaagg tcaaactgcc      480
taaagcacaa cttttggctg ttac                                             504
```

<210> SEQ ID NO 18
<211> LENGTH: 146
<212> TYPE: DNA
<213> ORGANISM: Solanum tuberosum

<400> SEQUENCE: 18

```
ctgcattgtg gatgagttaa ttagaagcat aaccttaata gcaattagaa catgtaagaa       60
agccaatgat gctgcaacat catgctttaa taggaaaatc tgttatgatg atggaaacta      120
ctattttgta gtagacgagg acctac                                           146
```

<210> SEQ ID NO 19
<211> LENGTH: 218
<212> TYPE: DNA
<213> ORGANISM: Solanum tuberosum

<400> SEQUENCE: 19

```
ctgtttaatt gctgaagtag taagttctca agcacttata gaattgactc attttgttaa       60
gggaaagagt atgggatcaa gtccaaatta gtaaagacac aattattta  acttttgcat      120 ttcaaaatgt cttacataac aagactagta agaacatgaa tcgaaatgcc tgtgatgatg      180
gtgttcaaaa ttcagcttca agtatgaat  aacaaaac                             218
```

<210> SEQ ID NO 20
<211> LENGTH: 198
<212> TYPE: DNA
<213> ORGANISM: Solanum tuberosum

<400> SEQUENCE: 20

```
ctgtatccag cagacataat aggagtgaac ataaaaatgt cactggataa ataacttatc       60
atgatattca gcggctacca atattctgaa ggcccatggc gaaaataagt acttttatac      120
tttcaggacg tatatatttg gattctatct aacaattgtt ctgagaatta tttagttgta      180
gaaataaatt taaaatac                                                   198
```

<210> SEQ ID NO 21
<211> LENGTH: 208
<212> TYPE: DNA
<213> ORGANISM: Solanum tuberosum

<400> SEQUENCE: 21

```
ctgtggttag aagctaaaag tgaatagatg agaaaaatta cctccaaata agagggatat       60 tgaaaagaa  acacaatgca tgaaagaat  aaacaaatga taaacgagaa aattgaataa      120
tccatcagaa ccctggttac ctcacaaaga gtgagatttt ccgtggctaa cctatatgaa      180
ccttaaaatg caatagaaac agacaaac                                         208
```

<210> SEQ ID NO 22
<211> LENGTH: 293
<212> TYPE: DNA
<213> ORGANISM: Solanum tuberosum

<400> SEQUENCE: 22

```
ctgtacaagt tcatcaaaca tttcacaatt actccaaaac agacacactt gcaaactcta       60
```

-continued

```
tacagtaatc ttctatacta caaaaaagta aacaatgttt tttttaagat gacatttgtt    120
ctcagcaaca taatagaaat ccctagacaa tggaaacatt catcatgttg ttttcctcta    180
tgtttcaacc cctttgatgt tcaacagttc aggtcatttt gaggaatgaa tcttgttcaa    240
gtaagccaaa ctaattgtaa ttatcacaaa atatctaaag atgtaagaca tac           293
```

<210> SEQ ID NO 23
<211> LENGTH: 376
<212> TYPE: DNA
<213> ORGANISM: Solanum tuberosum

<400> SEQUENCE: 23

```
ctgcatttca tcatgagggg gaggaaagac ggagaaatat agatatcaga tttagaccat     60
ttcaattagt atcacttcat tgtaaagaaa aggtaagtat ccaacaaata tagcaggctg    120
tggattggta gcctgaaact atagcttcaa agaatcaact taagctgctc atcaaggcct    180
tagtggtaga atgaggcgg taataagtgt aaatgaatct aatacttgga tctcgaaaca    240
aaaatcagaa attcggttgg aaaataagta gaacaagatg aaatgagcta tcatccccag    300
aaccaagtag acttccaagt aagcaatcta aaaattacta gattatttaa caagctgcga    360
ttcaaaatac ttgaac                                                    376
```

<210> SEQ ID NO 24
<211> LENGTH: 172
<212> TYPE: DNA
<213> ORGANISM: Solanum tuberosum

<400> SEQUENCE: 24

```
ctgcaaagtg aagtaactaa tcagtacagc tattaccgaa tttgaccagc tattggatta     60
aataatatga aatccatcat caagaaatgg aaggtaaaaa ggtttctact tgtccttgga    120
tagaattaaa gcacttcata aacccaacac tttcaacttt agatgatttt ac             172
```

<210> SEQ ID NO 25
<211> LENGTH: 145
<212> TYPE: DNA
<213> ORGANISM: Solanum tuberosum

<400> SEQUENCE: 25

```
ctgttttcgt catgcgagga tcagaaaaaa gagttaaatt agacaatgtg aaaatgattt     60
gtttcagtta cttctccata aaacttgttc agtacattaa aaacaagcag agcaataatt    120
tcatggataa gtaaaacata tatac                                          145
```

<210> SEQ ID NO 26
<211> LENGTH: 242
<212> TYPE: DNA
<213> ORGANISM: Solanum tuberosum

<400> SEQUENCE: 26

```
ctgtcatgag aacagattgt atgtcagcat gaagacaaag atcatcaata aacagttttc     60
tcctttttga attagctaaa caacgcaggg ggagggcagg aggctcaaac acttccgaac    120
tcagacagtc ggatatctta tacaactaaa gatggatgag acaattacag ttcttttttgg   180 tgagagaact gtaccctaca tctgttatct tattatcaaa agttattcaa gcaaatcctt    240
ac                                                                   242
```

<210> SEQ ID NO 27
<211> LENGTH: 797

<212> TYPE: DNA
<213> ORGANISM: Solanum tuberosum

<400> SEQUENCE: 27

| | | | | | | |
|---|---|---|---|---|---|---|
| cttcacaaac | aaggagaaga | agaagcaaaa | agaaagatga | atatagttag | cttagttcaa | 60 |
| tataaaaaat | ttctctccaa | gctattttc | tgctagcaaa | attcattagt | tatttaactt | 120 |
| ttctatacat | aaagctgcac | aaagaaatag | tagtacattt | ttttgacttg | cacaaaataa | 180 |
| ctgtgttgtc | cattttctga | catgtgttca | tctacatgca | ctgtttcaac | aacaacaact | 240 |
| acttcagtcc | caaacaagtt | gggtcgcttt | agctacacat | gttgctttca | cttctgttac | 300 |
| ttctttttgg | acttttttc | ttgagccaag | ggtctattga | aaaaatcctc | tctacctctg | 360 |
| agataggagt | aagttttgca | tacactctac | cctcccctg | aaaccacttt | gtgggactac | 420 |
| acgaggtatg | ttgttgttga | tgttagcgca | gacaccaaag | gtggacatta | tatgactatt | 480 |
| cctagcttta | cttcagggcg | ttttaagtt | cccatcaact | tcattttga | tcatttacct | 540 |
| aagtttatgc | aggtgcaagc | tacatgcact | ggtttaggga | aaagaggat | agagaagaat | 600 |
| ttttttggca | tccttttgtt | ttgtaacagt | aagatgccaa | agtagacct | tattacggct | 660 |
| attcctacct | ttcaaattag | tagttcagag | gacttaactg | gcgattgtgg | cggtaatcaa | 720 |
| tagttaactt | ctatcgcatt | caaataacta | tgaacaaaac | cacaataaaa | agggaggtca | 780 |
| cacggcaaga | actgtac | | | | | 797 |

<210> SEQ ID NO 28
<211> LENGTH: 2169
<212> TYPE: DNA
<213> ORGANISM: Solanum tuberosum

<400> SEQUENCE: 28

| | | | | | | |
|---|---|---|---|---|---|---|
| cgaatgggtt | ttgataaaac | tttgaaatta | atttccattg | attaaattat | ggtactttgc | 60 |
| ttcagctgct | gccttcttgt | atgttctgat | tcttgatttc | ctcatttag | tggcttttta | 120 |
| taaaaaaca | ttatgaccct | tttgttagtc | ctcccctttc | tgaatatttc | actcagaccc | 180 |
| cattagtttc | gaaattgaag | taaaacatat | tttttttagt | attgtagttt | ttttatattt | 240 |
| ctacttactt | actcgttata | caatttctat | ttaggtaatc | taatcgactt | tttgtataca | 300 |
| taatacatgt | attttggta | aagagttttt | tactttctcc | tagtggtaag | gcagatatag | 360 |
| ttaaggattt | attgacctaa | tatgaacgcc | aataatttta | tattttgtat | atacgtatat | 420 |
| ttaaaagttt | actagatatg | tataaataag | atatttaaaa | tttaattata | aatacaaatg | 480 |
| attatggtaa | aattttgacc | tccaaattaa | aatatttaaa | atcaagattt | gtcactactt | 540 |
| atatatatct | tgttgtaaat | cccttttaat | caagttgtga | gtttacaaat | attcgttggt | 600 |
| taggctaaaa | aaaataagct | ataaagatca | agtataaaat | tatgcatttt | ctgcatttaa | 660 |
| tttgaaaaaa | tatgttggag | caatctaaaa | ttgtttgttg | atttataaat | aagtcgtttt | 720 |
| ttgttttaa | taattgataa | actatttatt | ctgcttaaag | ttttagaatg | tcaaaaaata | 780 |
| atttatttta | atgaccttaa | atgattgaat | aagatgtaga | cacactccaat | tacaaagtta | 840 |
| caatattaat | acacttgtct | attgggtcat | ggattatatc | atctaatata | ataacatgt | 900 |
| caaattaaag | cttcttataa | agttcatagg | aactaagata | aactttgtga | atggccaagc | 960 |
| atttttcaga | acatcatggg | tggtatgaca | atcaaattga | acttatggga | tgaaaaatga | 1020 |
| atatcattca | actaagaggg | cacaacttga | catgttagaa | agtaaagcaa | atttagtagt | 1080 |
| gggccaaata | aaagaaatta | atttgtcagt | ttattcttaa | actttacctt | ctttgaactt | 1140 |

-continued

```
ccacgttatc aaaggttcac ggttcatatg aaggccatgt gtatcctttt taattttggt      1200
attccgtgtt caatatcgat taatttaaat tcgcatgaca aaatcctata ttaaagtata      1260
aagtattttc taaaacagac aagttcaata ctttaatttt acactgaatg cataaattta      1320
cactataata attccagtcg cagtctacat tacaataatt aacaatttta gcatgaaatg      1380
aaaaacttta aattatatgc catcaaatca cttaaagtat acattttttt aataactagt      1440
tctaatccca cttgaaatga gagttatttt aatatcgacc gttaattacc attttattat      1500
taaatctgca actacagtca actacaccaa tgattttgct gatgccaact cataatataa      1560
tatccaccgt tcatgtgatt aattcaatat ttcatatacg tacgtaacaa aaattactaa      1620
attaacgttg gatataccat accctaagct ctgccaaatg tcaatgttct atcattagct      1680 attttatgc atctataata gatgttaaat tcatattcta agattgaact taatcataaa       1740
ctcaaaattt gtggtacctg tcaatgcctc caaagttga ttgaacataa acgttaagat       1800
ctgtgtactt gtcttttcct tgtaataatg tatgtatgat aataataata agagaacaaa      1860
atatggcaaa ataaacactt ttttaacatg taactcaaaa caagtaatag caaaagtac       1920 agatgacaac acaacactgt aaacatcatt gaggaaaaca aaaaccatac aacattttga      1980
ctgtaaatga gagtttgaa acaaaaaact atgttcaaac cgacgccaag ctaacgaaaa       2040
tagccataga gttctaagaa gcagatgcaa cagttccacg ggttagtatc gtctgtagta      2100
ggaccggtca tgagaactcg aaagaatctg aaaggaagta atgcatttga accagtaatt      2160
ggccatgat                                                             2169
```

<210> SEQ ID NO 29
<211> LENGTH: 11469
<212> TYPE: DNA
<213> ORGANISM: Solanum tuberosum
<220> FEATURE:
<221> NAME/KEY: CDS
<222> LOCATION: (2132..2209, 3375..3494, 3812..4033, 4538..4606,
      4753..5022, 5241..6146, 6345..6461, 6670..6732,
      7026..7133, 7510..7611, 7784..7852, 7998..8078,
      8321..8437, 9235..9630)

<400> SEQUENCE: 29

```
atcatggcca attactggtt caaatgcatt acttcctttc agattctttc gagttctcat       60
gaccggtcct actacagacg atactaaccc gtggaactgt tgcatctgct tcttagaact      120
ctatggctat tttcgttagc ttggcgtcgg tttgaacata gttttttgttt tcaaactctt     180 catttacagt caaaatgttg tatggttttt gttttcctca atgatgttta cagtgttgtg      240
ttgtcatctg tacttttgcc tattacttgt tttgagttac atgttaaaaa agtgtttatt      300
ttgccatatt ttgttctctt attattatta tcatacatac attattacaa ggaaaagaca      360
agtacacaga tcttaacgtt tatgttcaat caacttttgg aggcattgac aggtaccaca      420
aattttgagt ttatgattaa gttcaatctt agaatatgaa tttaacatct attatagatg      480
cataaaaata gctaatgata gaacattgac atttggcaga gcttagggta tggtatatcc      540
aacgttaatt tagtaatttt tgttacgtac gtatatgaaa tattgaatta atcacatgaa      600
cggtggatat tatattatga gttggcatca gcaaaatcat tggtgtagtt gactgtagtt      660
gcagatttaa taataaaatg gtaattaacg gtcgatatta aataactct catttcaagt       720 gggattagaa ctagttatta aaaaaatgta tactttaagt gatttgatgg catataattt      780 aaagttttc atttcatgct aaaattgtta attattgtaa tgtagactgc gactggaatt      840
attatagtgt aaatttatgc attcagtgta aaattaaagt attgaacttg tctgtttag      900
```

-continued

```
aaaatacttt atactttaat ataggatttt gtcatgcgaa tttaaattaa tcgatattga      960
acacggaata ccaaaattaa aaaggataca catggccttc atatgaaccg tgaacctttg     1020
ataacgtgga agttcaaaga aggtaaagtt taagaataaa ctgacaaatt aatttctttt     1080
atttggccca ctactaaatt tgctttactt tctaacatgt caagttgtgc cctcttagtt     1140
gaatgatatt cattttcat cccataagtt caatttgatt gtcataccac ccatgatgtt     1200
ctgaaaaatg cttggccatt cacaaagttt atcttagttc ctatgaactt tataagaagc     1260
tttaatttga catgttattt atattagatg atataatcca tgacccaata gacaagtgta     1320
ttaatattgt aactttgtaa ttgagtgtgt ctacatctta ttcaatcatt taaggtcatt     1380
aaaataaatt atttttttgac attctaaaac tttaagcaga ataaatagtt tatcaattat     1440
taaaaacaaa aaacgactta tttataaatc aacaaacaat tttagattgc tccaacatat     1500
ttttccaaat taaatgcaga aaatgcataa ttttatactt gatctttata gcttattttt     1560
tttagcctaa ccaacgaata tttgtaaact cacaacttga ttaaaaggga tttacaacaa     1620
gatatatata agtagtgaca aatcttgatt ttaaatattt taatttggag gtcaaaattt     1680
taccataatc atttgtattt ataattaaat tttaaatatc ttatttatac atatctagta     1740
aacttttaaa tatacgtata tacaaaaatat aaaattattg gcgttcatat taggtcaata     1800
aatccttaac tatatctgcc ttaccactag gagaaagtaa aaaactcttt accaaaaata     1860
catgtattat gtatacaaaa agtcgattag attacctaaa tagaaattgt ataacgagta     1920
agtaagtaga aatataaaaa aactacaata ctaaaaaaaa tatgttttac ttcaatttcg     1980
aaactaatgg ggtctgagtg aaatattcag aaaggggagg actaacaaaa gggtcataat     2040 gttttttttat aaaaagccac taaaatgagg aaatcaagaa tcagaacata caagaaggca     2100
gcagctgaag caaagtacca taatttaatc a atg gaa att aat ttc aaa gtt        2152
                                    Met Glu Ile Asn Phe Lys Val
                                     1               5 tta tca aaa ccc att cga gga tct ttt cca tct ttc tca cct aaa gtt       2200
Leu Ser Lys Pro Ile Arg Gly Ser Phe Pro Ser Phe Ser Pro Lys Val
    10                  15                  20 tct tca ggg gtaattttta ctaatttcat gttaatttca attattttta               2249
Ser Ser Gly
        25 gcctttgcat ttcattttcc aatatatctg gatcatctcc ttagtttttt attttatttt     2309 ttataatatc aaatatggaa gaaaaatgac acttgtagag ccatatgtaa gtatcatgtg     2369 acaaatttgc aagtggttg agtgtataaa attcaaaaat tgagagatgg agggggggtg      2429 ggggaagaca atatttagaa agagtgttct aggaggttat ggaggacacg gatgaggggt     2489 agaaggttag ttaggtattt gagtgttgtc tggcttatcc tttcatacta gtagtcgtgg     2549 aattatttgg gtagtttctt gttttgttat ttgatctttg ttattctatt ttctgtttct     2609 tgtacttcga ttattgtatt atatatcttg tcgtagttat tgttcctcgg taagaatgct     2669 ctagcatgct tcctttagtg ttttatcatg ccttctttat attcgcgttg ctttgaaatg     2729 cttttacttt agccgagggt ctattagaaa caatctctct atctcgtaag gtagggtaa     2789 agtcctcacc acactccact tgtgggatta cattgtgttt gttgttgtaa atcaattatg     2849 tatacataat aagtggattt tttacaacac aaatacatgg tcaagggcaa agttctgaac     2909 acataaaggg ttcattatat gtccagggat atgataaaaa ttgtttcttt gtgaaagtta     2969 tataagattt gttatggctt ttgctggaaa cataataagt tataatgctg agatagctac     3029
```

-continued

```
tgaagtttgt tttttctagc cttttaaatg taccaataat agattccgta tcgaacgagt      3089
atgttttgat tacctggtca tgatgtttct attttttaca ttttttggt gttgaactgc       3149 aattgaaaat gttgtatcct atgagacgga tagttgagaa tgtgttcttt gtatggacct      3209
tgagaagctc aaacgctact ccaataattt ctatgaattc aaattcagtt tatggctacc     3269
agtcagtcca gaaattagga tatgctgcat atacttgttc aattatactg taaaatttct     3329
taagttctca agatatccat gtaacctcga gaatttcttt gacag gct tct aga          3383
                                                  Ala Ser Arg aat aag ata tgt ttt cct tct caa cat agt act gga ctg aag ttt gga       3431
Asn Lys Ile Cys Phe Pro Ser Gln His Ser Thr Gly Leu Lys Phe Gly
 30              35                  40                  45 tct cag gaa cgg tct tgg gat att tct tcc acc cca aaa tca aga gtt       3479
Ser Gln Glu Arg Ser Trp Asp Ile Ser Ser Thr Pro Lys Ser Arg Val
             50                  55                  60 aga aaa gat gaa agg gtatgtttga taattatat ggttgcatgg atagtatata        3534
Arg Lys Asp Glu Arg
             65
aatagttgga aaacttctgg actggtgctc atggcatatt tgatctgtgc accgtgtgga     3594
gatgtcaaac atgtgttact tcgttccgcc aatttataat accttaactt gggaaagaca    3654
gctctttact cctgtgggca tttgttattt gaattacaat ctttatgagc atggtgtttt    3714
cacattatca acttctttca tgtggtatat aacagttttt agctccgtta atacctttct   3774 tcttttgat ataaactaac tgtggtgcat tgcttgc atg aag cac agt tca gct      3829
                                        Met Lys His Ser Ser Ala
                                                            70 att tcc gct gtt ttg acc gat gac gac aat tcg aca atg gca ccc cta      3877
Ile Ser Ala Val Leu Thr Asp Asp Asp Asn Ser Thr Met Ala Pro Leu
         75                  80                  85 gag gaa gat gtc aag act gaa aat att ggc ctc cta aat ttg gat cca      3925
Glu Glu Asp Val Lys Thr Glu Asn Ile Gly Leu Leu Asn Leu Asp Pro
 90              95                  100 act ttg gaa cct tat cta gat cac ttc aga cac aga atg aag aga tat      3973
Thr Leu Glu Pro Tyr Leu Asp His Phe Arg His Arg Met Lys Arg Tyr
105             110                 115                 120 gtg gat cag aaa atg ctc att gaa aaa tat gag gga ccc ctt gag gaa      4021
Val Asp Gln Lys Met Leu Ile Glu Lys Tyr Glu Gly Pro Leu Glu Glu
                125                 130                 135 ttt gct caa ggt aacagccaaa agttgtgctt taggcagttt gaccttattt          4073
Phe Ala Gln Gly
            140 tggaagatga attgtttata cctactttga ctttgctaga gaattttgca taccggggag    4133 taagtagtgg ctccatttag gtggcacctg gccattttt tgatcttta aaaagctgtt     4193 tgattgggtc ttcaaaaaag tagacaaggt ttttggagaa gtgacacacc cccggagtgt    4253 cagtggcaaa gcaaagattt tcactaagga gattcaaaat ataaaaaaag tatagacata   4313 aagaagctga ggggattcaa catgtactat acaagcatca aatatagtct taaagcaatt   4373 ttgtagaaat aaagaaagtc ttccttctgt tgcttcacaa tttccttcta ttatcatgag   4433 ttactctttc tgttcgaaat agcttcctta atattaaatt catgatactt tgttgagat    4493 ttagcagttt tttcttgtgt aaactgctct ctttttttgc aggt tat tta aaa ttt    4549
                                                Tyr Leu Lys Phe gga ttc aac agg gaa gat ggt tgc ata gtc tat cgt gaa tgg gct cct      4597

Gly Phe Asn Arg Glu Asp Gly Cys Ile Val Tyr Arg Glu Trp Ala Pro
145             150                 155                 160 gct gct cag taggtcctcg tctactacaa aatagtagtt tccatcatca              4646
```

```
Ala Ala Gln taacagattt tcctattaaa gcatgatgtt gcagcatcat tggctttctt acatgttcta      4706
attgctatta aggttatgct tctaattaac tcatccacaa tgcagg gaa gca gaa         4761
                                                  Glu Ala Glu
                                                          165 gtt att ggc gat ttc aat gga tgg aac ggt tct aac cac atg atg gag        4809
Val Ile Gly Asp Phe Asn Gly Trp Asn Gly Ser Asn His Met Met Glu
        170                 175                 180 aag gac cag ttt ggt gtt tgg agt att aga att cct gat gtt gac agt        4857
Lys Asp Gln Phe Gly Val Trp Ser Ile Arg Ile Pro Asp Val Asp Ser
            185                 190                 195 aag cca gtc att cca cac aac tcc aga gtt aag ttt cgt ttc aaa cat        4905
Lys Pro Val Ile Pro His Asn Ser Arg Val Lys Phe Arg Phe Lys His
200                 205                 210 ggt aat gga gtg tgg gta gat cgt atc cct gct tgg ata aag tat gcc        4953
Gly Asn Gly Val Trp Val Asp Arg Ile Pro Ala Trp Ile Lys Tyr Ala
215                 220                 225                 230 act gca gac gcc aca aag ttt gca gca cca tat gat ggt gtc tac tgg        5001
Thr Ala Asp Ala Thr Lys Phe Ala Ala Pro Tyr Asp Gly Val Tyr Trp
                235                 240                 245 gac cca cca cct tca gaa agg ttttgttatt catccttga agctgaattt            5052
Asp Pro Pro Pro Ser Glu Arg
            250 tgaacaccat catcacaggc atttcgattc atgttcttac tagtcttgtt atgtaagaca      5112 ttttgaaatg caaaagttaa aataattgtg tctttactaa tttggacttg atcccatact      5172 ctttcccttta acaaaatgag tcaattctat aagtgcttga aacttacta cttcagcaat      5232 taaacagg tac cac ttc aaa tac cct cgc cct ccc aaa ccc cga gcc cca       5282
         Tyr His Phe Lys Tyr Pro Arg Pro Pro Lys Pro Arg Ala Pro
             255                 260                 265 cga atc tat gaa gca cat gtc ggc atg agc agc tct gag cca cgt gta        5330
Arg Ile Tyr Glu Ala His Val Gly Met Ser Ser Ser Glu Pro Arg Val
        270                 275                 280 aat tcg tat cgt gag ttt gca gat gat gtt tta cct cgg att aag gca        5378
Asn Ser Tyr Arg Glu Phe Ala Asp Asp Val Leu Pro Arg Ile Lys Ala
    285                 290                 295 aat aac tat aat act gtc cag ttg atg gcc ata atg gaa cat tct tac        5426
Asn Asn Tyr Asn Thr Val Gln Leu Met Ala Ile Met Glu His Ser Tyr
300                 305                 310                 315 tat gga tca ttt gga tat cat gtt aca aac ttt ttt gct gtg agc agt        5474
Tyr Gly Ser Phe Gly Tyr His Val Thr Asn Phe Phe Ala Val Ser Ser
                320                 325                 330 aga tat gga aac ccg gag gac cta aag tat ctg ata gat aaa gca cat        5522
Arg Tyr Gly Asn Pro Glu Asp Leu Lys Tyr Leu Ile Asp Lys Ala His
                335                 340                 345 agc ttg ggt tta cag gtt ctg gtg gat gta gtt cac agt cat gca agc        5570
Ser Leu Gly Leu Gln Val Leu Val Asp Val Val His Ser His Ala Ser
        350                 355                 360 aat aat gtc act gat ggc ctc aat ggc ttt gat att ggc caa ggt tct        5618
Asn Asn Val Thr Asp Gly Leu Asn Gly Phe Asp Ile Gly Gln Gly Ser
365                 370                 375 caa gaa tcc tac ttt cat gct gga gag cga ggg tac cat aag ttg tgg        5666
Gln Glu Ser Tyr Phe His Ala Gly Glu Arg Gly Tyr His Lys Leu Trp
380                 385                 390                 395 gat agc agg ctg ttc aac tat gcc aat tgg gag gtt ctt cgt ttc ctt        5714
Asp Ser Arg Leu Phe Asn Tyr Ala Asn Trp Glu Val Leu Arg Phe Leu
                400                 405                 410 ctt tcc aac ttg agg tgg tgg cta gaa gag tat aac ttt gac gga ttt        5762
```

```
                                                                -continued

Leu Ser Asn Leu Arg Trp Trp Leu Glu Glu Tyr Asn Phe Asp Gly Phe
            415                 420                 425 cga ttt gat gga ata act tct atg ctg tat gtt cat cat gga atc aat    5810
Arg Phe Asp Gly Ile Thr Ser Met Leu Tyr Val His His Gly Ile Asn
            430                 435                 440 atg gga ttt aca gga aac tat aat gag tat ttc agc gag gct aca gat    5858
Met Gly Phe Thr Gly Asn Tyr Asn Glu Tyr Phe Ser Glu Ala Thr Asp
            445                 450                 455 gtt gat gct gtg gtc tat tta atg ttg gcc aat aat ctg att cac aag    5906
Val Asp Ala Val Val Tyr Leu Met Leu Ala Asn Asn Leu Ile His Lys
460                 465                 470                 475 att ttc cca gat gca act gtt att gcc gaa gat gtt tct ggt atg ccg    5954
Ile Phe Pro Asp Ala Thr Val Ile Ala Glu Asp Val Ser Gly Met Pro
                480                 485                 490 ggc ctt ggc cgg cct gtt tct gag gga gga att ggt ttt gtt tac cgc    6002
Gly Leu Gly Arg Pro Val Ser Glu Gly Gly Ile Gly Phe Val Tyr Arg
                495                 500                 505 ctg gca atg gca atc cca gat aag tgg ata gat tat tta aag aat aag    6050
Leu Ala Met Ala Ile Pro Asp Lys Trp Ile Asp Tyr Leu Lys Asn Lys
                510                 515                 520 aat gat gaa gat tgg tcc atg aag gaa gta aca tcg agt ttg aca aat    6098
Asn Asp Glu Asp Trp Ser Met Lys Glu Val Thr Ser Ser Leu Thr Asn
525                 530                 535 agg aga tat aca gag aag tgt ata gca tat gcg gag acc cat gat cag    6146
Arg Arg Tyr Thr Glu Lys Cys Ile Ala Tyr Ala Glu Thr His Asp Gln
540                 545                 550                 555 gtattttaaa tttatttcta caactaaata attctcagaa caattgttag atagaatcca  6206
aatatatacg tcctgaaagt ataaaagtac ttattttcgc catgggcctt cagaatattg  6266
gtagccgctg aatatcatga taagttattt atccagtgac attttatgt tcactcctat   6326 tatgtctgct ggatacag tct att gtt ggt gac aag acc att gca ttt ctc    6377
                 Ser Ile Val Gly Asp Lys Thr Ile Ala Phe Leu
                                 560                 565 cta atg gac aaa gag atg tat tct ggc atg tct tgc ttg aca gat gct    6425
Leu Met Asp Lys Glu Met Tyr Ser Gly Met Ser Cys Leu Thr Asp Ala
            570                 575                 580 tct cct gtt gtt gat cga gga att gcg ctt cac aag gtttgtctgt         6471
Ser Pro Val Val Asp Arg Gly Ile Ala Leu His Lys
            585                 590 ttctattgca ttttaaggtt catataggtt agccacggaa aatctcactc tttgtgaggt  6531
aaccagggtt ctgatggatt attcaattt ctcgtttatc atttgtttat tcttttcatg   6591
cattgtgttt cttttcaat atccctctta tttggaggta attttctca tctattcact    6651 tttagcttct aaccacag atg atc cat ttt ttc aca atg gcc ttg gga gga    6702
                 Met Ile His Phe Phe Thr Met Ala Leu Gly Gly
                         595                 600                 605 gag ggg tac ctc aat ttc atg ggt aac gag gtatgtctta catctttaga     6752
Glu Gly Tyr Leu Asn Phe Met Gly Asn Glu
                610                 615 tatttttgtga taattacaat tagtttggct tacttgaaca agattcattc ctcaaaatga 6812 cctgaactgt tgaacatcaa aggggttgaa acatagagga aaacaacatg atgaatgttt  6872
ccattgtcta gggatttcta ttatgttgct gagaacaaat gtcatcttaa aaaaaacatt  6932
gtttactttt ttgtagtata aagattact gtatagagtt tgcaagtgtg tctgttttgg   6992
agtaattgtg aaatgtttga tgaacttgta cag ttt ggc cat cct gag tgg att   7046
                                 Phe Gly His Pro Glu Trp Ile
                                                     620
```

-continued

```
gac ttc cct aga gag ggc aat aat tgg agt tat gac aaa tgt aga cgc      7094
Asp Phe Pro Arg Glu Gly Asn Asn Trp Ser Tyr Asp Lys Cys Arg Arg
        625                 630                 635 cag tgg aac ctc gcg gat agc gaa cac ttg aga tac aag gttcaagtat       7143
Gln Trp Asn Leu Ala Asp Ser Glu His Leu Arg Tyr Lys
    640                 645                 650 tttgaatcgc agcttgttaa ataatctagt aatttttaga ttgcttactt ggaagtctac    7203
ttggttctgg ggatgatagc tcatttcatc ttgttctact tattttccaa ccgaatttct    7263
gatttttgtt tcgagatcca agtattagat tcatttacac ttattaccgc ctcatttcta    7323
ccactaaggc cttgatgagc agcttaagtt gattctttga agctatagtt tcaggctacc    7383
aatccacagc ctgctatatt tgttggatac ttaccttttc tttacaatga agtgatacta    7443
attgaaatgg tctaaatctg atatctatat ttctccgtct ttcctccccc tcatgatgaa    7503 atgcag ttt atg aat gca ttt gat aga gct atg aat tcg ctc gat gaa      7551
        Phe Met Asn Ala Phe Asp Arg Ala Met Asn Ser Leu Asp Glu
            655                 660                 665 aag ttc tca ttc ctc gca tca gga aaa cag ata gta agc agc atg gat     7599
Lys Phe Ser Phe Leu Ala Ser Gly Lys Gln Ile Val Ser Ser Met Asp
        670                 675                 680 gat gat aat aag gtaaaatcat ctaaagttga aagtgttggg tttatgaagt         7651
Asp Asp Asn Lys
            685 gctttaattc tatccaagga caagtagaaa ccttttttacc ttccatttct tgatgatgga   7711 tttcatatta tttaatccaa tagctggtca aattcggtaa tagctgtact gattagttac   7771 ttcactttgc ag gtt gtt gtg ttt gaa cgt ggt gac ctg gta ttt gta       7819
              Val Val Val Phe Glu Arg Gly Asp Leu Val Phe Val
                                690                 695 ttc aac ttc cac cca aag aac aca tac gaa ggg tatatatgtt ttacttatcc   7872
Phe Asn Phe His Pro Lys Asn Thr Tyr Glu Gly
        700                 705 atgaaattat tgctctgctt gttttttaatg tactgaacaa gttttatgga gaagtaactg   7932
aaacaaatca ttttcacatt gtctaattta actcttttttt ctgatcctcg catgacgaaa   7992 acagg tat aaa gtt gga tgt gac ttg cca ggg aag tac aga gtt gca       8039
      Tyr Lys Val Gly Cys Asp Leu Pro Gly Lys Tyr Arg Val Ala
          710                 715                 720 ctg gac agt gat gct tgg gaa ttt ggt ggc cat gga aga gtaaggattt      8088
Leu Asp Ser Asp Ala Trp Glu Phe Gly Gly His Gly Arg
        725                 730                 735 gcttgaataa cttttgataa taagataaca gatgtagggt acagttctct caccaaaaag   8148
aactgtaatt gtctcatcca tctttagttg tataagatat ccgactgtct gagttcggaa   8208
gtgtttgagc ctcctgccct cccctgcgt tgtttagcta attcaaaaag gagaaaactg    8268
tttattgatg atctttgtct tcatgctgac atacaatctg ttctcatgac ag act       8323
                                                            Thr ggt cat gat gtt gac cat ttc aca tca cca gaa gga ata cct gga gtt     8371
Gly His Asp Val Asp His Phe Thr Ser Pro Glu Gly Ile Pro Gly Val
        740                 745                 750 cca gaa aca aat ttc aat ggt cgt cca aat tcc ttc aaa gtg ctg tct    8419
Pro Glu Thr Asn Phe Asn Gly Arg Pro Asn Ser Phe Lys Val Leu Ser
        755                 760                 765 cct gcg cga aca tgt gtg gtacagttct tgccgtgtga cctcccttttt          8467
Pro Ala Arg Thr Cys Val
    770 tattgtggtt ttgttcatag ttatttgaat gcgatagaag ttaactattg attaccgcca    8527
```

```
caatcgccag ttaagtcctc tgaactacta atttgaaagg taggaatagc cgtaataagg    8587
tctacttttg gcatcttact gttacaaaac aaaaggatgc caaaaaaatt cttctctatc    8647 ctcttttttcc ctaaaccagt gcatgtagct tgcacctgca taaacttagg taaatgatca   8707
aaaatgaagt tgatgggaac ttaaaaccgc cctgaagtaa agctaggaat agtcatataa    8767
tgtccacctt tggtgtctgc gctaacatca acaacaacat acctcgtgta gtcccacaaa   8827
gtggtttcag ggggagggta gagtgtatgc aaaacttact cctatctcag aggtagagag    8887 gatttttttca atagacccttt ggctcaagaa aaaagtccaa aaagaagta acagaagtga   8947 aagcaacatg tgtagctaaa gcgacccaac ttgtttggga ctgaagtagt tgttgttgtt    9007
gaaacagtgc atgtagatga acacatgtca gaaaatggac aacacagtta ttttgtgcaa    9067
gtcaaaaaaa tgtactacta tttctttgtg cagctttatg tatagaaaag ttaaataact    9127
aatgaatttt gctagcagaa aaatagcttg gagagaaatt ttttatattg aactaagcta    9187
actatattca tctttctttt tgcttcttct tctccttgtt tgtgaag gct tat tac     9243
                                                  Ala Tyr Tyr
                                                          775 aga gtt gat gaa cgc atg tca gaa act gaa gat tac cag aca gac att     9291
Arg Val Asp Glu Arg Met Ser Glu Thr Glu Asp Tyr Gln Thr Asp Ile
        780                 785                 790 tgt agt gag cta cta cca aca gcc aat atc gag gag agt gac gag aaa     9339
Cys Ser Glu Leu Leu Pro Thr Ala Asn Ile Glu Glu Ser Asp Glu Lys
795                 800                 805 ctt aaa gat tcg tta tct aca aat atc agt aac att gac gaa cgc atg     9387
Leu Lys Asp Ser Leu Ser Thr Asn Ile Ser Asn Ile Asp Glu Arg Met
810                 815                 820                 825 tca gaa act gaa gtt tac cag aca gac att tct agt gag cta cta cca     9435
Ser Glu Thr Glu Val Tyr Gln Thr Asp Ile Ser Ser Glu Leu Leu Pro
        830                 835                 840 aca gcc aat att gag gag agt gac gag aaa ctt aaa gat tcg tta tct     9483
Thr Ala Asn Ile Glu Glu Ser Asp Glu Lys Leu Lys Asp Ser Leu Ser
            845                 850                 855 aca aat atc agt aac att gat cag act gtt gta gtt tct gtt gag gag     9531
Thr Asn Ile Ser Asn Ile Asp Gln Thr Val Val Val Ser Val Glu Glu
            860                 865                 870 aga gac aag gaa ctt aaa gat tca ccg tct gta agc atc att agt gat     9579
Arg Asp Lys Glu Leu Lys Asp Ser Pro Ser Val Ser Ile Ile Ser Asp
    875                 880                 885 gtt gtt cca gct gaa tgg gat gat tca gat gca aac gtc tgg ggt gag    9627
Val Val Pro Ala Glu Trp Asp Asp Ser Asp Ala Asn Val Trp Gly Glu
890                 895                 900                 905 gac tagtcagatg attgatcgac ccttctaccg attggtgatc gctatccttg           9680
Asp ctctctgaga aataggtgag gcgaaacaaa aaataatttg catgataaaa agtctgattt    9740
tatgatcgct atcctcgctc tctgagaaag aagcgaaaca aaggcgactc ctggactcga    9800
atctataaga taacaaaggc gactcctggg actcgaatct ataagataac aaaggcaatt    9860
ccaagacttg aatctataaa aaatttagtt aagaatgatt aacgtccgat cctaattcga    9920
atcgaggcat cttaccactc cattgataat tatataagtc aataagtcat ataaagtatt    9980
aaaaactaaa ttgacttgat cggtctatca aaaatagata aattgtgttc atatgtaaca   10040
tttttgttgt cacaattagc ttaattacat cttctcatgtg caataacaaa gaaatgatag   10100
gaatttagag attccaatttt ttttgttgcc acaattaact taattacatc tttcatttgc  10160
aataacaaag aaatgatagg aatttagaga tccagtgtca atacacaacc taggccaaca   10220
```

-continued

```
tcgaaagcat aactgtaaac tcatgcatga agaaatcagt cgtaaaaatg aataaatgcg   10280
acataaaaac aaattgcatg tatcattaat gtgacttaac tacaagtaaa aataaattta   10340
acaaatgtaa cttaactaca agtaaaaata aattgcttct atcattaaca acaaacaga    10400 attaaaaaga aaaaaacata ctaaatctta ccgtcattcg ataaaaaaaa ataccaaatt   10460
cataatgcaa ggaaaacgaa acgcgtcctg atcgggtatc aacgatgaaa tggaccagtt   10520
ggatcgactg cctgcacaac gttaggtatg ccaaaaaaaa gaacacgatc ctttgcaccc   10580
gttcgatgat tatcagtatg ttcacaaaaa aacttaagt tcatcccagt gtacaacagc    10640
cccaacatct gccccaagta acaaaaaaca accaatttat cttattctta tctgccacaa   10700
aataatcggt ttcacactat tctcttgtta tacaaaattg acaagtagga aggagaggag   10760
tcatccaaat aaacggtgca cgttctttga gaaaagtctt attttcgta agatccaatt    10820 tcaacaaact tttcttcaag tcaaaattcc tgatagtgta tctcctctcg acgacctctt   10880
gcattgaacg atctccgctt atcatgaaaa gttgcttgga taacaagtat tgcaaggggg   10940
ggacagtagc tattaagtta gtcggcccaa ggaaatggag gagtgatagt ctcgaatatt   11000
attcacctct ttagcattac ccggtctggc tttaaggagt tacgtctttt acgctcgcca   11060
attctttttt ttagaatggt tggtgtcaaa atcgcgagtt gtggaaggtt caagttactc    11120
gattcgtgat tttcaagtat gagtggtgag agagattcga tattttcacg aggtgtattc   11180
gaggtctagt agaacgaagg gtgtcactaa tgaaagtttc aagagttcat catcatcttc   11240
ttctagtaga ttttcgcttt caaatgagta tgaaaattct tcctcttttc tattgatttt   11300
cttcattgtt ttcttcattg ttgtggttgt tattgaaaag aaagaaaatt tataacagaa   11360
aaagatgtca aaaaaaaggt aaaatgaaag agtatcatat acttaaagag ttgcgtagag   11420
ataagtcaaa agaaacagaa ttatagtaat ttcagctaag ttagaattc              11469
```

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 30
ggaattccag tcgcagtcta cattac                                          26

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 31
cgggatccag aggcattaag atttctgg                                        28

<210> SEQ ID NO 32
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 32
cgggatccaa agaaattctc gaggttacat gg                                   32

<210> SEQ ID NO 33
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 33
cgggatccgg ggtaattttt actaatttca tg                                      32

<210> SEQ ID NO 34
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 34
cgggatcccg tatgtctcac tgtgtttgtg gc                                      32

<210> SEQ ID NO 35
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 35
cgggatcccc ctacatacat atatcagatt ag                                      32

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 36
ccatcgatac tttaagtgat ttgatggc                                           28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 37
cgggatcctg ttctgattct tgatttcc                                           28

<210> SEQ ID NO 38
<211> LENGTH: 2122
<212> TYPE: DNA
<213> ORGANISM: Solanum tuberosum

<400> SEQUENCE: 38
gtatgtctca ctgtgtttgt ggctgtgtgt gttttttct ctgtcttttt gtgttttgtg          60 taattgggc tctttaaagt tggtattgtg tatacccttt tgagtatagt ctttgaggaa         120
gcaaaatgat gaatcttgat tgacattagt aaggggttgta acttttttgaa gtttggttag     180 gtgtaattga gtttggcttg tgtgtctgtg tgtcgaggtt atttttttgg tttgtgttat       240
tggggattct taaagttgg tattgtgtat acccttttga gtatagtctt tgaggaagca        300
aaaatgatga atcttgattg gcattagtaa aggttgtagc ttttttgaagt gtggttaggt      360

-continued

```
gtaattgagt ttggcttgtg tgtctgtgtg ttttggaatc ctgatgtgtg tcaagtcctg      420
atatgggtcg aggttctttc tttggtttgt gtaattgggg gttcttaaaa gttggtatta      480 tgtaccttt taagaatagt gtctgagaaa gcaaaatcga tgaattttga ttgacagcat       540
attctttgag aaagcaaaaa atggtgagtt tcatggaga aacttgattg acattactaa      600
aggtagcaac tttttcaact cctgatatgg gtcaaggttc tttgtttggt ttgtgtaatt      660
tggggttctt tgaagtttg agaaagaaaa attatgattt tcatggaga aatttgattt       720 acattaataa aggtagtagc ttttaaagt gtggtcagct gtaatgagtt cagcttggtt      780
taaaggggcc ctacatatgg tgctttctgg tgagatattt gttgctccac catacgagtt      840
ataagaatca tagtgttagg atcttttttc ttttttttt cattttttcac ttgactagct       900 actagaggag tgatcttgac ggcggaaaat cttagaaagg ggaaggttgt ttgcatcaac     960
tggtgttata tgtgcaagga gacgggagat gatgtagatc atcttcttct tcattgtggt      1020
ctttccatga ggttatgatg tgatatgttt gaatggtttg gtacttcttg gctatgccaa      1080
gaactgtgaa agaattgata ttcagttgga agtgtggagt tggaagagtg gaagaattga      1140
cacttggttc cattagcttt aatgtgggtg gtgtggagag agagagaaat aggagagctt      1200
ttgagggggt agagttgagc tttcctcagt tgagaagtag cctttgatat ctttttttt      1260 ttttttttgta cacccataga attcccaatt gtatagaaga ttgggtggag tttgtagaga     1320 atcatcttt gtagtagatt ctttaccttt tggtatatcc attgtataca gccaggcctt      1380
tgactatgtt tatgaatgaa tatacattac ttgaaaaaaa aagaagtgaa gccagtctgt     1440 tgtaccttg tagacaatgt tgttgcagca tcttgataat tccctgaaaa ttgtctccct      1500
gaaggaatag tttggttgat attgattatt tcttggtttg tttaattcgg tgttcttgaa      1560
ggccatttta aatcctttga cattgttaaa ggtgtttaca agtgttggtc tgggtttaaa     1620
agcacctctt gtatggtgct ttctggagtg atctttcttc ctccaaaaga gaagttgcaa      1680
gaatcagtgt gtgtactttt ttctcttgta tgatcagatc ttttttcaat ttttccgttt      1740
tagttgattt atccatatag tgaaagttgg tgtcatagtt gctgtttgtg gacttcctgt     1800
aaaagttttt tgatatactt aaaaaattgt cacacagaag aaagagtttt ttaccattac      1860
ttaagctaga tgggactgtt tgattcttag accaaataat gaacctttt gttctcttaa      1920 cgtgtacttg aaatagtttg gtaaaattgt gataggaaaa aagataattc ttgattgctt      1980
ttggagcatc acttctaatc ataaagtct ttgctctctt caaccatgaa tgataaattg       2040
gacacttatg tggccctaag ttgctctcag tagtggtctt taattgtgga gatataacta     2100
atctgatata tgtatgtagg ga                                              2122
```

<210> SEQ ID NO 39
<211> LENGTH: 2309
<212> TYPE: DNA
<213> ORGANISM: Solanum tuberosum
<220> FEATURE:
<221> NAME/KEY: CDS
<222> LOCATION: (2..127, 2247..2309)

<400> SEQUENCE: 39

```
g tat aca ctc tct gga gtt cgt ttt cct act gtt cca tca gtg tac         46
  Tyr Thr Leu Ser Gly Val Arg Phe Pro Thr Val Pro Ser Val Tyr
   1               5                  10                  15 aaa tct aat gga ttc agc agt aat ggt gat cgg agg aat gct aat att        94
Lys Ser Asn Gly Phe Ser Ser Asn Gly Asp Arg Arg Asn Ala Asn Ile
          20                  25                  30
```

-continued

| | |
|---|---|
| tct gta ttc ttg aaa aaa cac tct ctt tca cgt atgtctcact gtgtttgtgg<br>Ser Val Phe Leu Lys Lys His Ser Leu Ser Arg<br>              35                    40 | 147 |
| ctgtgtgtgt tttttctct gtcttttgt gttttgtgta attggggctc tttaaagttg | 207 |
| gtattgtgta taccttttg agtatagtct ttgaggaagc aaaatgatga atcttgattg | 267 |
| acattagtaa gggttgtaac tttttgaagt ttggttaggt gtaattgagt ttggcttgtg | 327 |
| tgtctgtgtg tcgaggttat tttttggtt tgtgttattg gggatcttaa aagttggtat | 387 |
| tgtgtatacc cttttgagta tagtctttga ggaagcaaaa atgatgaatc ttgattggca | 447 |
| ttagtaaagg ttgtagcttt tgaagtgtg gttaggtgta attgagtttg cttgtgtgt | 507 |
| ctgtgtgttt tggaatcctg atgtgtgtca agtcctgata tgggtcgagg ttctttcttt | 567 |
| ggtttgtgta attgggggtt cttaaaagtt ggtattatgt acctttttaa gaatagtgtc | 627 |
| tgagaaagca aaatcgatga attttgattg acagcatatt cttgagaaa gcaaaaaatg | 687 |
| gtgagttttc atggagaaac ttgattgaca ttactaaagg tagcaacttt ttcaactcct | 747 |
| gatatgggtc aaggttcttt gtttggtttg tgtaatttgg ggttctttga agttttgaga | 807 |
| aagaaaaatt atgattttc atggagaaat ttgatttaca ttaataaagg tagtagcttt | 867 |
| ttaaagtgtg gtcagctgta atgagttcag cttggtttaa aggggcccct acatatggtg | 927 |
| cttttctggtg agatatttgt tgctccacca tacgagttat aagaatcata gtgttaggat | 987 |
| ctttttttctt tttttttca tttttcactt gactagctac tagaggagtg atcttgacgg | 1047 |
| cggaaaatct tagaaagggg aaggttgttt gcatcaactg gtgttatatg tgcaaggaga | 1107 |
| cgggagatga tgtagatcat cttcttcttc attgtggtct ttccatgagg ttatgatgtg | 1167 |
| atatgtttga atggtttggt acttcttggc tatgccaaga actgtgaaag aattgatatt | 1227 |
| cagttggaag tgtggagttg aagagtggaa agaattgaca cttggttcca ttagctttaa | 1287 |
| tgtgggtggt gtggagagag agagaaatag gagagctttt gaggggggtag agttgagctt | 1347 |
| tcctcagttg agaagtagcc tttgatatct tttttttttt ttttttgtaca cccatagaat | 1407 |
| tcccaattgt atagaagatt gggtggagtt tgtagagaat catctttttgt agtagattct | 1467 |
| ttacctttg gtatatccat tgtatacagc caggcctttg actatgttta tgaatgaata | 1527 |
| tacattactt gaaaaaaaa gaagtgaagc cagtctgttg tacctttgta gacaatgttg | 1587 |
| ttgcagcatc ttgataattc cctgaaaatt gtctccctga aggaatagtt tggttgatat | 1647 |
| tgattatttc ttggtttgtt taattcggtg ttccttgaagg ccattttaaa tccttttgaca | 1707 |
| ttgttaaagg tgtttacaag tgttggtctg ggtttaaaag caccctcttgt atggtgcttt | 1767 |
| ctggagtgat ctttcttcct ccaaaagaga agttgcaaga atcagtgtgt gtacttttt | 1827 |
| ctcttgtatg atcagatctt ttttcaattt ttccgtttta gttgatttat ccatatagtg | 1887 |
| aaagttggtg tcatagttgc tgtttgtgga cttcctgtaa aagttttttg atatacttaa | 1947 |
| aaaattgtca cacagaagaa agagttttt accattactt aagctagatg ggactgtttg | 2007 |
| attcttagac caaataatga acctttttgt tctcttaacg tgtacttgaa atagtttggt | 2067 |
| aaaattgtga taggaaaaaa gataattctt gattgctttt ggagcatcac ttctaatcat | 2127 |
| aaaagtcttt gctctcttca accatgaatg ataaattgga cacttatgtg gccctaagtt | 2187 |
| gctctcagta gtggtcttta attgtggaga tataactaat ctgatatatg tatgtagggg | 2246 |
| aag atc ttg gct gaa aag tct tct tac aat tcc gaa tcc cga cct tct<br>Lys Ile Leu Ala Glu Lys Ser Ser Tyr Asn Ser Glu Ser Arg Pro Ser<br>            45                50                55 | 2294 |
| aca gtt gca gca tcg | 2309 |

Thr Val Ala Ala Ser
    60

<210> SEQ ID NO 40
<211> LENGTH: 63
<212> TYPE: PRT
<213> ORGANISM: Solanum tuberosum

<400> SEQUENCE: 40

Tyr Thr Leu Ser Gly Val Arg Phe Pro Thr Pro Ser Val Tyr Lys
 1               5                  10                  15

Ser Asn Gly Phe Ser Ser Asn Gly Asp Arg Arg Asn Ala Asn Ile Ser
                20                  25                  30

Val Phe Leu Lys Lys His Ser Leu Ser Arg Lys Ile Leu Ala Glu Lys
             35                  40                  45

Ser Ser Tyr Asn Ser Glu Ser Arg Pro Ser Thr Val Ala Ala Ser
         50                  55                  60

<210> SEQ ID NO 41
<211> LENGTH: 906
<212> TYPE: PRT
<213> ORGANISM: Solanum tuberosum

<400> SEQUENCE: 41

Met Glu Ile Asn Phe Lys Val Leu Ser Lys Pro Ile Arg Gly Ser Phe
 1               5                  10                  15

Pro Ser Phe Ser Pro Lys Val Ser Gly Ala Ser Arg Asn Lys Ile
                20                  25                  30

Cys Phe Pro Ser Gln His Ser Thr Gly Leu Lys Phe Gly Ser Gln Glu
             35                  40                  45

Arg Ser Trp Asp Ile Ser Ser Thr Pro Lys Ser Arg Val Arg Lys Asp
     50                  55                  60

Glu Arg Met Lys His Ser Ser Ala Ile Ser Ala Val Leu Thr Asp Asp
 65                  70                  75                  80

Asp Asn Ser Thr Met Ala Pro Leu Glu Glu Asp Val Lys Thr Glu Asn
                 85                  90                  95

Ile Gly Leu Leu Asn Leu Asp Pro Thr Leu Glu Pro Tyr Leu Asp His
            100                 105                 110

Phe Arg His Arg Met Lys Arg Tyr Val Asp Gln Lys Met Leu Ile Glu
        115                 120                 125

Lys Tyr Glu Gly Pro Leu Glu Glu Phe Ala Gln Gly Tyr Leu Lys Phe
    130                 135                 140

Gly Phe Asn Arg Glu Asp Gly Cys Ile Val Tyr Arg Glu Trp Ala Pro
145                 150                 155                 160

Ala Ala Gln Glu Ala Glu Val Ile Gly Asp Phe Asn Gly Trp Asn Gly
                165                 170                 175

Ser Asn His Met Met Glu Lys Asp Gln Phe Gly Val Trp Ser Ile Arg
            180                 185                 190

Ile Pro Asp Val Asp Ser Lys Pro Val Ile Pro His Asn Ser Arg Val
        195                 200                 205

Lys Phe Arg Phe Lys His Gly Asn Gly Val Trp Val Asp Arg Ile Pro
    210                 215                 220

Ala Trp Ile Lys Tyr Ala Thr Ala Asp Ala Thr Lys Phe Ala Ala Pro
225                 230                 235                 240

Tyr Asp Gly Val Tyr Trp Asp Pro Pro Ser Glu Arg Tyr His Phe
                245                 250                 255

```
Lys Tyr Pro Arg Pro Lys Pro Arg Ala Pro Arg Ile Tyr Glu Ala
            260                 265                 270

His Val Gly Met Ser Ser Glu Pro Arg Val Asn Ser Tyr Arg Glu
            275                 280                 285

Phe Ala Asp Asp Val Leu Pro Arg Ile Lys Ala Asn Asn Tyr Asn Thr
            290                 295                 300

Val Gln Leu Met Ala Ile Met Glu His Ser Tyr Tyr Gly Ser Phe Gly
305                 310                 315                 320

Tyr His Val Thr Asn Phe Phe Ala Val Ser Ser Arg Tyr Gly Asn Pro
                325                 330                 335

Glu Asp Leu Lys Tyr Leu Ile Asp Lys Ala His Ser Leu Gly Leu Gln
            340                 345                 350

Val Leu Val Asp Val Val His Ser His Ala Ser Asn Asn Val Thr Asp
            355                 360                 365

Gly Leu Asn Gly Phe Asp Ile Gly Gln Gly Ser Gln Glu Ser Tyr Phe
    370                 375                 380

His Ala Gly Glu Arg Gly Tyr His Lys Leu Trp Asp Ser Arg Leu Phe
385                 390                 395                 400

Asn Tyr Ala Asn Trp Glu Val Leu Arg Phe Leu Leu Ser Asn Leu Arg
                405                 410                 415

Trp Trp Leu Glu Glu Tyr Asn Phe Asp Gly Phe Arg Phe Asp Gly Ile
            420                 425                 430

Thr Ser Met Leu Tyr Val His His Gly Ile Asn Met Gly Phe Thr Gly
            435                 440                 445

Asn Tyr Asn Glu Tyr Phe Ser Glu Ala Thr Asp Val Asp Ala Val Val
    450                 455                 460

Tyr Leu Met Leu Ala Asn Asn Leu Ile His Lys Ile Phe Pro Asp Ala
465                 470                 475                 480

Thr Val Ile Ala Glu Asp Val Ser Gly Met Pro Gly Leu Gly Arg Pro
                485                 490                 495

Val Ser Glu Gly Gly Ile Gly Phe Val Tyr Arg Leu Ala Met Ala Ile
            500                 505                 510

Pro Asp Lys Trp Ile Asp Tyr Leu Lys Asn Lys Asn Asp Glu Asp Trp
            515                 520                 525

Ser Met Lys Glu Val Thr Ser Ser Leu Thr Asn Arg Arg Tyr Thr Glu
            530                 535                 540

Lys Cys Ile Ala Tyr Ala Glu Thr His Asp Gln Ser Ile Val Gly Asp
545                 550                 555                 560

Lys Thr Ile Ala Phe Leu Leu Met Asp Lys Glu Met Tyr Ser Gly Met
                565                 570                 575

Ser Cys Leu Thr Asp Ala Ser Pro Val Val Asp Arg Gly Ile Ala Leu
            580                 585                 590

His Lys Met Ile His Phe Phe Thr Met Ala Leu Gly Gly Glu Gly Tyr
            595                 600                 605

Leu Asn Phe Met Gly Asn Glu Phe Gly His Pro Glu Trp Ile Asp Phe
    610                 615                 620

Pro Arg Glu Gly Asn Asn Trp Ser Tyr Asp Lys Cys Arg Arg Gln Trp
625                 630                 635                 640

Asn Leu Ala Asp Ser Glu His Leu Arg Tyr Lys Phe Met Asn Ala Phe
                645                 650                 655

Asp Arg Ala Met Asn Ser Leu Asp Glu Lys Phe Ser Phe Leu Ala Ser
            660                 665                 670

Gly Lys Gln Ile Val Ser Ser Met Asp Asp Asp Asn Lys Val Val Val
```

```
              675                 680                 685
Phe Glu Arg Gly Asp Leu Val Phe Val Phe Asn Phe His Pro Lys Asn
        690                 695                 700
Thr Tyr Glu Gly Tyr Lys Val Gly Cys Asp Leu Pro Gly Lys Tyr Arg
705                 710                 715                 720
Val Ala Leu Asp Ser Asp Ala Trp Glu Phe Gly Gly His Gly Arg Thr
                725                 730                 735
Gly His Asp Val Asp His Phe Thr Ser Pro Glu Gly Ile Pro Gly Val
            740                 745                 750
Pro Glu Thr Asn Phe Asn Gly Arg Pro Asn Ser Phe Lys Val Leu Ser
        755                 760                 765
Pro Ala Arg Thr Cys Val Ala Tyr Tyr Arg Val Asp Glu Arg Met Ser
770                 775                 780
Glu Thr Glu Asp Tyr Gln Thr Asp Ile Cys Ser Glu Leu Leu Pro Thr
785                 790                 795                 800
Ala Asn Ile Glu Glu Ser Asp Glu Lys Leu Lys Asp Ser Leu Ser Thr
                805                 810                 815
Asn Ile Ser Asn Ile Asp Glu Arg Met Ser Glu Thr Glu Val Tyr Gln
            820                 825                 830
Thr Asp Ile Ser Ser Glu Leu Leu Pro Thr Ala Asn Ile Glu Glu Ser
        835                 840                 845
Asp Glu Lys Leu Lys Asp Ser Leu Ser Thr Asn Ile Ser Asn Ile Asp
850                 855                 860
Gln Thr Val Val Ser Val Glu Glu Arg Asp Lys Glu Leu Lys Asp
865                 870                 875                 880
Ser Pro Ser Val Ser Ile Ile Ser Asp Val Pro Ala Glu Trp Asp
                885                 890                 895
Asp Ser Asp Ala Asn Val Trp Gly Glu Asp
            900                 905

<210> SEQ ID NO 42
<211> LENGTH: 44
<212> TYPE: PRT
<213> ORGANISM: Solanum tuberosum

<400> SEQUENCE: 42

Met Val Tyr Thr Leu Ser Gly Val Arg Phe Pro Thr Val Pro Ser Val
1               5                   10                  15

Tyr Lys Ser Asn Gly Phe Ser Ser Asn Gly Asp Arg Arg Asn Ala Asn
            20                  25                  30

Ile Ser Val Phe Leu Lys Lys His Ser Leu Ser Arg
        35                  40

<210> SEQ ID NO 43
<211> LENGTH: 21
<212> TYPE: PRT
<213> ORGANISM: Solanum tuberosum

<400> SEQUENCE: 43

Lys Ile Leu Ala Glu Lys Ser Ser Tyr Asn Ser Glu Ser Arg Pro Ser
1               5                   10                  15

Thr Val Ala Ala Ser
            20
```

What is claimed is:

1. A method for affecting starch branching enzyme activity in a starch producing plant cell, plant tissue, plant organ, or plant, comprising expressing in said plant cell, plant tissue, plant organ, or plant:
   (a) a first nucleotide sequence which comprises a first intron of a potato gene encoding a class A starch branching enzyme in an antisense orientation, wherein the first nucleotide sequence does not contain a sequence that is antisense to an exon sequence naturally associated with the first intron,
   (b) linked to a second nucleotide sequence which comprises a second intron of a potato gene encoding a class B starch branching enzyme in an antisense or sense orientation.

2. A method according to claim 1, wherein the activity of at least one of the starch branching enzymes is reduced or eliminated.

3. A method according to claim 1, wherein the first nucleotide sequence comprises the complement of SEQ ID NO:38, or a fragment thereof.

4. A method according to claim 1, wherein the first nucleotide further comprises a promoter.

5. An antisense sequence comprising a nucleotide sequence which is the complement of SEQ ID NO:38, or a nucleotide sequence with at least 95% similarity to SEQ ID NO:38.

6. A vector comprising a first nucleotide sequence which comprises a first intron of a potato gene encoding a class A starch branching enzyme in an antisense orientation, linked to a second nucleotide sequence which comprises a second intron of a potato gene encoding a class B starch branching enzyme in an antisense or a sense orientation, wherein the first nucleotide sequence does not contain a sequence that is antisense to an exon sequence naturally associated with the first intron.

7. A plant cell comprising the vector according to claim 6.

8. A transgenic plant cell, plant tissue, plant organ, or plant, each comprising the vector of claim 6.

9. A transgenic plant comprising the vector of claim 6.

10. The method according to claim 4, wherein thpromoter comprises SEQ ID NO:14.

* * * * *